United States Patent
Gulyás et al.

(10) Patent No.: US 12,161,613 B2
(45) Date of Patent: *Dec. 10, 2024

(54) TOPICAL PHARMACEUTICAL COMPOSITION CONTAINING PHOSPHOLIPIDS

(71) Applicant: EGIS GYÓGYSZERGYÁR ZRT., Budapest (HU)

(72) Inventors: Anita Gulyás, Telki (HU); Krisztina Móricz, Budapest (HU); Dániel Ulej, Budapest (HU); Gábor Gigler, Budapest (HU); Edit Pap, Pecel (HU); Adrienn Pálvölgyi, Tatabanya (HU); István Gacsályi, Vac (HU); Zoltán Varga, Inárcs (HU); András Ferenc Wacha, Budapest (HU); Attila Bóta, Budapest (HU)

(73) Assignee: EGIS GYÓGYSZERGYÁR ZRT., Budapest (HU)

( * ) Notice: Subject to any disclaimer, the term of this patent is extended or adjusted under 35 U.S.C. 154(b) by 0 days.

This patent is subject to a terminal disclaimer.

(21) Appl. No.: 18/273,684

(22) PCT Filed: Jan. 24, 2022

(86) PCT No.: PCT/HU2022/050002
§ 371 (c)(1),
(2) Date: Jul. 21, 2023

(87) PCT Pub. No.: WO2022/157524
PCT Pub. Date: Jul. 28, 2022

(65) Prior Publication Data
US 2024/0082190 A1    Mar. 14, 2024

(30) Foreign Application Priority Data

Jan. 22, 2021  (HU) .................................. P2100019
Jan. 22, 2021  (HU) .................................. P2100020

(51) Int. Cl.
*A61K 31/197*  (2006.01)
*A61K 9/00*    (2006.01)
*A61K 9/06*    (2006.01)
*A61K 47/24*   (2006.01)
*A61P 25/04*   (2006.01)

(52) U.S. Cl.
CPC .......... *A61K 31/197* (2013.01); *A61K 9/0014* (2013.01); *A61K 9/06* (2013.01); *A61K 47/24* (2013.01); *A61P 25/04* (2018.01)

(58) Field of Classification Search
None
See application file for complete search history.

(56) References Cited

U.S. PATENT DOCUMENTS

2017/0290769 A1*  10/2017  Kisak ....................... A61K 9/06

FOREIGN PATENT DOCUMENTS

CN    101322712 A    12/2008
WO    2014168228 A1  10/2014

OTHER PUBLICATIONS

Schwarz J S, Weisspapir M R, Friedman D I: "Enhanced Transdermal Delivery of Diazepam by Submicron Emulsion (SME) Creams", Pharmaceutical Research, Springer US, New York, vol. 12, No. 05, May 1, 1995 (May 1, 1995), New York, pp. 687-692, XP008003571, ISSN: 0724-8741, DOI: 10.1023/A:1016255408348.

Elnaggar Yosra S.R.; El-Refaie Wessam M.; El-Massik Magda A.; Abdallah Ossama Y.: "Lecithin-based nanostructured gels for skin delivery: An update on state of art and recent applications", Journal of Controlled Release, Elsevier, Amsterdam, NL, vol. 180, Feb. 14, 2014 (Feb. 14, 2014), Amsterdam, pp. 10-24, XP028833703, ISSN: 0168-3659, DOI: 10.1016/j.jconrel.2014.02.004.

International search report PCT/HU2022/050002 dated May 23, 2022 (pp. 1-3).

* cited by examiner

*Primary Examiner* — Nannette Holloman
(74) *Attorney, Agent, or Firm* — Millen, White, Zelano & Branigan; Csaba Henter

(57) ABSTRACT

The present invention relates to a topical pharmaceutical composition comprising pregabalin and a reduced micellar phospholipid as an active ingredient, which results in a prolonged analgesic effect of pregabalin. The product can reduce neuropathic pain by at least 5 hours.

11 Claims, 14 Drawing Sheets

PGA0450717 (SAMPLE 1) FF-TEM images

PGA0450717 (SAMPLE-2) FF-TEM images

TOPICAL PHARMACEUTICAL COMPOSITION CONTAINING PHOSPHOLIPIDS

The present invention relates to a topical pharmaceutical composition comprising pregabalin as active ingredient for the treatment of pain, especially for treatment of chronic pain disorders. Such disorders include, but are not limited to, neuropathic pain, in peripheral neuropathic pain, such as the pain experienced by diabetic patients or by patients who have had herpes zoster (shingles), and central neuropathic pain, such as the pain experienced by patients who have had a spinal-cord injury; diabetic neuropathy, causalgia, brachial plexus avulsion, occipital neuralgia, reflex sympathetic dystrophy, fibromyalgia, gout, phantom limb pain, burn pain, and other forms of neuralgic, neuropathic, and idiopathic pain syndromes

BACKGROUND OF THE INVENTION

The compound of the invention is a known agent useful for the treatment of pain, especially the treatment of neuropathy and in antiseizure therapy for central nervous system disorders such as epilepsy, Huntington's chorea, cerebral ischemia, Parkinson's disease, tardive dyskinesia, spasticity and for the treatment of generalized anxiety disorder. Pregabalin as active ingredient was first described in European patent No. EP641330. The use of treatment for pain including neuropathy was first published in the description of European patent No. EP934061. Pregabalin has been marketed in solid oral capsules such as Lyrica® in the EU since 2004. Lyrica® is available as capsules (white: 25, 50 and 150 mg; white and orange: 75, 225 and 300 mg; orange: 100 mg; light orange: 200 mg) and as an oral solution (20 mg/ml). Neuropathic pain may be associated with abnormal sensations called dysesthesia or pain from normally non-painful stimuli (allodynia). It may have continuous and/or episodic (paroxysmal) components. The latter resemble stabbings or electric shocks. Common symptoms include burning or coldness, "pins and needles" sensations, numbness, and itching. Up to 7-8% of the European population is affected, and in 5% of patients it may be severe. Neuropathic pain may result from disorders of the peripheral nervous system or the central nervous system (brain and spinal cord). Thus, neuropathic pain may be divided into peripheral neuropathic pain, central neuropathic pain, or mixed (peripheral and central) neuropathic pain. Systemic treatment of neuropathy with pregabalin, e.g. using oral capsules may result in several adverse reactions such as dizziness, somnolence, dry mouth, edema, blurred vision, weight gain, and "thinking abnormal" (primarily having difficulties with concentration/attention). Taking into consideration that peripheral neuropathic pain is connected to a distinct part of the body surface, topical treatment seems to be possible. The description of WO14168228 patent application discloses a topical composition containing 0.2-3% of pregabalin in aqueous solution or in a gel in which pregabalin is dissolved in water. The compositions containing 1 and 3% of pregabalin had pain alleviation effect, but after 1.5-2 hours the effect decreased (tables 4 and 9). Gabapentin, the predecessor compound of pregabalin was used for the topical treatment of neuropathic pain in combination with ketamine, ibuprofen, and baclofen. In the International Journal of Pharmaceutical Compounding Vol. 18 No. 6 [November December] 2014 (pages 504-511) the authors examine the topical availability of gabapentin in different gel systems. 1% and 5% lipoderm, lipobase gels and poloxamer lecithin organogel were examined.

There are several liquid or semisolid compositions known from the prior art which appeared to be suitable for formulation of pregabalin in a topical delivery system.

The inventors of the international patent application WO2002094220 describe oral solutions. According to the examples, gabapentin oral solution can be prepared by using water and glycerol which is suitable for oral solution. Gabapentin has similar physical, chemical and pharmaceutical properties compared to pregabalin, therefore compositions containing gabapentin are good starting points for the development of compositions comprising pregabalin. A similar oral solution is disclosed in European patent application No.: EP1543831 with the difference that pregabalin is used as active ingredient and hydroxyethyl-cellulose as thickener and does not contain glycerol. The composition of this composition is similar to the marketed oral solution of pregabalin (Lyrica® solution). Based on the facts disclosed in U.S. Ser. No. 10/004,710B2 patent we expected that these solutions have significant pain alleviating effect even when applied topically. The inventors of this description found that the solution was effective even without any percutaneous absorption promoting ingredient. Pregabalin showed allodynia pain alleviating effect in Mouse Nerve Ligation Model/MNL/. According to the results, after topical administration of the 2.5% aqueous solution without any other ingredients, the alleviating effect had a maximum at 1 hour, then decreased, the reduction was significant. After 3 hours and 6 hours later the effect essentially disappeared. According to an example, the same aqueous solution of pregabalin reduced the neuropathic pain in a human patient for 6 hours. According to the used grading, the pain was grade 7 in a ten-point scale, which imposes serious obstruction of sleep. The pain was markedly ameliorated after about 30 minutes (grade 3 or 4) according to the description. It suggests that the effect in the case of human patients may be longer than in mice, but the reduction would be faster. Our attempt to use the marketed Lyrica @ oral solution having a similar composition (besides pregabalin and water comprising only a sweetener and preservatives) in our experiment, was unsuccessful. Lyrica® was ineffective. Furthermore, application of a liquid preparation on the body surface is also difficult. The patent suggests that viscosity may be modified by thickeners and suggests that pregabalin may be partly in crystalline form if the concentration is higher, but no such examples were disclosed. According to other inventors, the permeability of the compounds such as pregabalin through skin is low, therefore, the modification of the compound or addition of permeability enhancers is necessary for the preparation of an effective topical composition. According to the description of the US patent application No. US20050209319 the formation of a suitable derivative of pregabalin which decomposes to pregabalin in the skin may be used for more effective transdermal compositions. Such compounds may have better permeability than pregabalin, but as new compounds, extensive preclinical examinations, toxicological screening, and full clinical investigations are also necessary, which are risky and expensive. The same problem is apparent with newly synthetized excipients which are mentioned in the description of CN108703946B. The results of using these new excipients were demonstrated in rat pain threshold experiments. In the rat experiments these compounds proved that enhancers may help the permeability of pregabalin compared to a composition which does not contain enhancers. In the description of U.S. Pat.

No. 8,394,759B2 patent discloses the use of a mixture of fatty acid esters as penetration enhancers. The patent suggests that a mixture of several different cetyl esters can assist pregabalin absorption through the skin. The patent suggests that pregabalin can be used in an amount of 0.01-15% in stick gel. There is no specific example for the use of pregabalin in the description. The description of US20170290778 patent application discloses compositions comprising: one or more active agents; and about 0.1 weight percent to about 5.0 weight percent of an extracellular matrix component or a fragment thereof having an average molecular weight of about 2,000 Daltons to about 60,000 Daltons. The penetration of the compositions through human skin is measured in vitro. Unfortunately, there is no example for the composition comprising pregabalin. The description of WO2017172603 patent application discloses compositions which comprise dimethyl sulfoxide (DMSO) as penetration enhancer in an amount of 1-30% of the composition. DMSO as dipolar aprotic solvent is a very good enhancer for penetration through the skin. Unfortunately, the use of DMSO may pose a risk as it may cause adverse reactions. DMSO contents in compositions of the examples of the description of WO2017172603 patent application are between 14-30% which is high. Another possibility for the transdermal treatment of neuropathic pain is the combination of different active ingredients which can have either additive or synergistic effect with pregabalin. U.S. Ser. No. 10/512,655B1 patent describes B vitamin compositions for the treatment of neuropathic pain and as an analgesic. The suggested amount of pregabalin is between 0.001-0.5%, but there is no example for topical composition comprising pregabalin. WO2020069013A1 suggests that besides the component to be absorbed by the skin the topical composition should contain a vasodilator to help the absorption of the active ingredient. The patent application mentions pregabalin as active ingredient, but neither working examples, nor results of the absorption of pregabalin containing composition are presented. Further patent applications relate to topical gels comprising pregabalin. Inventors of US20090247635 patent application prepared a cream comprising 10% of pregabalin and used it for the treatment of pruritis. The composition of the cream was not disclosed. Only long lists of ingredients were given in the description.

According to our experiments compositions containing pregabalin in an aqueous solution can not contain pregabalin in sufficient concentration to maintain the pain killer effect for more than three hours by topical administration. Even it happens if the transdermal bioavailability is acceptable. Taking into consideration that a three-hour painless sleeping period is insufficiently short, it is obvious that there is a need for a topical composition having longer pain alleviation effect. Therefore, there was a long-felt need for a local therapy for the treatment of diabetic neuropathy or post herpetic neuralgia having preferably about at least 5 hour-long pain alleviation effect with low systemic exposure to lower the side effects of pregabalin.

Our aim was to develop a stable topical pharmaceutical composition for the treatment of neuropathic pain, preferably peripheric neuropathic pain or post herpetic neuralgia (PHN) which has a longer pain alleviating effect than 3, more preferably more than 5 hours. Taking into consideration that the affected body surface in case of Diabetic neuropathy (DPN) can reach about 28% of the body surface, our aim to decrease the systemic effect of the topical composition as much as possible was also important.

SUMMARY OF THE INVENTION

We found surprisingly that our aim can be achieved by preparation of a topical composition comprising pregabalin and a phospholipid wherein the phospholipid phase or the composition comprising pregabalin and phospholipid and a solvent or a mixture of solvents are homogenized with a high pressure homogenizer. More particularly, the topical pharmaceutical composition according to the present invention comprises pregabalin in preferably more than 2.5 weight % and a phospholipid in a 0.1-5 weight % in a gel or cream formulation in which the phase which comprises the phospholipid is milled by a high pressure homogenizer with or without the presence of pregabalin. We found surprisingly that in the case that the phospholipid phase is milled by a high pressure homogenizer, the pregabalin mixed into the thus obtained structure has extended effect with the advantage that the pain alleviation effect develops in a short time, then lasts much longer, even more than 5 hours, than the effect of the same quantitative composition lasting less than 3 hours if components are mixed and homogenized without the use of a high pressure homogenizer.

All physical and stability properties of the compositions having the same composition of ingredients were the same but the pain alleviation effect was significantly longer in cases where an high pressure homogenizer was used.

Thus, the improved unexpected effect was a result of the use of an HPH homogenizer, which causes high shearing forces in the composition during the process. Apparently, these forces cause the unexpected advantageous effect of the present invention, therefore it is a reasonable expectation that every homogenization process causing similar high shearing forces is also suitable for the preparation of the compositions of the present application. The person skilled in the art can choose the equipment and operation parameters thereof to achieve the required high shearing forces. Such equipment which may be suitable for the preparation of the compositions of the present invention are those in which e.g. similar turbulence, local cavitation, shear test, impact speed are applied. Such devices include high shear mixers, homogenizers, shredders, grinders such as ultrasonic mixers, rotor/stator homogenizers, TURRAX homogenizers, bead mills, colloid mills, high shear mixers, slit homogenizers, microfluidizers and so on. Without being bound by theory, micelles of phospholipids in the solvent or composition—which are usually formed in protic solvents—are partly or fully destroyed by high shearing forces of the high pressure homogenization procedure. No such effect can be observed when using methods of homogenization with smaller shearing forces. Mixing and homogenization of the formulations in each step—when a non-high pressure homogenizer was used—mixing and homogenization was performed with a Stephan UMC 5 electronic device (see Example R-3). It is very surprising that the thus prepared product keeps the advantageous form and properties even after 12 months without any change and that the compounds having been prepared according to the present invention have the longest pain alleviation effect Additionally, we surprisingly found that Small-angle X-ray scattering diagram of the composition which was prepared in a way that the phospholipid phase or the composition comprising pregabalin and phospholipid is mixed with a high pressure homogenizer is different from the compositions having the same composition but did not undergo high pressure homogenization. The micelle contribution scaling factor ($I_0$) derived from the diagram of the Small-angle X-ray scattering measurement is less than 0.00025 $cm^{-1}sr^{-1}$, preferably less than 0.00023 $cm^{-1}sr^{-1}$, more preferably less than 0.00021 $cm^{-1}sr^{-1}$, most preferably less than 0.00019 $cm^{-1}sr^{-1}$ characterizes the compositions of the present invention, in which at least the phospholipid and a solvent or a solvent mixture were homogenized with high pressure homogenizer. Since both the measurement data and the curve fit contain uncertainties, the composition of the present invention can be described as a pregabalin-containing topical pharmaceutical composition comprising pregabalin and a phospholipid, wherein the pregabalin and phospholipid are dispersed in the form, and having a micelle contribution scaling factor ($I_0$) derived from the small angle X-ray scatter measurement diagram of less than or equal to $0.00019 \pm 0.00004$ cm$^{-1}$sr$^{-1}$, preferably less than or equal to $0.00017 \pm 0.00004$ cm$^{-1}$sr$^{-1}$ with, more preferably less than $0.00015 \pm 0.00004$ cm$^{-1}$sr$^{-1}$.

DETAILED DESCRIPTION OF THE PRESENT INVENTION

Our aim was achieved by development of a topical pharmaceutical composition containing more than 2.5 weight % of pregabalin and a phospholipid of 0.1-5 weight %, preferably 0.1-3 weight %, in a gel or cream formulation in which the cream or gel phase of the formula containing phospholipids is homogenized by a high pressure homogenizer in the presence or in absence of pregabalin, preferably micronized pregabalin. High pressure homogenization is carried out preferably at least once, more preferably the homogenization is carried out by a high pressure homogenizer 1-125 times, preferably 3-10 times.

We found surprisingly that a topical pharmaceutical composition containing more than 2.5 weight % of pregabalin and a phospholipid of 0.1-3 weight % in a gel or cream formulation in which the cream or gel phase of the formula containing phospholipids is homogenized by a high pressure homogenizer at least once without or with the presence of pregabalin has a long lasting, at least 5-hour pain alleviation effect in the topical treatment of mice (Mouse model of neuropathic pain). According to the preferred embodiments, the gel or cream containing pregabalin is homogenized by a high pressure homogenizer 1-125 times, preferably 3-10 times.

According to the present invention the composition comprises pregabalin in dispersed form. This means that the composition comprises pregabalin not only in dissolved but also in solid form because of the low solubility of pregabalin. Solubility of pregabalin is poor in any solvents. Water and protic solvents such as pharmaceutically acceptable alcohols having one or more hydroxyl groups such as ethanol, propanol, isopropanol, butanol, sec-butanol as alcohols having one hydroxyl group, propylene glycol having two, or glycerin having three hydroxyl groups are used as solvents according to the present invention.

According to the present invention water and the above-mentioned alcohols, more preferably water, ethanol or isopropanol are used as solvent. In an advantageous embodiment, water mixed with an alcohol, preferably with isopropanol is used. Above 2.5 weight % of pregabalin content, in the mixture of pregabalin and water—apart from dissolved pregabalin—the residual part of pregabalin remains in solid, dispersed form in the composition. Thus, the meaning that pregabalin is in dispersed form according to the present invention is that the composition comprises pregabalin not only in dissolved but also in solid form. The ratio of the dissolved and dispersed pregabalin depends on the weight percent of pregabalin in the composition, the used solvent and/or the ratio of the used solvents in the mixture, the temperature of the composition and the further excipients used. Shortly, the compositions according to the present invention besides the dispersed pregabalin, can also comprise dissolved pregabalin.

We found surprisingly that the pain alleviation effect of the composition depends on the particle size of the used pregabalin. According to the preferable embodiment of the present invention the pregabalin used as starting material is ground, which means that the $D_{90}$ of particle size of the used pregabalin is less than 200 micrometer, preferably between 20-200 micrometer. More preferably, micronized pregabalin is used as starting material, which has a $D_{90}$ less than 20 micrometer.

According to the present invention, protic solvents are used as solvents. More particularly, water and pharmaceutically acceptable alcohols having one or more hydroxyl groups can be used as solvent. These alcohols can also be substituted. Preferably ethanol, propanol, isopropanol, n-butanol, 2-butanol can be used as alcohol having one hydroxyl group. Propylene glycol and glycerin can be used as alcohols having more than one hydroxyl group. Most preferably the composition of the present invention comprises water, ethanol or isopropanol or a mixture thereof as solvent. According to a more advantageous embodiment of the present invention the composition comprises a mixture of water and ethanol or water and isopropanol. The preferable ratio of alcohol to water is between 1:1-1:40, more preferably between 1:10-1:40 most preferably 1:15-1:35 by weight.

Some solvents of the present invention have penetration enhancing effect as well. Such solvents are e.g. isopropanol and ethanol. According to the description these compounds are taken into consideration as solvents. Therefore, in the examples and the description the ratio, e.g. weight % of these compounds in the composition is counted in the rate of solvents and the amount of these solvents are not included in the amount of penetration enhancer ratio.

Phospholipids used in the compositions of the present invention are also well-known penetration enhancers. Taking into consideration that phospholipids and the treatment of phospholipids in the process is crucial, the amount of the phospholipids used in the HPH process is not counted in the amount of the penetration enhancers. But it is not excluded that besides the HPH-processed phospholipids, further phospholipids are added to the composition. In such a case the used further phospholipids are counted as other penetration enhancers.

Phospholipids according to the present invention are natural or synthetic phospholipids. As phospholipids, phosphatidic acid (phosphatidate), phosphatidylethanolamine (cephalin), phosphatidylcholine, phosphatidylserine, phosphoinositides, such as phosphatidylinositol, phosphatidylinositol phosphate, phosphatidylinositol bisphosphate, phosphatidylinositol trisphosphate, ceramide phosphorylcholine, ceramide phosphorylethanolamine, ceramide phosphoryllipid or derivatives and mixtures thereof can be used. According to the present invention preferably phosphatidylcholine (lecithin), more preferably soya lecithin, deoiled soya lecithin, lipoid P75, lipoid S75 can be used.

The topical composition of the present invention is gel, cream, or gel-cream. To achieve the advantageous gel, cream or gel-cream properties, in the preferable embodiments of the present invention a rheology modifier is also used. As rheology modifier, poloxamers, polyethylene glycol, synthetic polymers such as carbomers (polyacrylic acid), hydroxyalkyl celluloses, such as hydroxyethylcellulose and vegetable gums such as xanthan gum or guar gum can also be used. Preferably carbomers, most preferably carbomer 980 is used.

These compositions according to the present invention usually comprise other excipients besides the pharmaceutically active ingredients.

The compositions of the present invention can comprise emollients as excipients which are effective moisturisers that can help maintain the skin's natural protective barrier and rehydrate the skin. According to the preferable embodiment of the present invention the topical pharmaceutical composition can be obtained by a process where it can comprise as emollient ammonium lactate, vitamins A, D, and E, lanolin, lanolin alcohol, propylene glycol dibenzoate, vegetable oils, plant extracts, fatty alcohol esters, fatty acid esters, fatty alcohols, synthetic polymers, silicon compounds, fatty acids, mineral oil derivatives, waxes or a mixture thereof. For example as vegetable oil emollient, coconut oil, soy oil, soybean oil, grape seed oil, hazelnut oil, *Helianthus annuus* (sunflower) seed oil, hemp seed oil, hydrogenated olive oil, hydrogenated soybean oil, peanut oil, pecan oil, *Persea gratissima* (avocado) oil, pistachio seed oil, plum seed oil, limnanthes alba (meadowfoam) seed oil, *Oenothera biennis* oil, *Olea europaea* fruit oil, *Olea europaea* oil unsaponifiables, olive oil/olive fruit oil, orbignya oleifera seed oil, *Oryza sativa* oil, palm oil *Palmaria palmata* extract, *Prunus armeniaca, Prunus domestica* seed oil, *Prunus dulcis*, pumpkin seed extract, rapeseed oil, *quinoa* oil, sweet almond oil, rice bran oil, rice oil, *Ricinus communis*, safflower seed oil, *Sesamum indicum* (sesame) seed oil, *Triticum vulgare* oil, walnut oil, wheat germ oil, *Pongamia glabra* seed oil, moringa oleifera seed oil or a mixture thereof can be used. As plant extract emmollient for example *Haslea ostrearia* extract, *Helianthus* oil, *Himanthalia elongata* extract, Irish moss extract, *Mangifera indica* (mango) seed butter, *Mastocarpus stellatus, Microcystis aeruginosa*, murumuru seed butter, *Padina pavonica* extract, *Orbignya martiana, Prunus amygdalus dulcis, quinoa* oil, *Rosa canina, Rosa centifolia*, shea butter, hydrolyzed algae extract or a mixture thereof can be used. As fatty alcohol esters, for example lauryl lactate, Myristyl myristate, Neopentyl glycol dicaprylate, octyl palmitate, octyl stearate, triisocetyl citrate, trioctyldodecyl citrate, *Raphanus sativus* (radish) seed oil or a mixture thereof can be used. As fatty acid ester emollient for example stearates, glyceryl stearate, glycol stearate, hexyl laurate, hydrogenated coco-glyceride, hydrogenated palm glycerides, methyl glucose sesquistearate, octyldodecyl myristate, octyldodecyl neopentanoate, polyglycerol monostearate, polyglyceryl 2 triisostearate, polyglyceryl-4 isostearate, polyglyceryl-6 isostearate, propylene glycol isostearate, propylene glycol laurate, stearyl stearate, tridecyl stearate, triglycerides, trilaurin, trioctanoin, wheat germ glycerides, glyceryl behenate, glyceryl rosinate, lauryl laurate, *Salvia hispanica* (chia) seed oil, *Argania spinosa* kernel oil, caprylyl caprylate/caprate, ethylhexyl olivate, isoamyl cocoate, sucrose stearate, diisostearyl polyglyceryl-3 dimer dilinoleate, ceteareth-6 olivate, cococaprylate, behenyl behenate, glyceryl stearate citrate or a mixture thereof can be used. As fatty alcohol for example hexyldecanol, octyldodecanol, stearyl alcohol, myristyl alcohol or a mixture thereof can be used. As synthetic polymer emollient for example hydrogenated polydecene, hydrogenated polyisobutene, PEG-10 rapeseed sterol, PEG-100 stearate, PEG-20 methyl glucose sesquistearate, PEG-40 hydrogenated castor oil, PEG-60 almond glycerides, PEG-60 hydrogenated castor oil, PEG-7 glyceryl cocoate, PEG-8, PEG 90M, PEG/PPG-17/6 copolymer (PEG stands for polyethylene glycol; PPG stands for polypropylene glycol), polyethylene, PPG-3 benzyl ether myristate, sodium PEG-7 olive oil carboxylate, triethoxysilylethyl polydimethylsiloxyethyl hexyl dimethicone, methyl gluceth-20 benzoate, polyglyceryl-10 stearate, polyglyceryl-4 laurate, polyglyceryl-4 olivate, polyglyceryl-3 stearate or a mixture thereof can be used. As silicon type emollient for example methicone, PEG-10 dimethicone, PEG-10 dimethicone/vinyl dimethicone crosspolymer, PEG/PPG-18/18 dimethicone, PEG/PPG-20/15 dimethicone, pentaerythrityl tetraoctanoate, methyl trimethicone, methylsilanol mannuronate, methylsilanol PEG-7 glyceryl cocoate, polymethylsilsesquioxane, stearyl methicone, trimethylsiloxysilicate or a mixture thereof can be used. As fatty acid type emollient for example hydrolyzed jojoba esters, linoleic acid, palmitic acid, stearic acid, trihydroxystearin or a mixture thereof can be used. As mineral oil derivative type emollient for example petrolatum, paraffinum liquidum or a mixture thereof can be used. As wax type emollient for example beeswax or synthetic beeswax can also be used. Preferably as emollient vitamins A, D, and E, lanolin, lanolin alcohol, propylene glycol di-benzoate, vegetable oils, plant extracts, fatty alcohol esters, fatty acid esters, fatty alcohols, synthetic polymers, silicon compounds, fatty acids, mineral oil derivatives, waxes or a mixture thereof, most preferably as fatty acid ester cetyl palmitate, fatty alcohols as octyldodecanol, as fatty acid derivative Decylis oleas, as vegetable oil coconut oil or a mixture thereof is used.

According to the preferable embodiment of the present invention the topical pharmaceutical composition can comprise further penetration enhancers such as DL-alpha-tocopherol, dimethylsufoxide diethyl sebacate, glycofurol, isopropyl myristate, isopropyl palmitate, lauric acid, linoleic acid, methylpyrrolidone, myristic acid, oleic acid, oleyl alcohol, palmitic acid*, polyoxyethylene alkyl ethers, polyoxylglycerides e.g. caprylocaproyl polyoxylglycerides, polyoxylglycerides e.g. lauroyl polyoxylglycerides, polyoxylglycerides such as linoleoyl polyoxylglycerides, polyoxylglycerides polyoxylglycerides such as stearoyl polyoxylglycerides, propylene glycol monolaurate, squalane, e.g. thymol, tricaprylin, *Camphora racemica*, menthol, cetyl decanoate, cetyl laurate, cetyl myristate, cetyl myristoleate, cetyl oleate, cetyl palmitate, cetyl palmitoleate, cetyl stearate, or a mixture of further penetration enhancers are used. Alcohols which are used as solvent also have penetration enhancer effect.

According to the preferable embodiments of the present invention preservatives are also used. As preservatives EDTA, EDTA derivatives, aromatic preservatives such as para-hydroxy benzoates, thimerosal, chlorohexidine, benzyl alcohol and benzalkonium chloride, phenoxyethanol, preferably benzyl alcohol, or a mixture thereof, more preferably a mixture of benzyl alcohol and EDTA can be used. EDTA is used as complex forming compound besides its preservative role.

According to the preferable embodiments of the present invention the topical pharmaceutical composition can also comprise pH regulators. Preferably ammonia, ammonium solution, alkali or alkali earth metal hydroxides, carbonates, hydro-carbonates, or organic bases, such as primary, secondary or tertiary amines, most preferably aqueous ammonia solution can be used as pH modifier.

Homogenization is a process which has a crucial role in the present invention. For the sake of clarity in the case of using high pressure homogenization process (HPH) which is able to change the structure of the composition such a way that the unexpected result—extended period of pain alleviation—is achieved, this fact is mentioned as "HPH homogenization", "high pressure homogenization", "homogenized with HPH homogenizer" and the like. Where the homogenization process causes the homogenous distribution of the mixed ingredients only terms "homogenization", "mixing", "mixed" and the like are used. The essential feature of the present invention is that at least in one process step, the phospholipid has to be homogenized with a HPH homogenizer in the presence of a solvent, such as water, an above-mentioned alcohol or a mixture thereof.

The critical effect of high shear HPH homogenization on efficacy is clearly demonstrated in a rat model of formalin-induced neuropathy in rats. In Example 4, two gels of the same composition containing 15% pregabalin prepared different ways were compared to placebo formulations of similar compositions. Namely, PGA0450717 (composition R-3), which was not subjected to HPH homogenization, was compared with placebo PGA0440717, (Composition P-1) whose lipid phase was also not treated with HPH homogenizer. The effect of the two formulations over the total time of measurement and in the second phase, which causes symptoms characteristic of neuropathic nerve damage, was not different between the two formulations. The results were completely different in the case of comparing PGA0470717 also containing 15% pregabalin, with PGA0460717 placebo, During our development we have tried to use different gels e.g. lipoderm, but the stability of these gels was not acceptable. We found surprisingly that phospholipids can be used as penetration enhancers in topical composition comprising pregabalin for the treatment of neuropathic pain, preferably peripheric neuropathic pain or post herpetic neuralgia (PHN), but a long lasting effect can be achieved only when the phospholipids are homogenized with a high pressure homogenizer in the presence of a solvent, preferably in the presence of water, more preferably in the presence of a mixture of water and an alcohol. The pain alleviation effect of different pharmaceuticals can be modelled according to medial plantar nerve ligation model hereinafter referred to as MNLP test (-Sci Rep-2016, http://www.nature.comscientificreports/). Using this test, we found surprisingly that topical treatment with a composition which comprises a phospholipid homogenized with a high pressure homogenizer (HPH) has significant and long lasting effects in plantar withdrawal threshold experiments. Contrarily, the topical treatment in which the phospholipids were not homogenized with a high pressure homogenizer the effect was decreased after three hours rapidly. In FIG. 1. the MNLP test of three similar compositions are shown as follows:

| | Batch No | | | | |
|---|---|---|---|---|---|
| | PGA2180719 | PGA2190719 | PGA0450717 Process | PGA0470717 | PGA1601018 |
| Compound | R-1 (reference example) g | R-2 (reference example) g | R-3 (reference example) g | WE-1 (Working example of the present invention) g | WE-2 (Working example of the present invention) g |
| Pregabalin (micronized*, ground**) | 2.5000* | 5.0000** | 15.0000* | 15.0000* | 5.0000* |
| LECITHIN (LIPOID P 75) * SOYA LECITHIN (Deoiled Soya Lecithin) | 0.5000 | 0.5000 | 0.5000* | 0.5000* | 1.0000 |
| Decylis oleas/Kollicream DO/ | 1.2500 | 1.2500 | 1.2500 | 1.2500 | 1.2500 |
| Coconut oil refined | 5.0000 | 5.0000 | 0.0000 | 0.0000 | 10.0000 |
| Octyldodecanol | | | 2.5000 | 2.5000 | |
| Isopropyl alcohol | 10.0000 | 10.0000 | 5.0000 | 5.0000 | 10.0000 |
| DL-alpha-Tocopherol | 0.2500 | 0.2500 | 0.2500 | 0.2500 | 0.2500 |
| Benzyl alcohol | 1.0000 | 1.0000 | 0.0000 | 0.0000 | 2.0000 |
| EDTA | 0.0025 | 0.0025 | 0.0025 | 0.0025 | 0.0025 |
| Carbomers (980) | 0.4000 | 0.4000 | 0.3750 | 0.3750 | 0.3750 |
| Ammonium solution (25 weight % aqueous) | 0.3136 | 0.3136 | 0.2940 | 0.2940 | 0.2940 |
| Purified water | 78.7839 | 76.2839 | 74.8285 | 74.8285 | 69.8285 |
| Sum | 100.00 | 100.00 | 100.00 | 100.00 | 100.00 |
| Number of HPH of lipid phase | 0 | 0 | 0 | 5 | 5 |
| Plantar withdrawal threshold test conditions | | | | | |
| Pregabalin | 2.5% | 5% | 15% | 15% | 5% |
| Area (on MPNL paw) | 2 cm$^2$ | 2 cm$^2$ | 2 cm$^2$ | 2 cm$^2$ | 2 cm$^2$ |
| Amount of composition [μl] (on MPNL paw) | 50 μl | 20 μl | 50 μl | 50 μl | 20 μl |
| Number of the group (n) | 6 | 7 | 5 | 6 | 6 | namely, PGA0470717 caused a significant reduction in pain throughout the total time of measurement and in the second phase also compared to placebo. Both formulations, PGA0470717 and placebo PGA0460717, were prepared by homogenizing the mixture of swollen phospholipid and isopropyl alcohol 5 times with an HPH homogenizer. The results are shown in FIG. 10.

Thus, phospholipids in the compositions of PGA2180719, PGA2190719 and PGA0450717 were not homogenized in the presence of a solvent with an HPH homogenizer, meanwhile PGA0470717 and PGA1601018 were prepared according to the present invention.

In all cases the pain alleviation effect developed in 30 minutes, which suggests that absorption through the skin of the compositions is excellent for each composition, but the effect of the composition PGA2180719, which comprises pregabalin in dissolved form, is reduced almost to the starting level after five hours. Using the composition PGA2190719, which comprises pregabalin in dispersed form, the effect reduces almost by half of the maximum level after five hours. The composition PGA1601018 according to the present invention has significant effect after five hours. The difference of intact paw and MPNL paw after five hours compared to the baseline shows that the effect is significant even after five hours.

Furthermore, based on the article Bennett G J, at al (Pain., A peripheral mononeuropathy in rat that produces disorders of pain sensation like those seen in man. 1988 April; 33(1):87-107) we have developed a method for the examination of the compositions of the present invention. Thus, we have examined the compositions according to the present invention also with a different model for measuring the alleviation of the peripheral neuropathic pain also. Namely, we have carried out examinations on rats using Chronic constriction injury (CCI) model. Three weeks following nerve injury rats were assessed for hind paw mechanical withdrawal thresholds. The paw withdrawal threshold (PWT) was determined with an Electronic von Frey device according to the modified up-down method of Dixon (Efficient analysis of experimental observations, Annu Rev Pharmacol Toxicol. 1980; 20:441-62). The results also proved that the compositions of the present invention have advantageous effect on the alleviation of peripheral neuropathic pain. Using 5 mg pregabalin gel (PGA2330320)/4 cm² in 50 µl 10% cream causes more than five hours pain alleviation in rats. The method and results are shown in example 3 and on FIG. 9.

As we mentioned above, the effect of the compositions according to the invention can be detected very quickly, within 30 minutes, e.g. also when using the MPNL model. The absorption compositions of PGA 1601018 containing 5% pregabalin and PGA 1591018 containing 10% pregabalin were examined. This indicates that one hour after treatment, the gels were completely absorbed in both cases, although the gel contained dispersed solid pregabalin particles. FIG. 11 shows photographs of the surface of the pig skin before, one hour after, and two hours after treatment. After one hour, even the 10% pregabalin formulation appeared to be completely absorbed. The PGA1671118 composition of the present invention (WE-2 method) was compared to other commercially available creams containing dispersed particles, namely Neogranormone® and a more advanced form of Mometasone Medimer®. The formulation (PGA1671118) was "absorbed" less than one hour, while the other two commercial formulations were still visible on the pig skin after 3 hours. After 3 hours, there was no deposition or crystallization visible under magnification for PGA1671118. Photos from the experiment are shown in FIG. 12.

During our research we have not found any physical differences between the compositions which could explain the difference of the effects. Neither the compositions of the present invention homogenized with an HPH homogenizer, nor the reference compositions had liposomes. Our first expectation was that using lecithin, a liposomal structure should have formed, which was expected to cause good absorption properties and long-lasting pain alleviating effect. On the contrary, neither the compositions according to the present invention homogenized with an HPH homogenizer, nor the compositions homogenized in a usual mixer equipment showed liposomal structure examined by electron microscope. Moreover, there was no significant difference between the different compositions in these tests. PGA0450717 and PGA0470717 were tested by Frozen Fracture Transmission Electron Microscopy (FF-TEM). The results did not show significant differences between the compositions. We found only that in the matrix of these two samples small particles as well as drug crystals of several µm in size were dispersed (FIG. 7).

Subsequently we tested our compositions of PGA0450717 and PGA0470717 with SAXS (Small-angle X-ray scattering) method. This method is used for quantifying nanoscale electron density differences in a sample. Measured SAXS curves of gel formulations PGA0450717 and PG0470717 and their fitted model functions are demonstrated on FIG. 9. The SAXS curves of samples PGA0450717 and PGA0470717 do not show any peaks in the observed q-range which would indicate a regular, periodic structure in the nano scale. The only feature that appears is in the range of 0.7 nm$^{-1}$<q<3 nm$^{-1}$: an increase in intensity different from the monotonically decaying baseline. The baseline can be interpreted using Porod's law, a well-known feature in small-angle scattering (Porod 1951). According to this, the tail part of the scattering curves of three-dimensional objects with smooth surfaces (e.g. nanoparticles) follow a power-law function of −4 exponent. This behavior is not limited to nearly spherical particles, though. Several other systems exhibit power-law scattering with different exponents (Schmidt 1991). We therefore account for the contribution of components larger than what SAXS can resolve (e.g. pregabalin crystallites, see the above mentioned FF-TEM images in FIG. 7) using a power-law baseline, extended with a constant term which is the common scattering feature of small-molecular solvents (e.g. water).

$$I_{h\acute{a}tt\acute{e}r}(q)=Aq^{-\alpha}+C$$

As a first approximation, the micelles can be regarded as an ensemble of spheres of narrow size distribution with homogeneous electron density inside them. Their scattering intensity can be calculated as follows:

$$I_{micell\acute{a}k}(q)=\int_0^\infty P(r,R_0,dR)I_{g\ddot{o}mb}(q,r)dr$$

where $I_{sphere}$ (q, r) is the scattering intensity of a sphere of homogeneous electron density with radius r and volume V, where $I_{sphere}(q,r)$ is the scattering intensity of a single sphere of homogeneous electron density with radius r and volume V, and the size distribution function P (r, R$_0$, dR) is assumed to be a Gaussian one with a n expected R$_0$ value and half-width dR.

The data fitted to the scatter plots of the micellar samples are shown in the table below.

| Sample | PGA0450717 | PG0470717 |
|---|---|---|
| Power function background scaling factor (A) | 0.003 ± 0.001 | 0.004 ± 0.002 |
| Power function background exponent (α) | 2.990 ± 0.328 | 2.813 ± 0.338 |
| Constant background (C; cm$^{-1}$ sr$^{-1}$) | 0.020 | 0.020 |
| Micelle scattering contribution scaling factor (I$_0$)*100; (cm$^{-1}$sr$^{-1}$ ) | 0.028 ± 0.004 | 0.021 ± 0.005 |
| Average radius of micelles (R$_0$; nm) | 2.001 ± 0.266 | 2.067 ± 0.433 |
| Mean radius distribution parameter of micelles (dR; nm) | 0.423 ± 0.122 | 0.470 ± 0.161 |

Size- and shape-related parameters of both the micellar part (R$_0$, dR) and the crystalline part (exponent α) match well between the two samples within experimental uncertainty, therefore the relative composition weight parameters (I$_0$ and A) can be compared. The scattering contribution of the micelles, the relative weight of which with respect to the power function background—parameter I$_0$—is smaller in the case of the sample PGA0470717, i.e. the sample contains fewer micelles. All other parameters, especially the expected value of 2 nm characterizing the size distribution of the micelles and a half-width close to 0.45 nm, match well for the two samples.

We have examined further samples by SAXS, and found that when the Micelle scattering contribution scaling factor ($I_0$) is smaller than $2.2 \times 10^{-4}$ the composition shows longer and stronger effect as follows:

| Batch No | PGA0470717 (PGA0591017) | PGA0601017 | PGA0611017 | PGA1510918 | PGA1520918 |
|---|---|---|---|---|---|
| Process type: | WE-1 | WE-1 | WE-1 | WE-3 | WE-3 |
| Pregabalin | 15% | 12% | 10% | 10% | 37.5% |
| Micelle scattering contribution scaling factor ($I_0$)*100; ($cm^{-1}sr^{-1}$) | 0.018 ± 0.001 (0.015 ± 0.001) | 0.014 ± 0.001 | 0.016 ± 0.001 | 0.010 ± 0.001 | 0.010 ± 0.001 |
| n (Number of HPH of lipid phase) | 5 | 5 | 5 | 125 | 5 |

These data suggest that the cause of the long-lasting and strong effect of the compositions of the present invention may be based on the fact that high pressure homogenization of phospholipids inhibits the formation of micelles, therefore a significant part of these molecules is dispersed in the matrix. In other words, high pressure homogenization destroys the micelles, which are usually formed in the aqueous phase, partly or completely. According to our experiment the resulting structure (which may be formed e.g. by high pressure homogenization) is stable. Value of ($I_0$) a in the compositions of the present invention is between 0 and 0.00025 $cm^{-1}sr^{-1}$, preferably between 0.00001 and 0.00023 $cm^{-1}sr^{-1}$, more preferably 0.00003 and 0.00021 $cm^{-1}sr^{-1}$ most preferably between 0.00005 and 0.00019 $cm^{-1}sr^{-1}$. It can also be characterized by that the value of ($I_0$) in the compositions according to the invention is between 0 and $0.00019 \pm 0.00004$ $cm^{-1}sr^{-1}$, preferably between 0.00001 and $0.00017 \pm 0.00004$ $cm^{-1}sr^{-1}$, more preferably between 0.00003 and 0.00021 $cm^{-1}sr^{-1} \pm 0.00004$ $cm^{-1}sr^{-1}$ most preferably is between 0.00005 and $0.00015 \pm 0.00004$ $cm^{-1}sr^{-1}$.

We have also examined the effect of the numbers of HPH homogenization process. We found surprisingly that one HPH homogenization results in a longer pain alleviating effect compared to the reference products which were not homogenized with an HPH homogenizer. The effects seem to be stronger after three or more HPH homogenization steps according to the tests as follows:

| Batch No | PGA0980418 | PGA0990418 | PGA1000418 | PGA1040418 | PGA1510918 |
|---|---|---|---|---|---|
| Process type | WE-1 | WE-1 | WE-1 | WE-1 | WE-3 |
| Pregabalin (micronized) | 15.0000 | 15.0000 | 15.0000 | 15.0000 | 10.0000 |
| Phospholipid (lechitin) | 0.5000 | 0.5000 | 0.5000 | 0.5000 | 0.2500 |
| number of HPH of lipid phase | 1 | 3 | 4 | 9 | 125 |
| Plantar withdrawal threshold test conditions | | | | | |
| Pregabalin % | 15% | 15% | 15% | 15% | 10% |
| Area (on MPNL paw) | 2 $cm^2$ | 2 $cm^2$ | 2 $cm^2$ | 2 $cm^2$ | 2 $cm^2$ |
| Amount of composition [μl] (on MPNL paw) | 20 μl | 20 μl | 20 μl | 20 μl | 20 μl |

| Batch No | PGA0980418 | PGA0990418 | PGA1000418 | PGA1040418 | PGA1510918 |
|---|---|---|---|---|---|
| Number of the group (n) | 6 | 7 | 7 | 6 | 7 |

On FIG. 2 results of the same quantitative compositions homogenized 1, 3, 4, 9 times can be seen. There is some improvement with the increasing number of the HPH homogenization. In the course of the search for the limitation of the procedure we have HPH homogenized a similar composition 125 times. The result shows that the long-lasting effect does not disappear after even that many HPH homogenization steps.

During the development of the present invention, we found surprisingly that the pain alleviation effect can be achieved with compositions having pregabalin content in a very large range, from 3% to 37.5%. Preferably the range of pregabalin content is between 3-15%, more preferably 3-10%, most preferably 5-10%.

FIG. 3 shows the comparative results of compositions PGA1370718, PGA1450718, and PGA1460718. All compositions were effective and based on the results on one hand it seems that the effect is dose proportional. On the other hand, there is no significant difference between the effect of compositions comprising 10% or 15% of pregabalin. Both compositions have high pain alleviation effect at 30 minutes which stays at a high level for at least 5 hours. The effect of the composition containing 5% of pregabalin developed more slowly. After one hour this composition has a strong effect which lasted at least five hours. Comparing compositions PGA1591018 and PGA1601018 modification of other ingredients can facilitate fast absorption. These compositions have similarly fast onset of the effect within 30 minutes and the effect also lasts at least five hours. Further-

| | Batch No | | | | | |
|---|---|---|---|---|---|---|
| | PGA1591018 | PGA1601018 | PGA1370718 | PGA1450718 | PGA1460718 | PGA1520918 |
| | | | Process type | | | |
| | WE-2 | WE-2 | WE-3 | WE-3 | WE-3 | WE-3 |
| Pregabalin (micronized) | 10.0000 | 5.0000 | 15.0000 | 10.0000 | 5.0000 | 37.5000 |
| Phospholipid (lecithin) | 1.0000 | 1.0000 | 0.2500 | 0.2500 | 0.2500 | 0.2500 |
| Decylis oleas/ Kollicream DO/ | 1.2500 | 1.2500 | 1.2500 | 1.2500 | 1.2500 | 1.2500 |
| Octyldodecanol | 0.0000 | 0.0000 | 0.0000 | 0.0000 | 0.0000 | 0.0000 |
| Coconut oil | 10.0000 | 10.0000 | 0.0000 | 0.0000 | 0.0000 | 0.0000 |
| Isopropyl alcohol | 10.0000 | 10.0000 | 2.5000 | 2.5000 | 2.5000 | 2.5000 |
| DL-alpha-Tocopherol | 0.2500 | 0.2500 | 0.1250 | 0.1250 | 0.1250 | 0.1250 |
| EDTA | 0.0025 | 0.0025 | 0.0025 | 0.0025 | 0.0025 | 0.0025 |
| Benzyl alcohol | 2.0000 | 2.0000 | 0.0000 | 0.0000 | 0.0000 | 0.0000 |
| Carbomers (Carbopol 980) | 0.3750 | 0.3750 | 0.3750 | 0.3750 | 0.3750 | 0.3750 |
| Ammonium solution (25 weight % aqueous) | 0.2940 | 0.2940 | 0.2940 | 0.2940 | 0.2940 | 0.2940 |
| All ingredients | 35.1715 | 30.1715 | 19.7965 | 14.7965 | 9.7965 | 42.2965 |
| Purified water | 64.8285 | 69.8285 | 80.2035 | 85.2035 | 90.2035 | 57.7035 |
| Sum | 100.00 | 100.00 | 100.00 | 100.00 | 100.00 | 100.00 |
| number of HPH of lipid phase | 5 | 5 | 5 | 5 | 5 | 5 |
| Plantar withdrawal threshold test conditions | | | | | | |
| Pregabalin % | 10% | 5% | 15% | 10% | 5% | 37.5% |
| Area (on MPNL paw) | 2 cm$^2$ | 2 cm$^2$ | 2 cm$^2$ | 2 cm$^2$ | 2 cm$^2$ | 2 cm$^2$ |
| Amount of composition [μl] (on MPNL paw) | 20 μl | 20 μl | 20 μl | 20 μl | 20 μl | 20 μl |
| Number of the group (n) | 6 | 6 | 7 | 7 | 8 | 6 | more, the composition having 37.5% of pregabalin also has a long-lasting effect. Obviously, the high pregabalin content makes the composition harder to spread, but the compositions according to the present invention can be used comprising pregabalin in a wide range of concentration.

According to another embodiment of the present invention the process comprises not only homogenization of the lipid phase by an HPH homogenizer but also the aqueous suspension of pregabalin. Then the lipid phase and the HPH homogenized aqueous dispersion is homogenized, which is shown in working example WE-5 below.

According to an advantageous embodiment of the present invention, the process is carried out by preparation of an aqueous mixture which comprises dispersed pregabalin and a phospholipid and optionally other excipients and homogenized together with an HPH homogenizer 1-125 times, preferably 3-10 times, more preferably 3-5 times.

Particularly the procedure can be carried out as follows: In tenfold amount of purified water Carbopol 980 is swelled, then the pH is adjusted to 7.0 by adding aqueous ammonia solution. Then in ten times the amount of purified water lecithin (e.g. LIPOID P 75) is swelled at 25-40° C., then optionally further excipients such as isopropyl alcohol and DL-alpha-Tocopherol are added to the mixture and homogenized with an aqueous dispersion of pregabalin. Then the thus prepared mixture of dispersed pregabalin and a phospholipid is homogenized with an HPH homogenizer 1-125 times, preferably 3-10 times, more preferably 3-5 times. The thus obtained phase containing pregabalin and phospholipid is mixed to the gel phase, then preferably further excipients are added such as coconut oil, decylis oleas, EDTA and benzyl alcohol. If necessary, at the end further rheology modifier is added.

According to another advantageous embodiment of the present invention the process is carried out by preparation of a gelled aqueous mixture which comprises dispersed pregabalin and a phospholipid and optionally other excipients and homogenized with an HPH homogenizer 1-125 times, preferably 3-10 times, more preferably 3-5 times. Particularly, the procedure can be carried out as follows: In tenfold amount of purified water Carbopol 980 is swelled, then the pH 7.0 is adjusted by adding aqueous ammonia solution. Then in tenfold amount of purified water lecithin (e.g. LIPOID P 75) is swelled at 25-40° C., then optionally further excipients such as isopropyl alcohol and DL-alpha-Tocopherol are added to the mixture and homogenized with an aqueous dispersion of pregabalin. Then the thus obtained mixture is mixed into previously prepared gel phase and the thus obtained composition is homogenized with an HPH homogenizer 1-125 times, preferably 3-10 times, more preferably 3-5 times. If necessary further excipients are added such as coconut oil, decyl oleas, EDTA and benzyl alcohol to the composition. If necessary, at the end further rheology modifier is added.

Furthermore, we found surprisingly, that in the case when the lipid phase and then the whole mixture with pregabalin is also homogenized with a high pressure homogenizer, the thus obtained product has even stronger and longer effect compared to the compounds in which the lipid phase was homogenized by a high pressure homogenizer:

| Batch No | PGA1601018 | PGA2150619 | PGA2211119* |
|---|---|---|---|
| Process type | WE-2 | WE-4 | WE-4 |
| Pregabaline | 5.0000 (micronized) | 5.0000 (ground) | 5.0000 (micronized) |
| Phospholipid (lechitin) | 1.0000 | 0.5000 | 0.5000 |
| Decylis oleas/Kollicream DO/ | 1.2500 | 1.2500 | 1.2500 |
| Octyldodecanol | 0.0000 | 0.0000 | 0.0000 |
| Coconut oil | 10.0000 | 5.0000 | 5.0000 |
| Isopropyl alcohol | 10.0000 | 10.0000 | 10.0000 |
| DL-alpha-Tocopherol | 0.2500 | 0.2500 | 0.2500 |
| EDTA | 0.0025 | 0.0025 | 0.0025 |
| Benzyl alcohol | 2.0000 | 1.0000 | 1.0000 |
| Carbomers (Carbopol 980) | 0.3750 | 0.4000 | 0.4000 |
| Ammonia solution (25 weight % aqueous) | 0.2940 | 0.3136 | 0.3136 |
| All ingredients | 30.1715 | 23.7161 | 23.7161 |
| Purified water | 69.8285 | 76.2839 | 76.2839 |
| Sum | 100.00 | 100.00 | 100.00 |
| number of HPH of lipid phase | 5 | 5 | 5 |
| number of HPH of other composition | 0 | +3 | +3 |
| Plantar withdrawal threshold test conditions | | | |
| Pregabalin % | 5% | 5% | 5% |
| Area (on MPNL paw) | 2 cm$^2$ | 2 cm$^2$ | 2 cm$^2$ |
| Amount of composition [µl] (on MPNL paw) | 20 µl | 20 µl | 20 µl |
| Number of the group (n) | 6 | 6 | 6 |

Comparing the pain alleviation effects of composition PGA1601018 (WE-2 process type, results on FIG. 3) in which the lipid phase was homogenized only 5 times to the composition PGA2150619 (WE-4 process, results on FIG. 4) in which not only the lipid phase but the whole composition—before the addition of a rheology modifier—was homogenized 5 times, we found that the effect was stronger after 30 minutes and after five hours the difference between the stimulus intensity between the intact paw and MPNL paw was significantly smaller in the case of PGA2150619 than in the case of PGA1601018 under the same circumstances. Furthermore, we have examined the effect of the particle size of pregabalin used. We found surprisingly that micronized pregabalin has stronger effect. During the development we compared the effects of compositions PGA2150619 and PGA2211119. The only difference between the compositions was that PGA2211119 comprises smaller, micronized particles of pregabalin. In FIG. 4 it is shown that the smaller particle size of the product increases the effect of the composition. Therefore, in a preferable embodiment of the present invention the pregabalin used is micronized.

According to a preferable embodiment of the present invention the pregabalin used as starting material is ground, which means that the $D_{90}$ particle size of the pregabalin used is less than 200 micrometer, preferably between 20-200 micrometer. More preferably, micronized pregabalin is used as starting material, which has a $D_{90}$ less than 20 micrometer.

$D_{90}$ is the parameter that gives a value less than 90% of the particle size of the test substance that can be determined by laser diffraction particle size determination. The method of determination is given in the experimental section.

We have examined the duration of the effect of compositions of the present invention. We found that the compositions of the present invention have longer pain alleviation effect than 5 hours which was our aim to be achieved. For example, we found that PGA2211119 has significant pain alleviation effect even after 8 hours (FIG. 5).

During the development of the topical pregabalin formulation, it was suggested that not only the effect of treatment of the target area, i.e. the reduction of mechanical hypersensitivity in the neuropathic area, but also the systemic efficacy/effect should be investigated. These studies were also performed in a mouse model of neuropathy. Treatments in these experiments were not applied to the neuropathic leg but farther away from the other (left) hind leg or the shaved upper part of the back, close to neck of mice. In each case, the cream was applied by massaging for 1 minute—or until the cream was absorbed. The size of the treatment surfaces was ~2 cm$^2$ for the foot and ~2 or ~6 cm$^2$ for the upper part of the back, close to neck.

According to our experiments the topical administration of pregabalin has only a slight systemic effect using the test method described above. For example, the composition of PGA2211119 (5% pregabalin content) used in a dose of 20 µl on 2 cm$^2$ of the surface of MPNL paw has significant and long-lasting pain alleviation effect for 5 or even for 8 hours (FIG. 5). In the case when 2.5 times the amount of the experimental dose of pregabalin of composition of PGA2211119 (50 µl) is applied on the upper part of the back, close to neck of the mouse on a 2 cm$^2$ surface, there is no significant pain alleviating effect on the MPNL paw. This shows that no significant amount of pregabalin is absorbed this way so that enough pregabalin gets into the blood stream triggering a systemic pain alleviation effect. Furthermore, even if the 2.5 times therapeutic dose is applied on a 6 cm$^2$ surface on a mouse's upper part of the back, close to neck area which is a considerable part of the full surface of the mouse, there is no significant effect. (see FIG. 6).

Thus, the compositions of the present invention are effective in the treatment of neuropathic pain. According to our experiments on Wistar rats weighing 280-300 g, approx. pregabalin 16.6 mg/kg was administered to the rats which were underwent CCI surgery and showed neuropathic plantar sensitivity on 4 cm$^2$ surface area of the operated sole of rats. When the 5-15% composition of the present invention is applied, the hypersensitivity of the operated paw of the animal soon disappears and the analgesic effect begins to decrease only after 5 hours, i.e. even after five hours the analgesic effect of the composition is significant. It is also possible to apply an amount of 33.3 mg of 15% PGA0470717 or 50.0 mg of 10% PGA2330320 or 100.0 mg of 5% PGA1601018 composition of the present invention to an area of 4 cm$^2$ of the sole of the paw. Since topical administration of the compositions of the present invention at 16.6 mg/kg in rats remains effective for at least 5 hours, although oral administration of the same amount does not cause pain, suggests that in the case of the topical administration of the present invention requires less pregabalin than it is administered orally. Because our pharmacokinetic experiments show that pregabalin enters the bloodstream in very small amounts during topical treatment, it is expected that less pregabalin will be required in humans compared to oral administration, so the side effects of pregabalin would not appear besides the reduction in neuropathic pain.

In summary, compositions of the present invention have long-lasting pain alleviation effect by topical treatment of a composition containing pregabalin without systemic side effects. Therefore, it can be an alternative for patients who have oral pregabalin treatment for pain alleviation of different types of pain such as neuropathic pain, in peripheral neuropathic pain, such as the pain experienced by diabetic patients or by patients who have had herpes zoster (shingles), and central neuropathic pain, such as the pain experienced by patients who have had a spinal-cord injury; diabetic neuropathy, causalgia, brachial plexus avulsion, occipital neuralgia, reflex sympathetic dystrophy, fibromyalgia, gout, phantom limb pain, burn pain, and other forms of neuralgic, neuropathic, and idiopathic pain syndromes, preferable for the treatment neuropathy, diabetic neuropathy, peripheral neuropathic pain, post herpetic pain, most preferably neuropathic pain, preferably peripheric neuropathic pain or post herpetic neuralgia (PHN).

As we disclosed above, the crucial feature of the present invention is that the composition contains a phospholipid as absorption enhancer in a special processed form, namely the used phospholipid, or at least a portion of it has to be mixed and homogenized with a solvent by using an HPH homogenizer or an equipment which can provide similar circumstances. In our theory, the high shear forces, or something connected to the powerful movement of the fluid comprising the phospholipid modifies the phospholipid structure in the mixture in such a way that the new structure is stable for a long time and results in good absorption of pregabalin and an extended period of pain alleviating effect even when pregabalin is dispersed in the composition.

It seems that the HPH homogenization of phospholipid in presence of a solvent significantly reduces the amounts of micelles of phospholipids in the mixture. Phospholipids should be dispersed in the mixture after the HPH treatment. Surprisingly this structure is maintained subsequently for a long time.

According to another aspect of the present invention the topical compositions can be characterized by SAXS measurement. Namely, the diagram of the compositions of the present invention which have longer and stronger effect, made by HPH homogenization of phospholipid, shows that the amount of phospholipid micelles in this composition are decreased compared to the compositions homogenized only by mixing, high share mixing or ball milling. The difference can be measured by the micelle contribution scaling factor of the fitted function of the measurement curve.

From another point of view the present invention relates to a topical pharmaceutical composition comprising pregabalin characterized in that the composition comprises 2.5-40 weight % of pregabalin, preferably 3-20 weight %, more preferably 3-15, most preferably 5-10 weight % of pregabalin and comprises also 0.1-3 weight %, preferably 0.5-1.5, most preferably 0.8-1.2 weight % of phospholipid and wherein the pregabalin and phospholipid are in dispersed form and wherein the micelle contribution scaling factor ($I_0$) derived from the diagram of the Small-angle X-ray scattering measurement is less than or equal to 0.00025 cm$^{-1}$sr$^{-1}$, preferably less than 0.00021 cm$^{-1}$sr$^{-1}$, more preferably less than 0.00019 cm$^{-1}$sr$^{-1}$.

According to a preferred embodiment of the present invention the topical pharmaceutical composition is semisolid, preferably a gel, cream, or gel-cream, more preferably gel-cream. The topical pharmaceutical composition according to the present invention can further comprise 40-90 weight %, preferably, 70-90 weight %, most preferably 75-85 weight % of solvents, 0-20 weight %, preferably 0.1-20 weight %, more preferably 2-15 weight %, more preferably 3-10 weight % of emollients, 0-20 weight %, preferably 0.1-20 weight %, more preferably 2-15 weight %, even more preferably 3-10 weight % of penetration enhancer(s), 0-5 weight %, preferably 0.1-2 weight %, most preferably 0.2-0.5 weight % of rheology modifier.

The topical pharmaceutical composition according to the present invention can comprise excipients as follows:
as phospholipid, e.g. natural or synthetic phospholipids. As phospholipids phosphatidic acid (phosphatidate), phosphatidylethanolamine (cephalin), phosphatidylcholine, phosphatidylserine, phosphoinositides, such as phosphatidylinositol, phosphatidylinositol phosphate, phosphatidylinositol bisphosphate, phosphatidylinositol trisphosphate, ceramide phosphorylcholine, ceramide phosphorylethanolamine, ceramide phosphoryllipid or derivatives and mixtures thereof. According to the present invention preferably phosphatidylcholine (lecithin), more preferably soya lecithin, deoiled soya lecithin, lipoid P75, lipoid S75 can be used.

As solvents water, pharmaceutically acceptable $C_2$-$C_4$ alcohols, more preferably ethanol, propanol, isopropanol, n-butanol, iso-butanol, alcohols having more than one hydroxyl group, preferably glycerol, propylene glycol, more preferably ethanol or isopropanol or a mixture thereof can be used.

As emollient preferably vitamins A, D, and E, lanolin, lanolin alcohol, propylene glycol di-benzoate, vegetable oils, plant extracts, fatty alcohol esters, fatty acid esters, fatty alcohols, synthetic polymers, silicon compounds, fatty acids, mineral oil derivatives, waxes or a mixture thereof, most preferably as fatty acid ester cetyl palmitate, fatty alcohols as octyldodecanol, as fatty acid derivative Decylis oleas, as vegetable oil coconut oil can be used.

As penetration enhancer besides the phospholipid, e.g. DL-alpha-tocopherol, dimethylsufoxide diethyl sebacate, glycofurol, isopropyl myristate, isopropyl palmitate, lauric acid, linoleic acid, methylpyrrolidone, myristic acid, oleic acid, oleyl alcohol, palmitic acid*, polyoxyethylene alkyl ethers, polyoxylglicylglicylester, polyoxylglycerides i.: caprylocaproyl polyoxylglycerides, polyoxylglycerides ii.: lauroyl polyoxylglycerides, polyoxylglycerides such as linoleoyl polyoxylglycerides, polyoxylglycerides such as oleoyl polyoxylglycerides, polyoxylglycerides such as stearoyl polyoxylglycerides, propylene glycol monolaurate, squalane, thymol, tricaprylin, camphora racemica, menthol, cetyl decanoate, cetyl laurate, cetyl myristate, cetyl myristoleate, cetyl oleate, cetyl palmitate, cetyl palmitoleate, cetyl stearate, or a mixture of further penetration enhancers, are used.

As preservative EDTA, EDTA derivatives, aromatic preservatives such as para-hydroxy benzoates, thimerosal, chlorohexidine benzyl alcohol and benzalkonium chloride, preferably benzyl alcohol, phenoxyethanol, more preferably a mixture of benzyl alcohol and EDTA can be used.

As rheology modifier poloxamer, polyethylene glycol, synthetic polymers such as carbomers (polyacrylic acid), preferably carbomer 980, hydroxyalkyl celluloses, preferably hydroxyethyl cellulose and vegetable gums, preferably xanthan gum or guar gum, most preferably carbomers, as pH modifier preferably base type pH modifier, more preferably ammonia, ammonium solution, alkali or alkali earth metal hydroxides, carbonates, hydro-carbonates, or organic bases, such as primary, secondary or tertiary amines, most preferably aqueous ammonia solution can be used.

Without being bound by theory, the high shear forces in connection to the powerful movement of the fluid comprising the phospholipid modifies the phospholipid structure in the mixture in such a way that the new structure is stable for a long time and results in good absorption of pregabalin and an extended period of pain alleviating effect even when pregabalin is dispersed in the composition. According to our theory the number of micelles is reduced significantly because of the high shearing effect of HPH homogenization.

Therefore, our invention further relates to a topical pharmaceutical composition comprising pregabalin and phospholipid obtainable by a process in which a mixture comprising the phospholipid and solvent is homogenized with a high pressure homogenizer and wherein the pregabalin is in dispersed form. According to the present invention the phospholipids can be homogenized with an HPH homogenizer at any phase of the process. The pregabalin can be added at any step of the present invention in an amount which cannot dissolve in full. Thus, the unsolved part of pregabalin is dispersed as solid particles in the mixture.

Thus, our invention also relates a process for the preparation of topical pharmaceutical composition comprising pregabalin and a phospholipid in which
  a phospholipid and a solvent or a mixture of solvents are homogenized with a high pressure homogenizer and pregabalin is admixed to the composition, or
  the phospholipid, solvent and pregabalin are mixed and the thus obtained mixture is homogenized with a high pressure homogenizer, wherein
the thus obtained composition comprises pregabalin in dispersed form.

The preparation of such a composition which comprises besides pregabalin a mixture of a phospholipid and a solvent processed with an HPH homogenizer or an equipment capable of producing a similar effect on said mixture and further excipients, can be performed in several different procedures depending e.g. on the dosing sequence of the ingredients. During our experimental work we found that the dosing sequence is indifferent from the point of view of the result. For example, we can homogenize the phospholipid with or without pregabalin or any other excipients. The essence is that by the end of the procedure, the phospholipid at least in the presence of the solvent and at least once, preferably 1-125 times, more preferably 3-10 times, most preferably 5-10 times has to be processed by HPH or with an equipment having a similar effect.

In a preferable embodiment the composition of the present invention comprises an additional rheology modifier. In other words, the composition of the present invention can be formed into a gel, cream or gel-cream by adding a rheology modifier to the composition.

In a preferable embodiment the composition of the present invention comprises an additional rheology modifier. In other words, the composition of the present invention can be formed into a gel, cream or gel-cream by adding a rheology modifier to the composition.

Our aim by adding the rheology modifier is that a cream, gel, or gel-cream can be administered topically as a fluid. Furthermore, the composition comprises dispersed pregabalin and the dispersion is more easily stabilized in a composition comprising a rheology modifier, such as a poloxamer, polyethylene glycol, synthetic polymers such as carbomers (polyacrylic acid), preferably carbomer 980, hydroxyalkyl celluloses, preferably hydroxyethyl cellulose and vegetable gums, preferably xanthan gum or guar gum, most preferably carbomers. If the gel phase is added to the composition before the HPH homogenization process, it may be necessary to add a further rheology modifier to reform the gel, cream or gel-cream form of the composition because the high shearing forces can destroy the gel, cream or gel-cream form.

Another aspect of the present invention is a process for the preparation of a topical pharmaceutical composition comprising pregabalin and phospholipid which comprises pregabalin and phospholipid in dispersed form in the composition wherein the micelle contribution scaling factor ($I_0$) derived from the diagram of the Small-angle X-ray scattering measurement is less than or equal to $0.00025\ cm^{-1}sr^{-1}$, preferably less than $0.00023\ cm^{-1}sr^{-1}$, more preferably less than $0.00021\ cm^{-1}sr^{-1}$, even more preferably less than $0.00019\ cm^{-1}sr^{-1}$.

The present invention can be characterized by providing a topical pharmaceutical composition comprising pregabalin comprising pregabalin and a phospholipid in a dispersed form and having a micelle contribution scaling factor ($I_0$) derived from a short angle X-ray scatter measurement smaller or equal to $0.00019\pm0.00004\ cm^{-1}sr^{-1}$, preferably less than or equal to $0.00017\pm0.00004\ cm^{-1}sr^{-1}$, more preferably less than $0.00015\pm0.00004\ cm^{-1}sr^{-1}$.

Thus, in a preferable manner the composition according to the present invention can be prepared in a way that a mixture of a phospholipid and water is homogenized with a high pressure homogenizer, then pregabalin and at least one more excipient is added to the mixture and homogenized and the composition comprises 2.5-40 weight % of pregabalin, preferably 3-20 weight %, more preferably 3-15, most preferably 5-10 weight % of pregabalin and comprises also 0.1-3 weight %, preferably 0.5-1.5, most preferably 0.8-1.2 weight % of phospholipid and wherein the phospholipid and pregabalin are in dispersed form and wherein the micelle contribution scaling factor ($I_0$) derived from the diagram of the Small-angle X-ray scattering measurement is less than or equal to $0.00025\ cm^{-1}sr^{-1}$, preferably less than $0.00023\ cm^{-1}sr^{-1}$, more preferably less than $0.00021\ cm^{-1}sr^{-1}$, even more preferably less than $0.00019\ cm^{-1}sr^{-1}$.

From another aspect, the topical composition according to the present invention comprising pregabalin and phospholipid, having micelle contribution scaling factor ($I_0$) derived from the diagram of the Small-angle X-ray scattering measurement less than or equal to $0.00025\ cm^{-1}sr^{-1}$, preferably less than $0.00023\ cm^{-1}sr^{-1}$, more preferably less than $0.00021\ cm^{-1}sr^{-1}$, even more preferably less than $0.00019\ cm^{-1}sr^{-1}$ can be prepared in a way that a mixture of a phospholipid and water is homogenized with a high pressure homogenizer, then pregabalin and at least one more excipient is added to the mixture and homogenized and the composition comprises 2.5-40 weight % of pregabalin, preferably 3-20 weight %, more preferably 3-15, most preferably 5-10 weight % of pregabalin and comprises also 0.1-3 weight %, preferably 0.5-1.5, most preferably 0.8-1.2 weight % of phospholipid and wherein the phospholipid and pregabalin are in dispersed form.

More particularly, the topical pharmaceutical composition can be prepared in a way that the mixture of a phospholipid and a solvent, or a mixture of solvents and optionally other excipients are homogenized with an HPH homogenizer, then a rheology modifier is added, and to the thus obtained mixture pregabalin and optionally other excipients are added and the thus obtained mixture is homogenized, or the mixture of a phospholipid and a solvent, or a mixture of solvents and optionally other excipients are homogenized with an HPH homogenizer, then to the thus obtained mixture pregabalin and optionally other excipients are added and the thus obtained mixture is homogenized, then a rheology modifier is added, or the mixture of a phospholipid and a solvent, or a mixture of solvents and optionally other excipients are homogenized with an HPH homogenizer, and the thus obtained mixture is added to a mixture of pregabalin and optionally other excipients which has been homogenized with an HPH homogenizer separately, then a rheology modifier is added if necessary, or the mixture of a phospholipid and a solvent, or a mixture of solvents and optionally other excipients are homogenized with an HPH homogenizer, then pregabalin and optionally other excipients are added to the phospholipid phase then the thus obtained mixture is homogenized with an HPH homogenizer, then a rheology modifier is added, or the mixture of a phospholipid and a solvent, or a mixture of solvents and optionally other excipients are homogenized with an HPH homogenizer, then pregabalin and optionally other excipients are added to the phospholipid phase then the thus obtained mixture is homogenized with an HPH homogenizer, then if necessary, a further rheology modifier or excipients are added.

According to another embodiment of the present invention the process can be carried out in such a way that the mixture of phospholipid and a solvent or a mixture of solvents, pregabalin and optionally other excipients are homogenized and homogenized with an HPH homogenizer, then a rheology modifier and optionally other excipients are added to the thus obtained mixture and homogenized, or a rheology modifier is added, and the thus obtained composition is homogenized with an HPH homogenizer, then if necessary further excipients are added and the thus obtained mixture is homogenized, the thus obtained composition comprises pregabalin and phospholipid in dispersed form in the mixture and wherein the micelle contribution scaling factor ($I_0$) derived from the diagram of the Small-angle X-ray scattering measurement is less than or equal to $0.00025\ cm^{-1}sr^{-1}$, preferably less than $0.00021\ cm^{-1}sr^{-1}$, more preferably less than $0.00019\ cm^{-1}sr^{-1}$.

More particularly, our invention relates to the process for the preparation of a composition comprising pregabalin and a phospholipid in dispersed form wherein the micelle contribution scaling factor ($I_0$) derived from the diagram of the Small-angle X-ray scattering measurement is less than or equal to $0.00025\ cm^{-1}sr^{-1}$, preferably less than $0.00021\ cm^{-1}sr^{-1}$, more preferably less than $0.00019\ cm^{-1}sr^{-1}$ in which the mixture of phospholipid and a solvent or a mixture of solvents, pregabalin and optionally other excipients are homogenized and homogenized with an HPH homogenizer, then a rheology modifier and optionally other excipients are added to the thus obtained mixture and homogenized, or a rheology modifier is added, and thus obtained composition is homogenized with an HPH homogenizer, then if necessary further excipients are added and the thus obtained mixture is homogenized.

According to the present invention the topical composition is obtainable by a process in which the mixture comprising a phospholipid, a solvent or a mixture of solvents and optionally pregabalin and other excipients are homogenized with a high pressure homogenizer at least 1 time, preferably 1-125 times, more preferably 3-10 times, most preferably 5-10 times.

Thus, the process for the preparation of the topical pharmaceutical composition can be carried out as described above in which the process comprises the HPH homogenization of the mixture of a phospholipid, a solvent or a mixture of solvents and optionally pregabalin and other excipients where the high pressure homogenization is carried out at least 1 time, preferably 1-125 times, more preferably 3-10 times, most preferably 5-10 times.

According to the present invention the topical pharmaceutical composition obtainable by a process according to the present invention comprises more than 2.5 weight % of pregabalin and 0.1-5 weight % of high pressure homogenized phospholipid and pregabalin are in dispersed form in the composition.

More particularly, according to the present invention the topical pharmaceutical composition can be prepared according to the present invention which comprises 2.5-40 weight %, preferably 3-20 weight %, more preferably 3-15 weight %, most preferably 5-10 weight % of pregabalin and 0.1-3 weight %, preferably 0.1-1.5 weight %, most preferably 0.1-1.2 weight % of a phospholipid where the pregabalin is in dispersed form.

Thus, during the process more than 2.5 weight % of pregabalin is added to the composition and 0.1-5 weight % of phospholipid is added and homogenized with an HPH homogenizer.

According to the preferable embodiment of the present invention the thus obtained mixture is formed to gel, cream or gel-cream form.

More particularly, the process according to the present invention is carried out in such a way that 2.5-40 weight %, preferably 3-20 weight %, more preferably 3-15 weight %, most preferably 5-10 weight % of pregabalin is added and 0.1-3 weight %, preferably 0.1-1.5 weight %, most preferably 0.1-1.2 weight % of phospholipid is added and homogenized with an HPH equipment. According to the preferable embodiment of the present invention the thus obtained mixture is formed to gel, cream or gel-cream form.

As we mentioned above the topical pharmaceutical composition obtainable by a process according to the present invention may comprise further excipients e.g. 40-90 weight %, preferably, 70-90 weight %, most preferably 75-85 weight % of solvent, 0-20 weight %, preferably 0.1-20 weight %, more preferably 2-15 weight %, most preferably 3-10 weight % of emollient, 0-20 weight %, preferably 0.1-20 weight %, more preferably 2-15 weight %, most preferably 3-10 weight % of penetration enhancer, 0-20% weight %, preferably 0.1-20 weight %, more preferably 0.1-20, more preferably 0.1-5 weight %, even more preferably 0.1-2 weight %, most preferably 0.2-0.5 weight % of a rheology modifier or a mixture thereof.

For the preparation of a topical composition according to the present invention preferably the above-mentioned excipients can be used. More preferably, the topical composition according to the present invention is obtainable by a process mentioned above with the use of the above-mentioned excipients.

Thus, according to the present invention for the preparation of the topical composition according to the process mentioned above we can use preferably as phospholipid natural or synthetic phospholipids, preferably lecithin, more preferably soya lecithin, deoiled soya lecithin, lipoid P75, lipoid S75, as solvents water, pharmaceutically acceptable $C_2$-$C_4$ alcohols, more preferably ethanol, propanol, isopropanol, n-butanol, iso-butanol, alcohols having more than one hydroxyl group, preferably glycerol, propylene glycol, more preferably ethanol or isopropanol or a mixture thereof, as emollient vitamins A, D, and E, lanolin, lanolin alcohol, propylene glycol di-benzoate, vegetable oils, plant extracts, fatty alcohol esters, fatty acid esters, fatty alcohols, synthetic polymers, silicon compounds, fatty acids, mineral oil derivatives, waxes or a mixture thereof, most preferably as fatty acid ester cetyl palmitate, fatty alcohols as octyldodecanol, as fatty acid derivative Decylis oleas, as vegetable oil coconut oil, as penetration enhancer besides the phospholipid, $C_2$-$C_4$ alcohols, DL-alpha-tocopherol, or a mixture thereof, as preservative EDTA derivatives, aromatic preservatives such as para-hydroxy benzoates, thimerosal, chlorohexidine benzyl alcohol and benzalkonium chloride, preferably benzyl alcohol, more preferably a mixture of benzyl alcohol and EDTA, as rheology modifier poloxamer, polyethylene glycol, synthetic polymers such as carbomers (polyacrylic acid) preferably carbomer 980, hydroxyalkyl celluloses, preferably hydroxyethyl cellulose and vegetable gums, preferably xanthan gum or guar gum, carbomers, as pH modifier preferably base type pH modifier, more preferably ammonia, ammonium solution, alkali or alkali earth metal hydroxides, carbonates, hydro-carbonates, or organic bases, such as primary, secondary or tertiary amines, most preferably aqueous ammonia solution.

The topical composition of the present invention can be obtained from a process wherein the mixture of a phospholipid and a solvent, preferably water or a mixture of water and an alcohol, more preferably ethanol or isopropanol, most preferably a mixture of water and isopropanol and optionally other excipients preferably emollient(s), preferably octyldecanol and/or penetration enhancer(s), preferably DL-alpha-Tocopherol are homogenized with an HPH homogenizer, preferably 1-125 times, more preferably 3-10 times, most preferably 5-10 times using pressure between 500-2000 bar, preferably between 500-1500 bar, most preferably 1000-1500 bar, then the thus obtained mixture is added to a gel phase prepared by swelling a rheology modifier, preferably polyethylene glycol, synthetic polymers preferably carbomers (polyacrylic acid) more preferably carbomer 980, hydroxyalkyl celluloses, preferably hydroxyethyl cellulose and vegetable gums, preferably xanthan gum or guar gum, most preferably carbomer 980 in a solvent, preferably water and the pH of the gel phase is adjusted with a pH modifier if necessary, preferably aqueous ammonium solution, then pregabalin and optionally other excipients, preferably emollient(s), preferably Decylis oleas and preservatives preferably an aqueous EDTA solution are admixed to the thus obtained mixture and homogenized, or the mixture of a phospholipid and a solvent, preferably water or a mixture of water and an alcohol, more preferably ethanol or isopropanol, most preferably a mixture of water and isopropanol and optionally other excipients preferably emollient(s), preferably octyldecanol and/or penetration enhancer(s), preferably DL-alpha-Tocopherol are homogenized with an HPH homogenizer, preferably 1-125 times, more preferably 3-10 times, most preferably 5-10 times using pressure between 500-2000 bar, preferably between 500-1500 bar, most preferably 1000-1500 bar, then to the thus obtained mixture pregabalin and optionally other excipients, preferably emollient(s), preferably Decylis oleas and preservatives, preferably an aqueous EDTA solution are admixed, then the thus obtained mixture is added to a gel phase prepared by swelling a rheology modifier, preferably polyethylene glycol, synthetic polymers preferably carbomers (polyacrylic acid) more preferably carbomer 980, hydroxyalkyl celluloses, preferably hydroxyethyl cellulose and vegetable gums, preferably xanthan gum or guar gum, most preferably carbomer 980 in a solvent, preferably water and the pH of the gel phase is adjusted with a pH modifier, preferably aqueous ammonium solution if necessary, or the mixture of a phospholipid and a solvent, preferably water or a mixture of water and an alcohol, more preferably ethanol or isopropanol, most preferably a mixture of water and isopropanol and optionally other excipients preferably emollient(s), preferably octyldecanol and/or penetration enhancer(s), preferably DL-alpha-Tocopherol are homogenized with an HPH homogenizer, preferably 1-125 times, more preferably 3-10 times, most preferably 5-10 times using pressure between 500-2000 bar, preferably between 500-1500 bar, most preferably 1000-1500 bar, and the thus obtained mixture is admixed to a mixture of pregabalin and a solvent preferably water and optionally other excipients, preferably emollient(s), preferably decylis oleas and preservatives, preferably an aqueous EDTA solution which mixture has been separately homogenized with an HPH homogenizer 1-125 times, more preferably 3-10 times, most preferably 5-10 times using pressure between 500-2000 bar, preferably between 500-1500 bar, most preferably 1000-1500 bar, then the thus obtained mixture is added to a gel phase prepared by swelling a rheology modifier, preferably polyethylene glycol, synthetic polymers preferably carbomers (polyacrylic acid) more preferably carbomer 980, hydroxyalkyl celluloses, preferably hydroxyethyl cellulose and vegetable gums, preferably xanthan gum or guar gum, most preferably carbomer 980 in a solvent, preferably water and the pH of the gel phase is adjusted with a pH modifier if necessary, preferably aqueous ammonium solution, or the mixture of phospholipid with a solvent, preferably water or a mixture of water and an alcohol, more preferably ethanol or isopropanol, most preferably a mixture of water and isopropanol and optionally other excipients preferably emollient(s), preferably octyldecanol and/or penetration enhancer(s), preferably DL-alpha-Tocopherol are homogenized with an HPH homogenizer, preferably 1-125 times, more preferably 3-10 times, most preferably 5-10 times using pressure between 500-2000 bar, preferably between 500-1500 bar, most preferably 1000-1500 bar, then pregabalin and optionally other excipients preferably emollient(s), preferably Decylis oleas and preservatives, preferably an aqueous EDTA solution, are added to the lipid phase then the thus obtained mixture is homogenized with an HPH homogenizer preferably 1-125 times, more preferably 3-10 times, most preferably 5-10 times using pressure between 500-2000 bar, preferably between 500-1500 bar, most preferably 1000-1500 bar, then the thus obtained mixture is added to a gel phase prepared by swelling a rheology modifier, preferably polyethylene glycol, synthetic polymers preferably carbomers (polyacrylic acid) more preferably carbomer 980), hydroxyalkyl celluloses, preferably hydroxyethyl cellulose and vegetable gums, preferably xanthan gum or guar gum, most preferably carbomer 980 in a solvent, preferably water and the pH of the gel phase is adjusted with a pH modifier if necessary, preferably with aqueous ammonium solution, or a mixture of a phospholipid and a solvent, preferably water or a mixture of water and an alcohol, more preferably ethanol or isopropanol, most preferably a mixture of water and isopropanol and optionally other excipients preferably emollient(s), preferably octyldecanol and/or penetration enhancer(s), preferably DL-alpha-Tocopherol is homogenized with an HPH homogenizer, preferably 1-125 times, more preferably 3-10 times, most preferably 5-10 times using pressure between 500-2000 bar, preferably between 500-1500 bar, most preferably 1000-1500 bar, then the thus obtained mixture is added to a gel phase prepared by swelling a rheology modifier, preferably polyethylene glycol, synthetic polymers, preferably carbomers (polyacrylic acid) more preferably carbomer 980, hydroxyalkyl celluloses, preferably hydroxyethyl cellulose and vegetable gums, preferably xanthan gum or guar gum, most preferably carbomer 980 in a solvent, preferably water and the pH of the gel phase is adjusted with a pH modifier if necessary, preferably with aqueous ammonium solution, then pregabalin and optionally other excipients preferably emollient(s), preferably Decylis oleas and preservatives preferably an aqueous EDTA solution are added to the phospholipid phase then the thus obtained mixture is homogenized with an HPH homogenizer preferably 1-125 times, more preferably 3-10 times, most preferably 5-10 times using pressure between 500-2000 bar, preferably between 500-1500 bar, most preferably 1000-1500 bar, then if necessary a further rheology modifier or excipients are added to the mixture.

According to a preferable embodiment the topical composition of the present invention can be obtained by the process in which the mixture of a phospholipid, pregabalin and a solvent or a mixture of solvents, preferably water or a mixture of water and an alcohol, more preferably a mixture of water and ethanol or isopropanol, most preferably a mixture of water and isopropanol and optionally other excipients, preferably emollient(s), preferably octyldecanol and/or penetration enhancer(s), preferably DL-alpha-Tocopherol is homogenized with an HPH homogenizer preferably 1-125 times, more preferably 3-10 times, most preferably 5-10 times using pressure between 500-2000 bar, preferably between 500-1500 bar, most preferably 1000-1500 bar, then the thus obtained mixture is added to a gel phase prepared by swelling a rheology modifier, preferably poloxamer, polyethylene glycol, synthetic polymers preferably carbomers (polyacrylic acid) more preferably carbomer 980, hydroxyalkyl celluloses, preferably hydroxyethyl cellulose and vegetable gums, preferably xanthan gum or guar gum, most preferably carbomer 980 in a solvent, preferably water and the pH of the gel phase is adjusted with a pH modifier if necessary, preferably with aqueous ammonium solution rheology modifier and optionally other excipients are added to the thus obtained mixture and homogenized, or the mixture of a phospholipid, pregabalin and a solvent or a mixture of solvents, preferably water or a mixture of water and an alcohol, more preferably a mixture of water and ethanol or isopropanol, most preferably a mixture of water and isopropanol and optionally other excipients preferably emollient(s), preferably octyldecanol and/or penetration enhancer(s), preferably DL-alpha-Tocopherol is homogenized with an HPH homogenizer preferably 1-125 times, more preferably 3-10 times, most preferably 5-10 times using pressure between 500-2000 bar, preferably between 500-1500 bar, most preferably 1000-1500 bar, then the thus obtained mixture is added to a gel phase prepared by swelling a rheology modifier, preferably poloxamer, polyethylene glycol, synthetic polymers preferably carbomers (polyacrylic acid) more preferably carbomer 980, hydroxyalkyl celluloses, preferably hydroxyethyl cellulose and vegetable gums, preferably xanthan gum or guar gum, most preferably carbomer 980 in a solvent, preferably water and the pH of the gel phase is adjusted with a pH modifier if necessary, preferably aqueous ammonium solution and the thus obtained composition is homogenized with an HPH homogenizer preferably 1-125 times, more preferably 3-10 times, most preferably 5-10 times using pressure between 500-2000 bar, preferably between 500-1500 bar, most preferably 1000-1500 bar, then if necessary further excipients are added and the thus obtained mixture is homogenized.

The HPH homogenization process is crucial for the preparation of the present invention. During our experimental work, we used a range of pressure between 500-2000 bar, more preferably 500-1500 bar, most preferably 1000-1500 bar.

The process for the homogenization was carried out by EmulsiFlex-C3 homogenizer produced by AVESTIN, Inc. (2450 Don Reid Drive, Ottawa, ON, Canada, K1H 1E1) and followed the instructions of the manufacturer. Essentially, the sample was put into the sample chamber then the homogenizer was set on. Generally, the used pressure of homogenization was 1000-1500 bar, but the procedure can be carried out also at 2000 bar. After the homogenization had finished, the sample was put back to the sample chamber for further homogenization if it was necessary. The homogenization was repeated from 1 to 125 times as mentioned above. In the case when a mixture is homogenized several times, it may be useful to carry out pre-homogenization by using lower homogenizing pressure between 500-800 bar for the first two homogenization steps. The applicable pressure also depends on the geometry of the device, and the applicable pressure can be determined by a person skilled in the art with knowledge of the device.

The process for the preparation of a topical composition can be carried out by using equipment generally used in the pharmaceutical industry. The selection and use of these equipment form part of the knowledge of the person skilled in the art. The optimization of the process for the available equipment is also part of the knowledge of the person skilled in the art. Further information on the used technological steps are generally described e.g. in Encyclopedia of Pharmaceutical Technology, Third Edition, (© 2007 by Informa Healthcare USA, Inc.). Different types of and operational parameters and use of high pressure homogenizers are also fully described in the chapter Homogenization and homogenizers on pages 1996-2003 of Encyclopedia of Pharmaceutical Technology, Third Edition (© 2007 by Informa Healthcare USA, Inc.). Selection, use and optimization of the use of any commercially available different high pressure homogenizer is part of the knowledge of the person skilled in the art.

The batch mixing devices used in the examples of the present invention. If they are carried out in a recirculation device by feeding them from a stirred tank to a high-shear mixer/homogenizer and then feeding the resulting mixture back into a mixing tank, it can be calculated from the amount of the mixture mixed. how long it would take to mix the whole mass at once in the case of batch operation. Multiply this by the number of agitations required to properly homogenize the given composition in the case of batch operation. However, due to the geometry and mixing properties of the storage tank, the experience with homogenization processes is that in such a case, precisely because the already homogenized product mixes with the not yet homogenized material, it usually takes longer to fully homogenize than previously calculated. This is usually 1.5-2 times the time, but it strongly depends on the geometry of the storage tank used and the efficiency of the stirrer used in it, as well as the flow conditions prevailing there. One skilled in the art will be able to transfer the methods of the invention to such devices based on his general knowledge.

According to a more preferable embodiment of the present invention, the composition can be obtained by a process mentioned above by using ground pregabalin as active ingredient. More preferably, micronized pregabalin is used. Thus, the used pregabalin is preferably ground, having a $D_{90}$ of particle size of ground pregabalin between 20-200 micrometer, more preferably the used pregabalin is micronized having a $D_{90}$ of particle size below 20 micrometer.

In the methods of the present invention, pregabalin may be added to the composition either in solid form, as a powder, or even as a suspension during the preparation of the composition.

Taking into consideration that elevation of the temperature changes pregabalin in the solvent and since the HPH homogenization involves heat generation, in preferable embodiments of the present invention the temperature of the mixture of the present invention during the HPH homogenization is kept between 0-50° C., preferably 20-45° C., most preferably 25-35° C.

According to the preferred embodiment of the present invention the phospholipids are swelled before use. Thus, according to the present invention the mixture of the phospholipid is prepared by swelling the phospholipid, preferably lecithin, more preferably soya lecithin, deoiled soya lecithin, lipoid P75, lipoid S75, with 10-30 fold preferably 1-20 fold of weight amount water by the weight of phospholipid and the thus obtained swollen phospholipid is mixed with other excipients to form the lipid phase.

In a preferred embodiment the phospholipid is swelled in 5-25 preferably 10-20 fold water calculated on the weight of the used phospholipid between 25-40° C., preferably between 25-35° C., then the thus obtained swollen mixture is used as phospholipid mixture. The swelling process takes 0.1-24 hours, preferably 0.3-3 hours. In a preferred embodiment this mixture can be directly homogenized with a high pressure homogenizer, or before the high-pressure homogenization other excipients such as emollients and penetration enhancer(s) are added then homogenized by a high pressure homogenizer. According to a further embodiment, the thus obtained swollen phospholipid mixture can be mixed and homogenized with other excipients and pregabalin and the thus obtained mixture is homogenized with a high pressure homogenizer. According to the most preferable embodiment of the present invention the swollen phospholipid mixture is homogenized preferably 1-125 times, more preferably 3-10 times, most preferably 5-10 times with an HPH homogenizer, then added to the gel phase, the thus obtained mixture is mixed with an aqueous dispersion of pregabalin and the thus obtained composition is homogenized preferably 1-125 times, more preferably 3-10 times, most preferably 5-10 times with an HPH homogenizer.

Similarly, preferably the gel phase is also prepared by swelling the gel then the thus swollen gel phase is added to the composition. More particularly, the gel phase is prepared by swelling the rheology modifier, preferably poloxamer polyethylene glycol, synthetic polymers preferably carbomers (polyacrylic acid) more preferably carbomer 980, hydroxyalkyl celluloses, preferably hydroxyethyl cellulose and vegetable gums, preferably xanthan gum or guar gum, most preferably carbomer 980 in a solvent, preferably water in an amount of 10-30 times, preferably 1-20 times of weight amount solvent, preferably water by the weight of rheology modifier and the pH of the gel phase is adjusted with a pH modifier if necessary. The swelling process takes 6-24 hours, preferably 8-12 hours.

In a preferred embodiment the gel phase is prepared by swelling the rheology modifier with 5-25 preferably 10-20 times water calculated on the weight of the used rheology modifier. As rheology modifier polaxomer-polyethylene glycol, synthetic polymers preferably carbomers (polyacrylic acid) and vegetable gums, preferably carbomers, most preferably carbomers (carbomer 980) are used. Optionally, the pH of the thus obtained gelled mixture is neutralized by addition of a pH modifier. In the case of the use of carbomers, most preferably carbomer 980, a basic pH modifier is used. Such pH modifiers e.g. ammonia, ammonium solution, preferably aqueous ammonium solution, alkali or alkali earth metal hydroxides, carbonates, hydro-carbonates, or organic bases, such as primary, secondary or tertiary amines, most preferably aqueous ammonia solution can be used. According to the most preferable procedure carbomer 980 is swelled in tenfold or twentyfold weight of water based on the weight of carbomer at room temperature, for 3-24 hours, preferably 3-12 hours, more preferably 5-8 hours, then the gelled mixture is neutralized with aqueous ammonia solution at room temperature. In the case of use vegetable gums, preferably xanthan gum, the gum is swelled in tenfold or twentyfold weight of water based on the weight of vegetable gum, preferably xanthan gum is swelled at an elevated temperature between 40-100° C., preferably 50-70° C. more preferably at 60° C. then the thus obtained mixture cooled to at room temperature and homogenized. In the case of use hydroxyalkyl cellulose, preferably hydroxyethyl cellulose, the hydroxyalkyl cellulose is swelled in tenfold or twentyfold weight of water based on the weight of hydroxyalkyl cellulose, preferably hydroxyethyl cellulose is swelled at elevated temperature between 35-40° C., at 37° C. then the thus obtained mixture cooled to at room temperature (25° C.) and homogenized.

In the case of use poloxamer, preferably poloxamer 407 the poloxamer is swelled in water then kept in refrigerator between 5-10° C. for 24 hours, then it is let to warm et room temperature.

The thus obtained neutralized gel can be added either to the mixture comprising phospholipid before or after the HPH homogenization. Or, the thus obtained gelled mixture can be mixed with pregabalin or a mixture comprising pregabalin before or after a HPH homogenization process, or the gelled mixture can be added to a mixture which comprises phospholipid and pregabalin either before or after the high pressure homogenization step.

The topical pharmaceutical composition according to the present invention can be used for the treatment of neuropathic pain, in peripheral neuropathic pain, such as the pain experienced by diabetic patients or by patients who have had herpes zoster (shingles), and central neuropathic pain, such as the pain experienced by patients who have had a spinal-cord injury; diabetic neuropathy, causalgia, brachial plexus avulsion, occipital neuralgia, reflex sympathetic dystrophy, fibromyalgia, gout, phantom limb pain, burn pain, and other forms of neuralgic, neuropathic, and idiopathic pain syndromes, preferably for the treatment neuropathy, diabetic neuropathy, peripheral neuropathic pain, post herpetic pain.

According to the present invention in the composition the phospholipids are dispersed and solid pregabalin particles are also dispersed. The dispersed phospholipid is an emulsion. The composition is formed to a gel, cream or gel-cream form by adding the rheology modifier. The solid form of pregabalin can be either crystalline or amorphous.

The advantage of the present invention over the prior art compositions resides in that the topical pharmaceutical composition according to the present invention has a long-lasting pain alleviating effect, at least 5 or 8 hours without serious systemic effects. It can be used on a large surface of the body which is very important in the case of the treatment of neuropathic pain.

A further advantage of the present invention is that the compositions obtained have long shelf life. The compositions are stable at room temperature for even more than 1 year. It is surprising that the effect of the HPH homogenization persists for a long time.

There is no severe systemic effect of the composition which is very important in the case of treatment of Diabetic neuropathy (DPN) in which the affected body surface can reach about 28% of the body surface.

The composition obtained by the present invention lets the patients having neuropathic pain achieve an eight-hour sleeping period.

BRIEF DESCRIPTION OF THE DRAWINGS

PGA 2180719 (pregabalin 2.5%, 50 μl/right paw, Values are mean±S.E.M. n=6), both paw PGA 2190719 (pregabalin 5%, 20 μl/right paw, Values are mean±S.E.M. n=7), both paw PGA 0450717 (pregabalin 15%, 50 μl/right paw, Values are mean±S.E.M.), both paw PGA 0470717 (pregabalin 15%, 50 μl/right paw, Values are mean±S.E.M.), both paw PGA 1601018 (pregabalin 5%, 20 µl/right paw, Values are mean±S.E.M.), both paw PGA 1601018 (pregabalin 5%, 20 µl/right paw, Values are mean±S.E.M.), MPN litigated paw PGA 0591017 (pregabalin 15%, 50 µl/right foot, mean±S.E.M.), both feet

PGA 0980418 (pregabalin 15%, 20 µl/right paw, Values are mean±S.E.M.), both paw

PGA 0990418 (pregabalin 15%, 20 µl/right paw, Values are mean±S.E.M.), both paw

PGA 1000418 (pregabalin 15%, 20 µl/right paw, Values are mean±S.E.M.), both paw

PGA 1040418 (pregabalin 15%, 20 µl/right paw, Values are mean±S.E.M.), both paw

Figure 3:
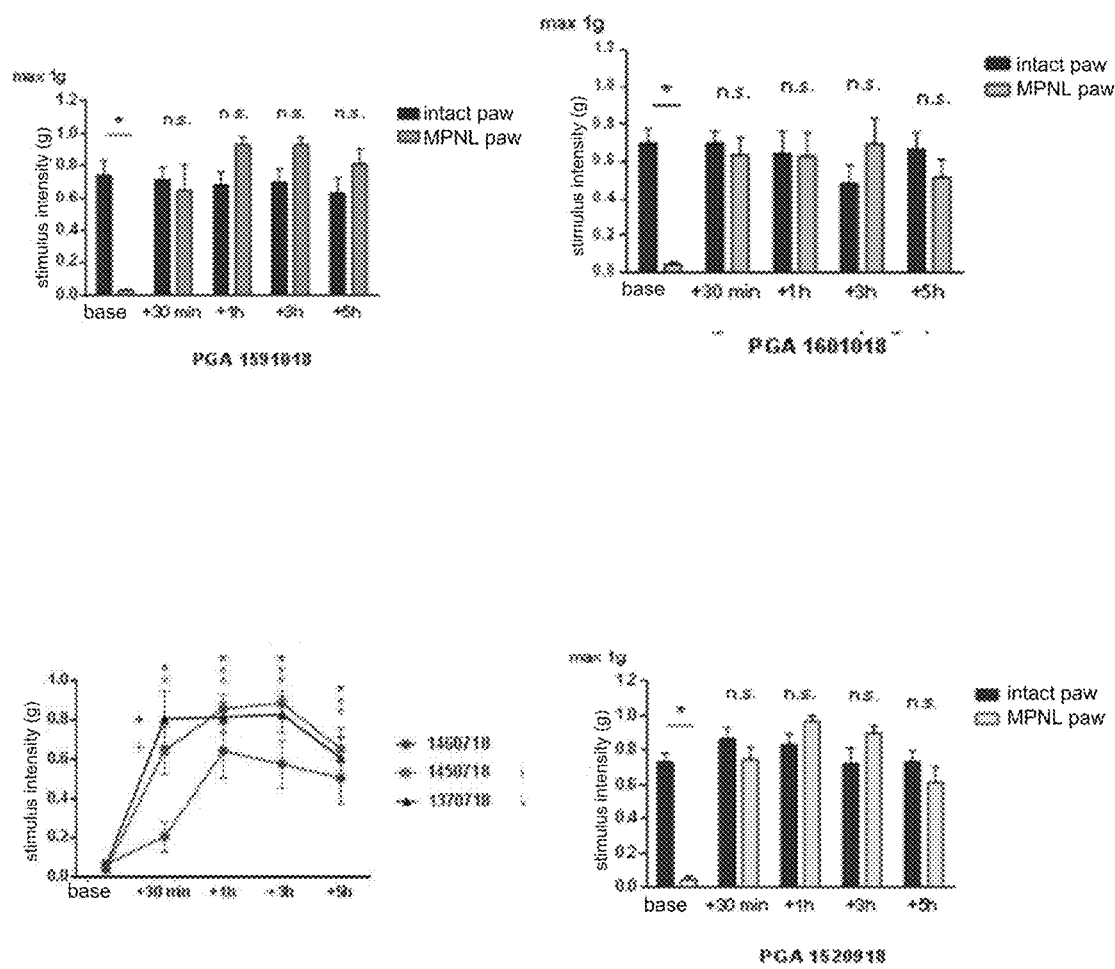

PGA 1040418 (pregabalin 15%, 20 µl/right paw, Values are mean±S.E.M.), MPN litigated paw PGA 1510918 (pregabalin 10%, 20 µl/right paw, Values are mean±S.E.M.), both paw PGA 1510918 (pregabalin 10%, 20 µl/right paw, Values are mean±S.E.M.), MPN litigated paw PGA 1520918 (pregabalin 37.5%, 20 ul/right foot, mean±S.E.M.), both feet FIG. 3: Plantar withdrawal threshold diagrams 7 days after MPNL surgery in NMRI mice:

PGA 1591018 (pregabalin 10%, 20 µl/right paw, Values are mean±S.E.M.), both paw

PGA 1601018 (pregabalin 5%, 20 µl/right paw, Values are mean±S.E.M.), both paw

PGA 1520918 (pregabalin 37.5%, 20 µl/right paw, Values are mean±S.E.M.), both paw Comparative plantar withdrawal threshold diagrams 7 days after MPNL surgery in NMRI mice:

Comparison of effects of PGA1460718 (5%), PGA1450718 (10%), PGA1370718 (15%)

(20 µl/right paw, Values are mean±S.E.M.), MPN litigated paw

Figure 4:
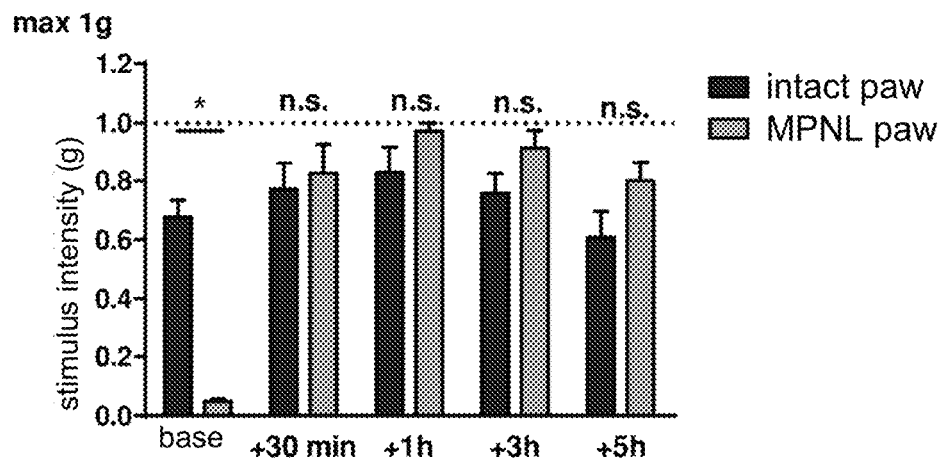
Figure 4:
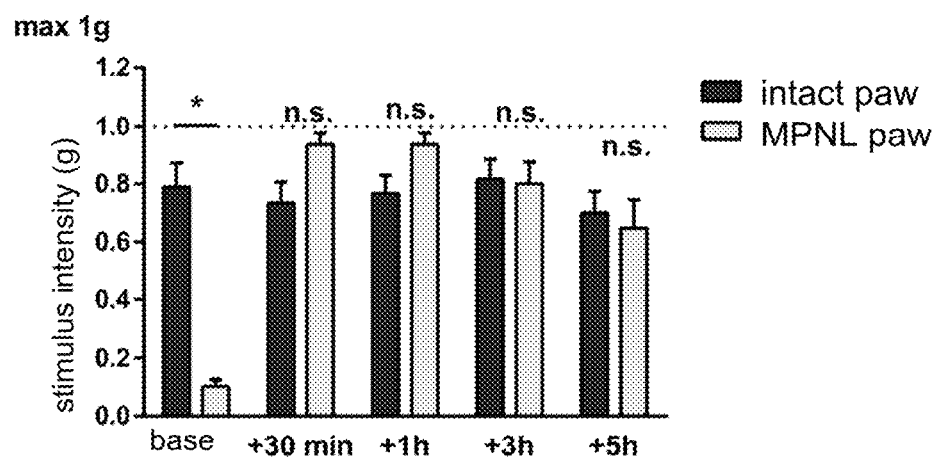
Figure 5:
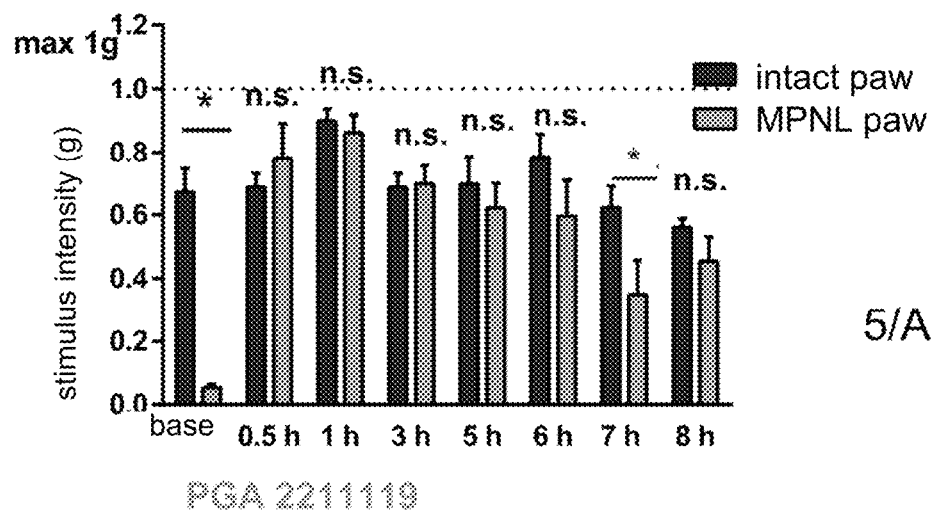
Figure 5:
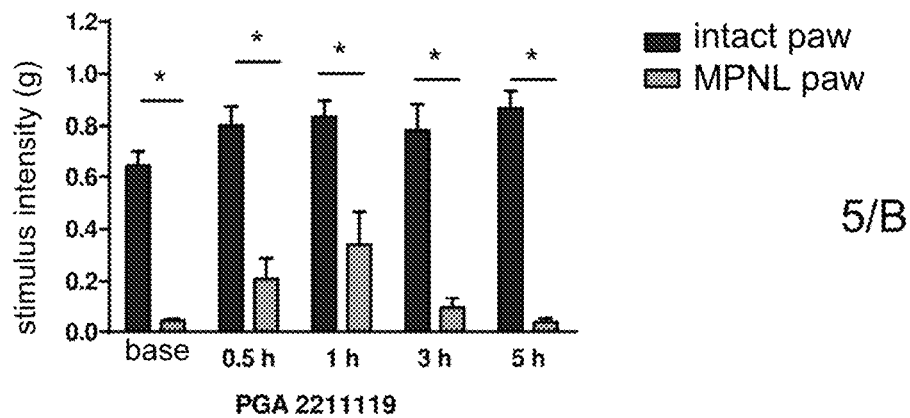
Figure 6:
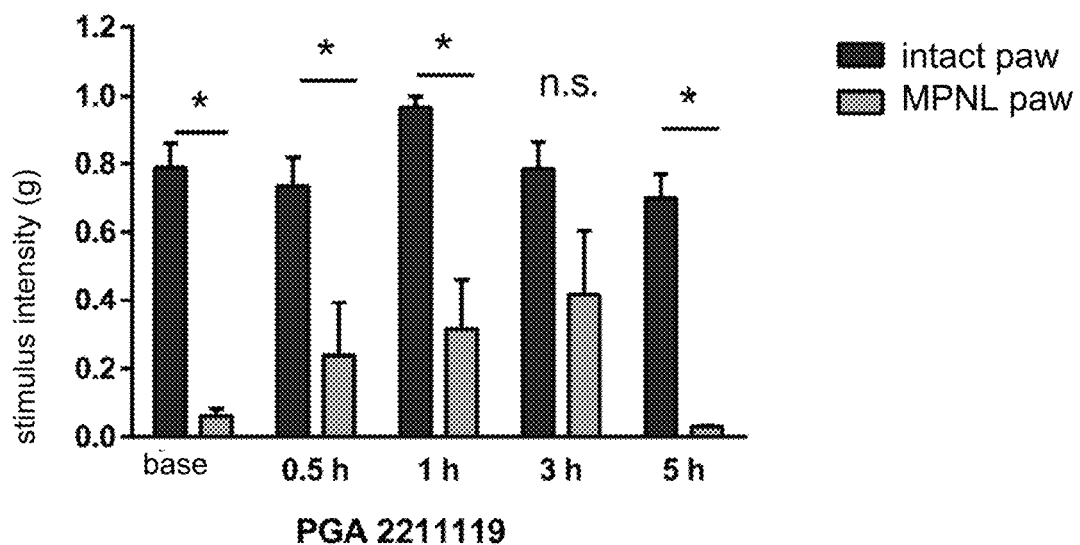
Figure 7:
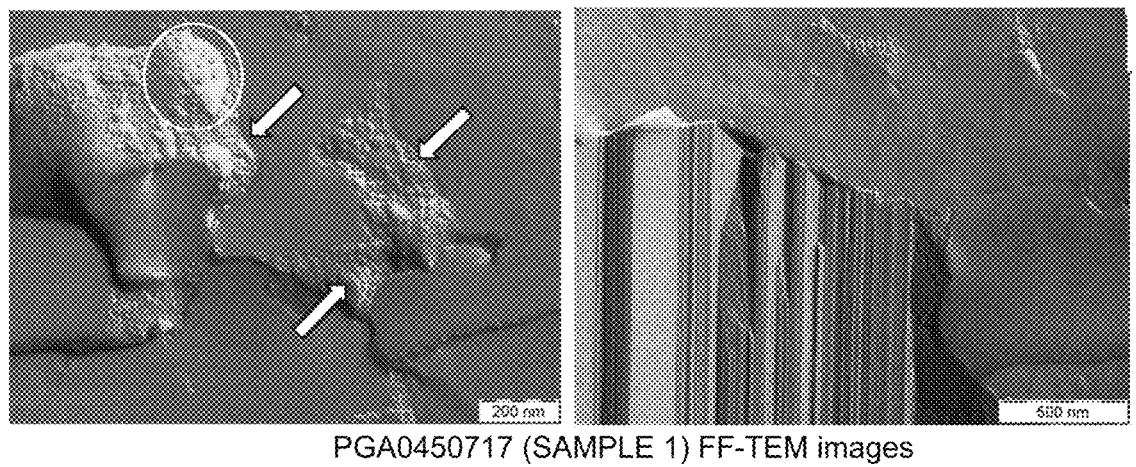
Figure 7:
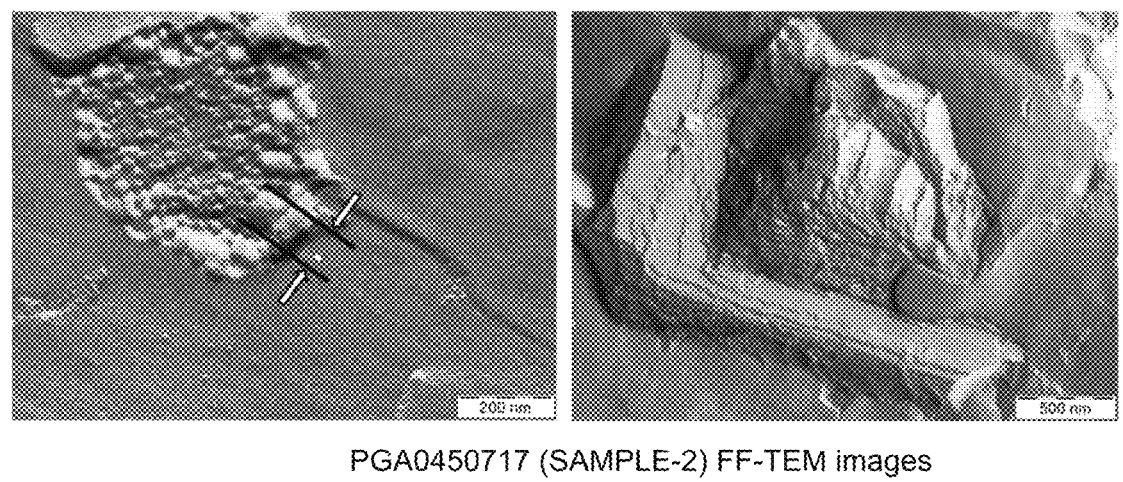

FIG. 4: Plantar withdrawal threshold diagrams 7 days after MPNL surgery in NMRI mice:

PGA 2211119 (pregabalin 5%, 20 µl/right paw, Values are mean±S.E.M. n=7), both paw PGA 2150619 (pregabalin 5%, 20 µl/right paw, Values are mean±S.E.M. n=6), both paw FIG. 5: Plantar withdrawal threshold diagrams 7 days after MPNL surgery in NMRI mice:

PGA 2211119 (pregabalin 5%, 20 µl/right paw, Values are mean±S.E.M. n=8), both paw PGA 2211119 (pregabalin 5%, 50 µl/2 cm² on skin of the upper part of the back towards the neck, Values are mean±S.E.M. n=8), both paw FIG. 6: Plantar withdrawal threshold diagrams 7 days after MPNL surgery in NMRI mice:

PGA 2211119 (pregabalin 5%, 50 µl/6 cm² on skin of the upper part of the back towards the neck, Values are mean±S.E.M.), both paw FIG. 7: FTEM test pictures of PGA0470717 and PGA0450717

Figure 8:
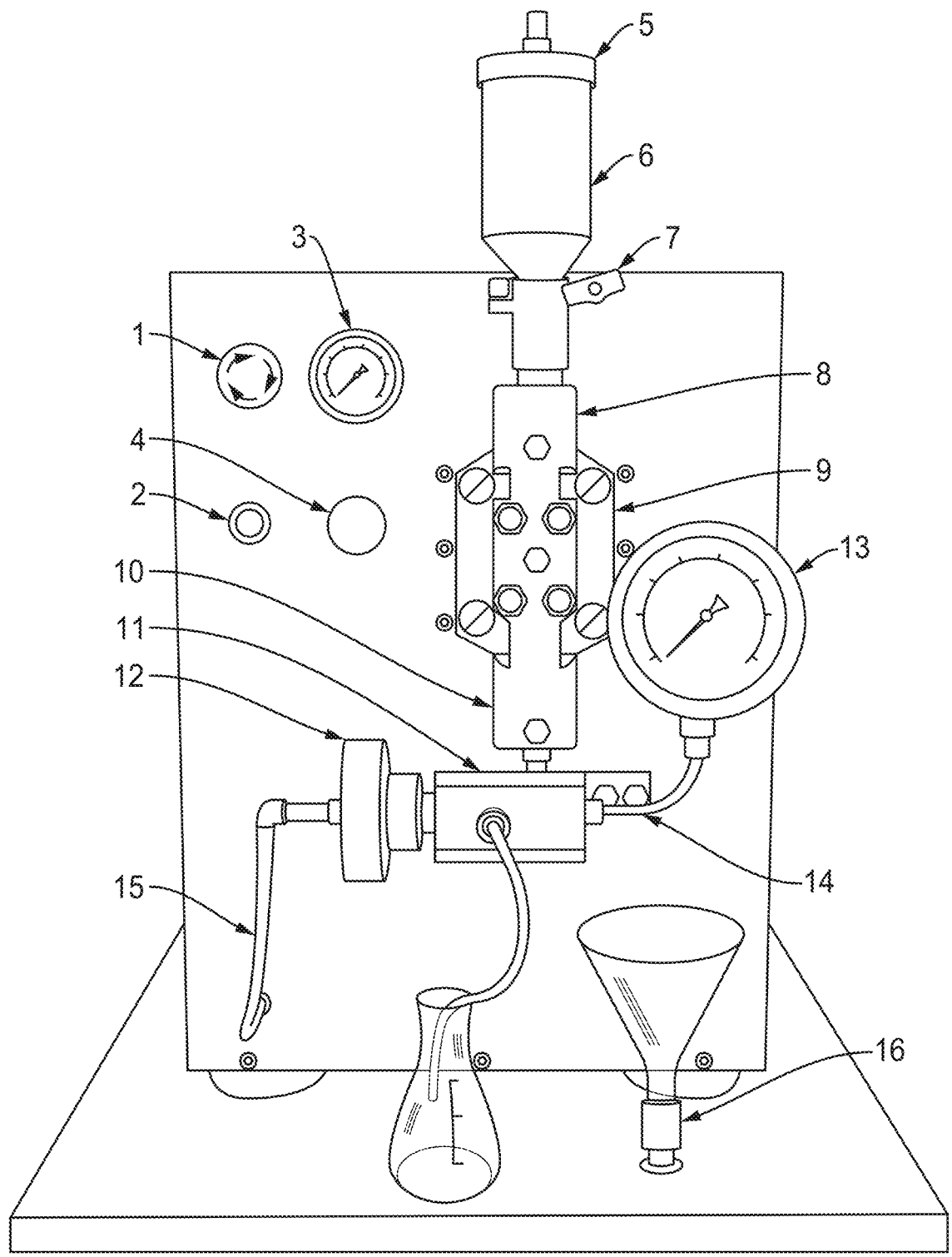

FIG. 8: EmulsiFlex-C3 type high pressure homogenizer.

Figure 9:
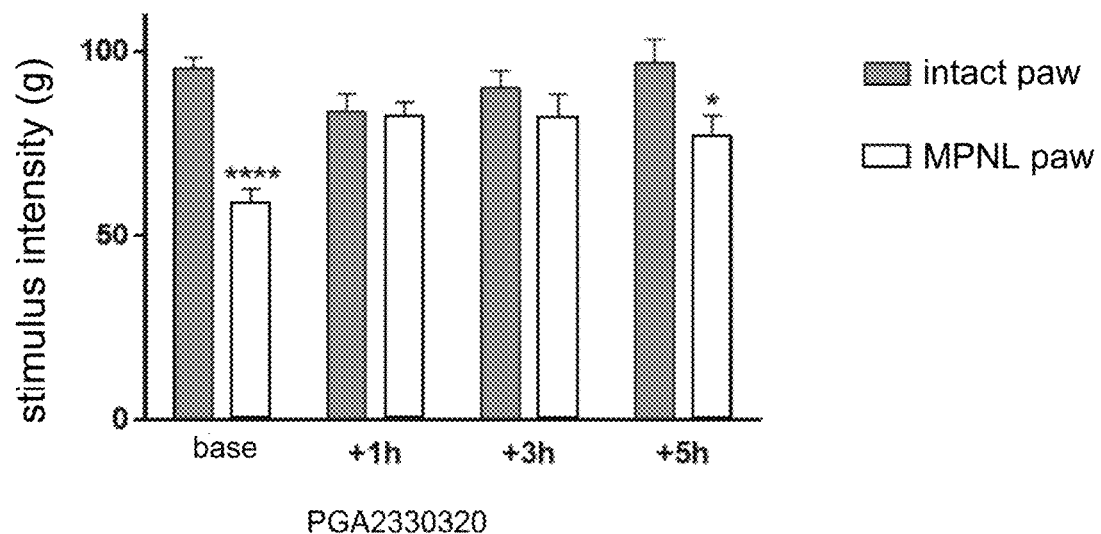

FIG. 9: Plantar withdrawal threshold diagrams 21 days after CCI surgery in rats (5 mg pregabalin/4 cm² in 50 µl 10% cream) Values are mean±S.E.M., n=15 two-way Bonferroni's ****p<0.0001) (example 3).

Figure 10:
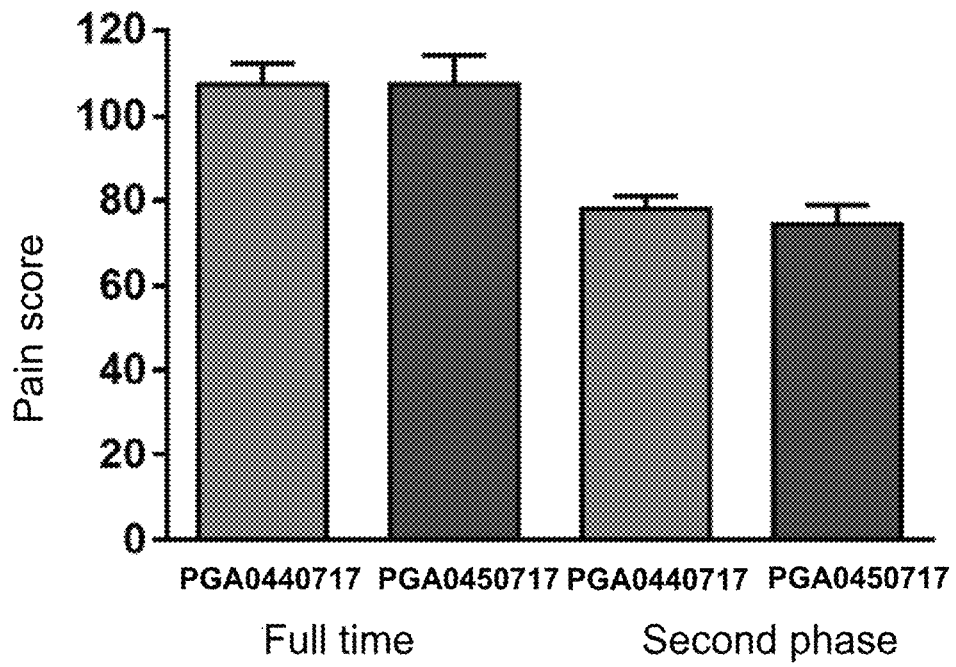
Figure 10:
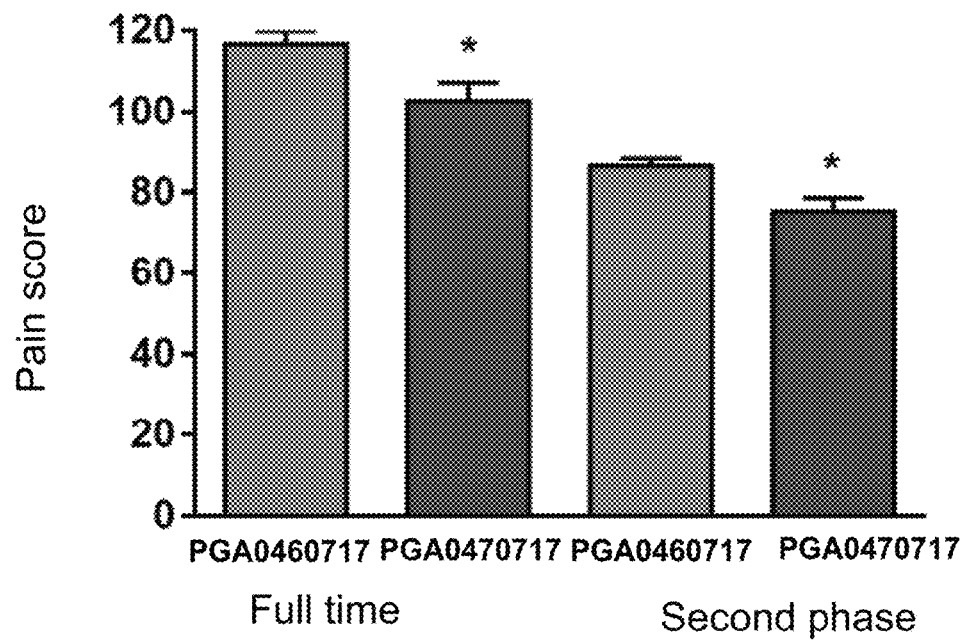

FIG. 10: Figure results of formalin test of neuropathic pain in rats

FIG. 10/A Mean values±S.E.M. of Sum of pain score of P-1 (PGA0440717) placebo composition used in 0.1 ml/paw and R-3 (PGA0450717) reference gel 0.1 ml/paw, in the total time of the test and the second phase (from 16 to 45 min) of the test.

FIG. 10/B Mean values±S.E.M. of Sum of pain score of P-2 (PGA0460717) placebo composition used in 0.1 ml/paw and WE-1 (PGA0470717) reference gel 0.1 ml/paw, in the total time of the test and the second phase (from 16 to 45 min) of the test.

Figure 11:
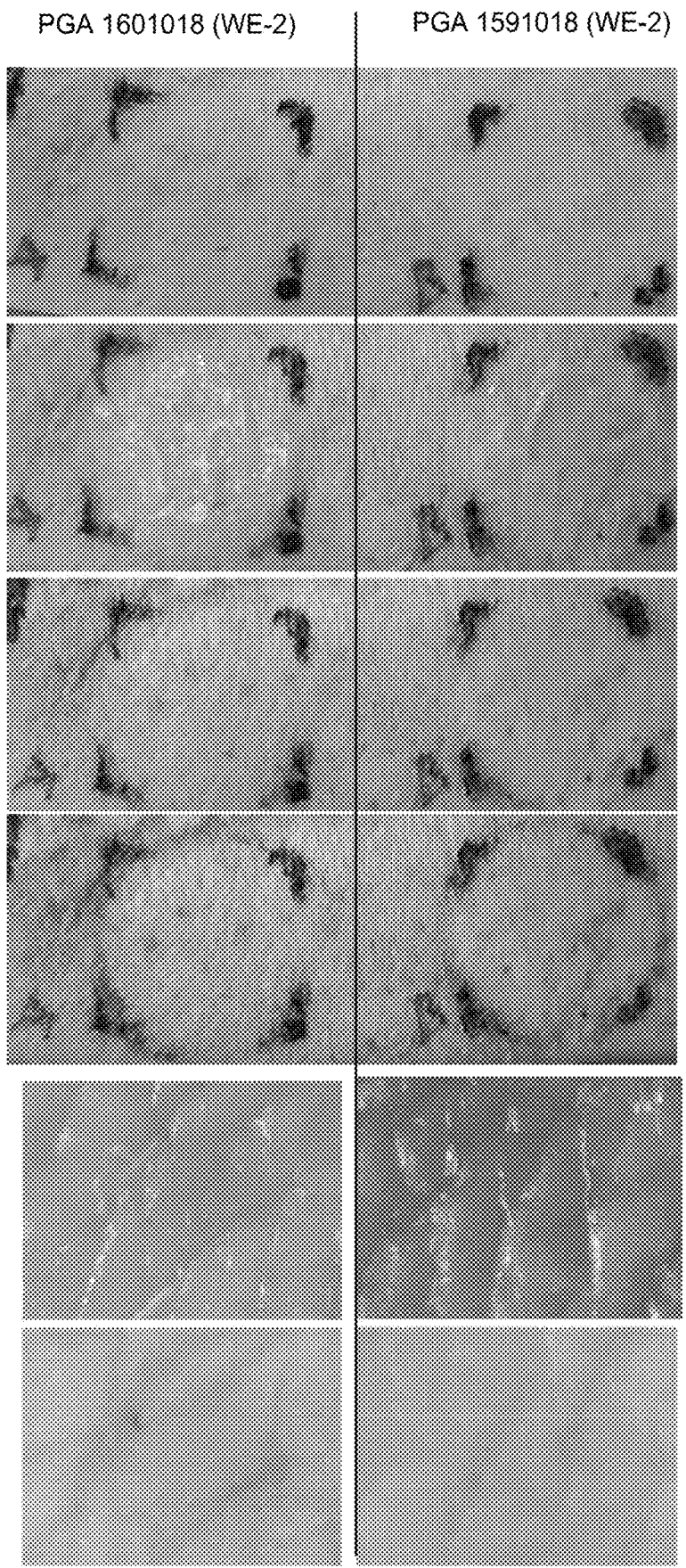

FIG. 11 Absorption of pregabalin cream from the surface of topically treated ex vivo pig skin 11/a.: Photo of the surface of the pig skin before the treatment.

11/b.: Photo of the surface of the pig skin immediately after the treatment with gel comprising 5% pregabalin (PGA 1601018 (WE-2) left side) and a gel comprising 10% of pregabalin (PGA 1591018 (WE-2) right side).

11/c.: Photo of the surface of the pig skin 1 hour after the treatment with gel (PGA 1601018 (WE-2) left side) and (PGA 1591018 (WE-2) right side).

11/d.: Photo of the surface of the pig skin 3 hours after the treatment with gel (PGA 1601018 (WE-2) left side) and (PGA 1591018 (WE-2) right side).

11/e.: Microscopic picture (1:10) of the surface of the pig skin before the treatment.

11/f.: Microscopic picture (1:10) of the surface of the pig skin 2 hours after the treatment with gel (PGA 1601018 (WE-2) left side) and (PGA 1591018 (WE-2) right side).

Figure 12:
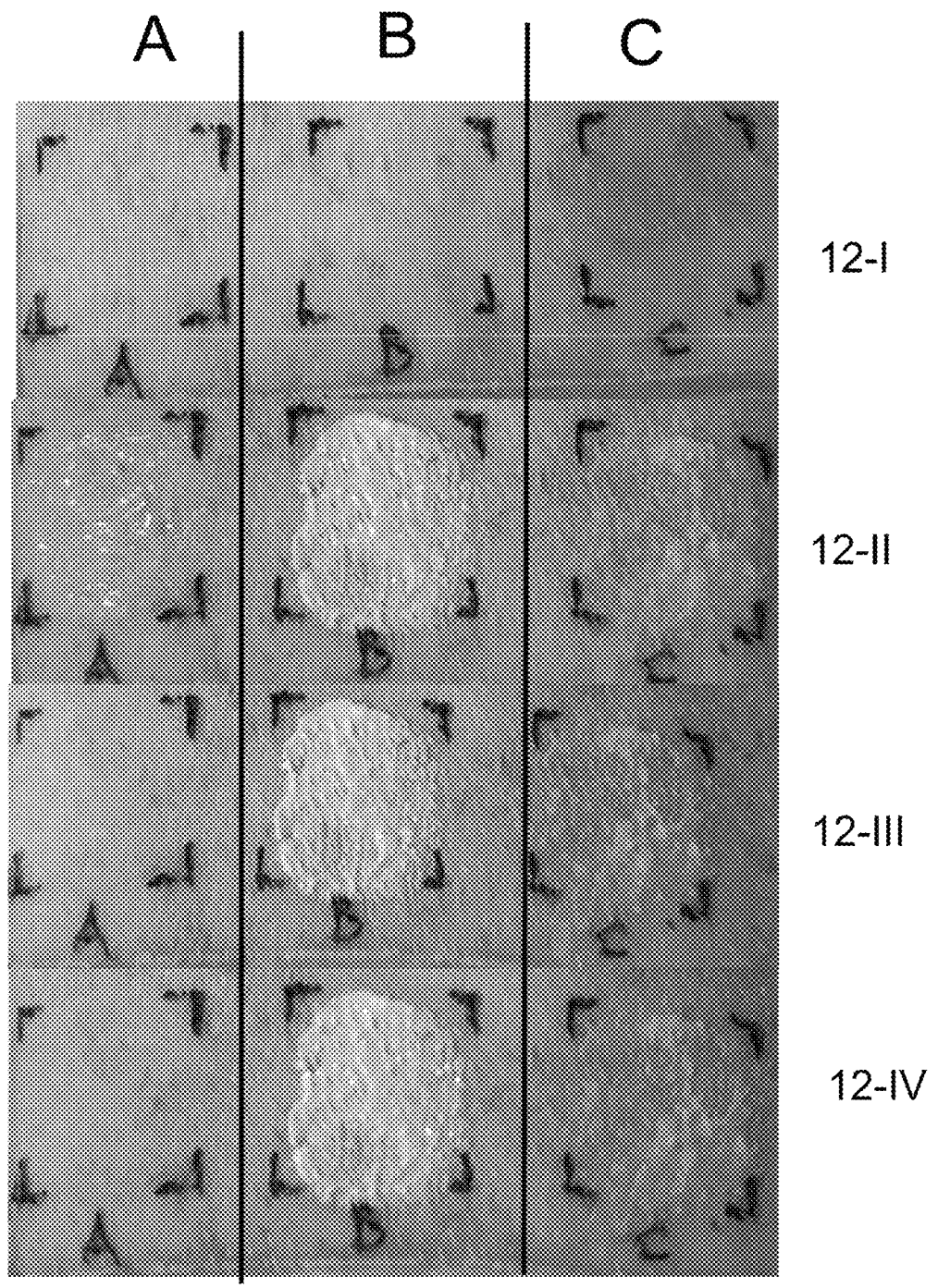

FIG. 12. Absorption of pregabalin cream compared to Neogramornon® and Mometasone Medimer® from topically treated ex vivo porcine skin 12-I: Photo of the surface of the pig skin before the treatment.

12-II: Photo of the surface of the pig skin immediately after the treatment with gel comprising 5% pregabalin (PGA 1671118 left side, A column), Neogramornon® (B column) and Mometasone Medimer® (C column)

12-III: Photo of the surface of the pig skin one hour after the treatment with gel comprising 5% pregabalin (PGA 1671118 left side, A column), Neogramornon® (B column) and Mometasone Medimer® (C column)

12-IV: Photo of the surface of the pig skin three hours after the treatment with gel comprising 5% pregabalin (PGA 1671118 left side, A column), Neogramornon® (B column) and Mometasone Medimer® (C column)

Figure 13:
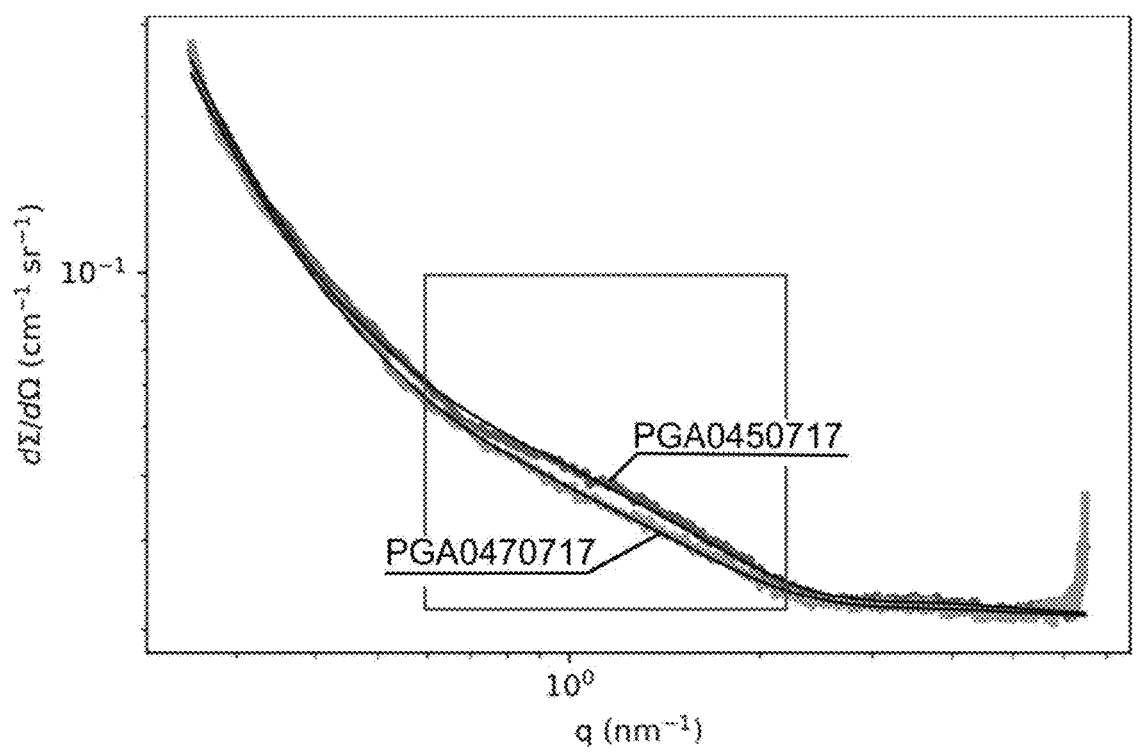

FIG. 13: SAXS curves of samples PGA0450717, PGA0470717 and curves of fitted functions.

Figure 14A:
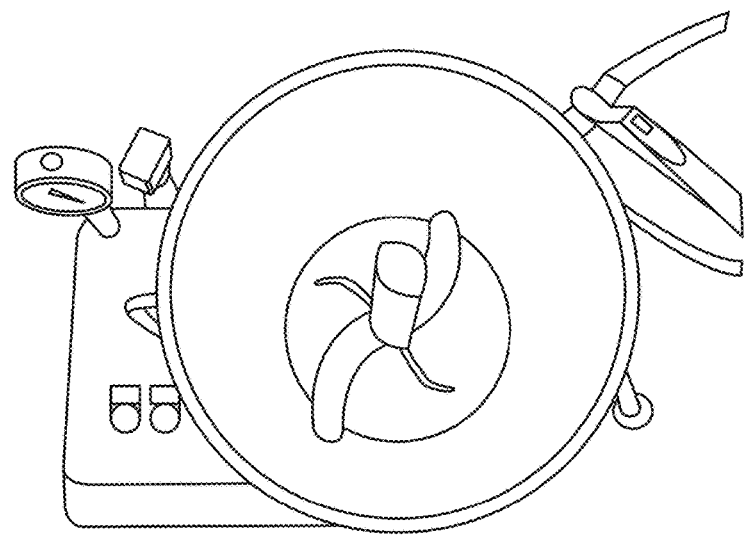
Figure 14B:
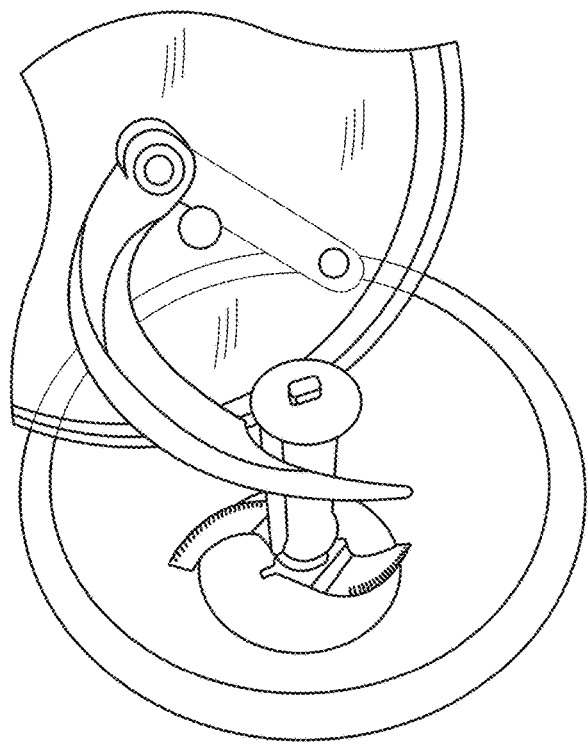
Figure 14C:
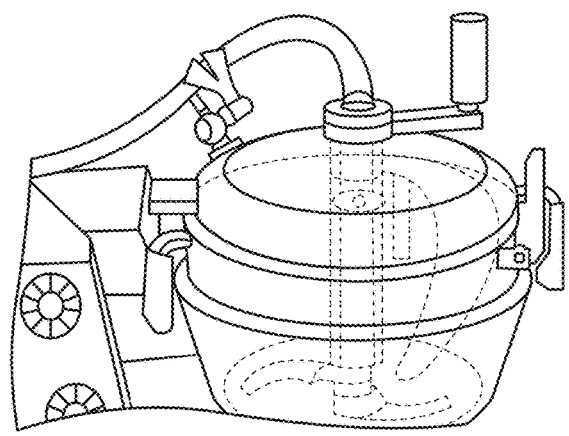

FIG. 14: Stephan UMC 5 electronic homogenizer, 14/A top view, 14/B top view with scraper knife and 14/C schematic drawing.

Our invention is illustrated in a more detailed manner by the following examples without limiting the scope of our invention to these examples:

Example 1

Mouse Model of Neuropathic Pain
Animals

The experiments were performed in NMRI male mice (Toxi-Coop Ltd). The initial weight of animals was between 25-35 g. All animals were housed in plastic cages, under standard laboratory conditions (24±2° C. room temperature, 40-60% relative humidity) with free access to standard laboratory pellet for mice and tap water. They were kept on a 12-hours light/dark cycle with light onset at 06:00 AM. Animals were transferred to the testing room at least 1 hour before the experiments and they were used only once. The animal care and testing procedures were done in accordance with the Directive 2010/63/EU of the European Parliament and with the Hungarian 1998. XXVIII. Act on the Protection Welfare of Animals.

Method

Medial Plantar Nerve Ligation (MPNL) Model

Under chloral hydrate anaesthesia (400 mg/kg i.p.), the skin on the medial surface of the right ankle of mice were incised (in a length of 0.5 cm) to expose the medial plantar nerve. After exposure of the nerve, two ligations on this nerve were performed with a 5-0 thread (Seralon, SERAG-WIESSNER, Germany). The ligations were tied in a way as to be bound tightly to the nerve without throttling them. Then a 4-0 silk thread was used to close the wound.

Nociceptive Test

A week after the medial plantar nerve ligation, animals were placed one by one into small (12×12×15 cm) plastic cages with wire grid floor. The cages were elevated and were illuminated from below. After an at least 30 minute long habituation period the base plantar withdrawal thresholds (PWT) were evaluated on the left and right hind paws using von Frey filaments (Touch-Test Sensory Evaluators, North Coast Medical Inc. USA). Briefly, a set of 8 calibrated monofilaments that provide an approximately logarithmic scale of actual force (von Frey filament sizes: 0.008, 0.02, 0.04, 0.07, 0.16, 0.4, 0.6 and 1.0 g) were applied to determine the threshold stiffness of the filament that was required to elicit a paw withdrawal response. First, for baseline determination three measurements were done using ascending series of filaments, then two measurements were done at the following time points. Animals which did not show mechanical allodynia at the baseline measurement were excluded from the test. After the baseline measurement the test material was administered either topically, intraperitoneally or per os. The PWT measurements were repeated on each hind paw at 0.5, 1, 3 and 5 (6, 7, 8 at longer experiments) hours after the administration of test material.

Measured Parameter

Von Frey filament size which induced the paw withdrawal behaviour. The plantar withdrawal threshold is the mean of the withdrawal behaviour inducing filament sizes/time point expressed in grams.

Statistical Analysis

Two-way ANOVA followed by Bonferroni's post hoc tests were used for comparing the PWT-values for both sides at all time points. Repeated measured one-way ANOVA followed by Dunnett's tests were used to compare the PWT data for one side (vs base). $P<0.05$ was considered as significant.

Example 2

Investigation of Systemic Effect Topical Compositions Used in Mouse Model of Neuropathic Pain Method:

Our studies were performed in a mouse model of neuropathy (according to example 1) in which neuropathic symptoms were developed surgically on the right hind leg (medial plantar nerve ligation, MPNL). Mechanical hypersensitivity characteristic of neuropathy developed within one week as a result of surgery. The sensitivity of the operated, right sole increases, which can be verified with von Frey fibers. The fibers can be used to determine the plantar withdrawal threshold (PWT) on both hind legs. After determining the base sensitivity of the hind soles, we treated the selected area—left leg or the upper part of the back towards the neck (massage, for a maximum of 1 minute).

After treatment: at ½, 1, 3, and 5 h, the lifting thresholds of the two hind feet were determined again.

Example 3

Effect of Topical Pregabalin Cream in Rat Model of Neuropathy

Animals

The animals were housed in plastic cages, under standard laboratory conditions (24±2° C., 40-60% relative humidity) with free access to standard laboratory pellet for rats and tap water. They were kept on a 12-hours light/dark cycle with light onset at 06:00 AM Method Chronic Constriction Injury (CCI) Model:

Experimentally induced peripheral neuropathy was performed by the procedure described by Bennett and Xie (Bennett G J, Xie Y K. Pain., A peripheral mononeuropathy in rat that produces disorders of pain sensation like those seen in man. 1988 April; 33(1):87-107). Briefly, under isoflurane anesthesia small blunt dissection was made into the skin of rat right thigh then three loosely constrictive ligatures were placed around common sciatic nerve (chronic constriction injury CCI). Three weeks following nerve injury rats were assessed for hind paw mechanical withdrawal thresholds. The paw withdrawal threshold (PWT) was determined with an Electronic von Frey device according to the modified up-down method of Dixon (Efficient analysis of experimental observations., Annu Rev Pharmacol Toxicol. 1980; 20:441-62). At least 20 g difference should be existed between left and operated right PWT. The animals showing the absence of significant difference between left and operated right PWT were excluded from the experiments.

Different doses of topical pregabalin formulations were used to assess the amelioration of hypersensitivity caused by CCI induced neuropathic pain.

Results:

Significant reduction in PWT (paw withdrawal threshold) was measured following CCI induced neuropathy (base). After administration of 50 µl, 10% pregabalin cream (PGA2330320) no significant differences could be detected between intact and injured paws.

The dose was: 5 mg pregabalin/4 cm2 in 50 µl 10% cream.

Data for FIG. 9: Foot withdrawal thresholds 21 days after CCI surgery in rats (5 mg pregabalin/4 cm$^2$, 50 µl 10% cream) mean±SEM, n=15 for both feet (two-way ANOVA, Bonferroni's * $p<0.05$, **** $p<0.0001$)

| PGA2330320 T | Intact leg Average | Intact leg SEM | CCI operated leg Average | CCI operated leg SEM | number of rats n |
|---|---|---|---|---|---|
| Base | 95.17 | 3.04 | 58.35 | 4.29 | 15 |
| +1 h | 83.50 | 4.62 | 81.67 | 4.28 | 15 |
| +3 h | 89.61 | 5.07 | 81.76 | 6.32 | 15 |
| +5 h | 96.79 | 6.39 | 76.57 | 5.66 | 15 |

Although oral administration of 16.66 mg/kg resulted in relatively high blood levels based on pharmacokinetic studies, this amount of pregabalin was not able to reduce hypersensitivity. (Topical pregabalin does not reduce hypersensitivity systemically with high blood levels. It has local effect.)

Example 4

Effect of Topical Application of Pregabalin Cream in a Rat Model of Formalin-Induced Neuropathy
Method:

As a result of injection of formalin injected into the hind paw of the rat we found a two-phase pain response in the animals, which is scored based on their behavior: the first phase is the direct tissue damage of formalin, which is approximately lasts for 10 minutes, and after a short rest period (5 minutes) the animal experiences a second severe pain due to the inflammation in the leg, which can take up to 1-1.5 hours. The test was developed to test for non-steroidal anti-inflammatory drugs (NSAIDs), in which NSAIDs mainly inhibit the second phase, but the test has also been shown to test drugs for the treatment of neuropathic pain. (A Ellis: The rat formalin test: Can it predict neuropathic pain treatments? Proceedings of Measuring Behavior 2008.).

Animals:

Our experiments were performed on male Wistar rats weighing 240-300 g.

Experiment:

0.1 ml of test composition was applied to the right hind paw of the animals and the animals' feet were wrapped with Folpack (occlusive treatment). After treatment, the rats were placed in an 18 cm diameter, 40 cm high glass measuring cylinder suitable for observing their behavior. After 55 minutes, the Folpack of the legs was removed and returned to the measuring cylinder. After another 5 minutes, 0.05 ml of a 1% formalin solution was injected subcutaneously into the plantar surface of the treated (right hind) legs.

We began to observe the painful behavior of the animals immediately and every minute for 45 min. For each minute, the score for the most severe pain behavior of the period was determined based on the following criteria:

0 points: tolerates own weight on the paw injected with formalin,
1 point: has less load on the injected foot, just relaxes the foot, keeps the weight on the opposite side, limbs while moving,
2 points: keeps the treated foot raised that does not come into contact with the base,
3 points: lick, bite, shake the injected foot.

The scores obtained in this way were evaluated in two ways: the points experienced in 45 minutes were added together (total time), and the data were summed between 16 and 45 minutes (phase 2). Statistical evaluation was performed using Student's t-test.

Measurement:

The P-1 placebo gel (PGA0440717) and the R-3 (PGA0450717) reference composition containing 15% pregabalin were compared according to the above protocol. Both compositions were tested in groups of 8-8 rats by treating each animal with 0.1 ml of P-1 placebo composition or 0.1 ml of R-3 gel.

We also compared the placebo composition P-2 (PGA0460717) according to the above protocol with the composition of the present invention prepared by the WE-1 method (PGA0450717) containing 15% pregabalin. Both compositions were tested in groups of 8-8 rats by treating each animal with 0.1 ml of P-2 placebo gel or 0.1 ml of WE-1 gel.

Results:

FIG. 10/A shows a comparison of the effect of a placebo and a reference compositions prepared by simple mixing: P-1 placebo composition (PGA0440717) and R-3 (PGA0450717) reference composition were measured throughout the whole experiment and in the second phase, which is a graphical representation of the mean values±S.E.M. shows no significant difference compared to the Student's test, either full time of the experiment or in the second phase, i.e., the composition comprising 15% of pregabalin did not show a significant effect compared to placebo.

FIG. 10/B shows a comparison of a placebo formulation with a formulation of the present invention in which the lipid phase was subjected to HPH agitation during formulation:

FIG. 10/B is a graphical representation of the results of the P-2 placebo composition (PGA0460717) and WE-1 (PGA0470717) composition experiments. The FIG. 10/B shows the mean values±S.E.M. Compared with the Student's test, the behavior of the mice was significantly different in both the full-time and the second, i.e., the formulation containing 15% pregabalin significantly reduced pain in this model than the placebo.

This clearly shows that in the treatment of neuropathic pain, the pregabalin content alone is low, it is necessary according to the present invention to subject the lipid phase of the gel, cream or gel cream to intensive mixing, preferably homogenization with an HPH homogenizer. Such intense mixing causes some structural change in the formulation, which significantly enhances the therapeutic effect of the formulation.

Example 5

Absorption of Pregabalin Cream from the Surface of Topically Treated Ex Vivo Pig Skin
Method:

During the formulations we have examined in a quick test to observe the absorption from skin surface. Frozen, full thickness ex vivo pig skin were used for the test. Thawed skin pieces were placed on paper towels soaked with HBSS solution pH 7.0 and warmed on 32° C. for 30 min. on heating pad then 12 µl/cm$^2$ of the examined composition was applied and smeared by finger on 2×2 cm skin surface (treated area:4 cm$^2$). Photos were taken by normal camera and microscope in different time point before and after treatment to visually examine the absorption of the pregabalin formulations from the skin surface. Skins were kept on heating pad (32° C.) during the study.

Results:

5.a.: Checking of absorption of PGA 1601018 comprising 5% of pregabaline and PGA 1591018 comprising 10% of pregabalin shows that one hours after the treatment the gels seemed to be absorbed fully in both cases even the gel comprises pregabaline in a dispersed, solid particles of pregabalin. On FIG. 11 there are photos of the surface of pig skin before, immediately after one hour after and three hours after the treatment. After one hour even the gel comprising 10% of pregabaline seemed to be absorbed fully.

5.b: Comparison of the composition of the present invention PGA1671118 (WE-2 process) with other marketed creams comprising dispersed particles, namely with Neogranormone® and more advanced form of Mometasone Medimer®.

Formulations tested: 5% Pregabalin—PGA1671118
Neogranormone®—0700818 (2023/08) (older formulation)
Mometasone Medimer®—L02 (05-2019) (newer formulation)

Results: A (PGA1671118) was compared to (Neogranormone) having an old marketing authorization and another suspension product (Mometasone). The formulation of the present invention (PGA1671118) was already "absorbed" after 1 hour, while the other two formulations were still visible on porcine skin after 3 hours. After 3 hours, there was no deposition or crystallization visible under magnification for PGA1671118. Photos from the experiment are shown in FIG. 12.

Example 6

HPH Homogenizer and Process for Homogenization

HPH homogenization steps were carried out with a commercially available HPH homogenizer as follows:
Equipment type: EmulsiFlex-C3 (FIG. 8)
Equipment manufacturer: AVESTIN, Inc.
2450 Don Reid Drive, Ottawa, ON, Canada, K1H 1E1,
Specifications
Compressed air: 4-6 bar
Homogenizing machine: internal surface less than 1 dm$^2$
Filling volume: max. 3 l/h
min. 10 ml
Max. Permissible overpressure: 30,000 PSI/2000 bar
Max. Permissible air pressure 125 PSI/0.9 MPa
Max. Permissible operating temperature: 70° C.
Steam sterilized: 121° C.
Refrigerant supply: heat exchanger via glycol, cooling thermostat connected to cold water tap with peristaltic pump Process for the homogenization followed the instructions of manufacturer.

Essentially the sample was put into the sample chamber then the homogenizer was set on.

Then the air pressure was put on. The used pressure of homogenization was 500-1500 bar.

After the homogenization had finished the sample was put back to the sample chamber for further homogenization if it was necessary. The homogenization was repeated from 1 to 125 times.

In the case the mixture is homogenized several times, it may be useful to carry out a pre-homogenization by using lower homogenizing pressure between 500-1000 bar for the first two homogenization steps.

Example 7

Particle Size Analysis of Pregabalin
4.a. PSD Method Description for Non-Micronized Pregabalin
Dry dispersion laser diffraction particle size distribution test conditions (MS 3000)
Instrument: Malvern Mastersizer 3000
Accessory: Aero S
Particle Type: X Non-Spherical
Material: Name: Default
Refractive index: 1.520
Absorption index: 0.1
Density: g/cm$^3$ (default: 1 g/cm$^3$)
Measurement duration: Background: 5 sec Sample: 5 sec
Sequence: Number of measurements: 1
Obscuration: Limit: 1-8%
X Auto-start: Stabilisation time: 0 sec
X Filtering: Time-out: 10 sec
Accessory control: Air pressure: 0.5 barg
Feed rate: 30%
Configuration: Venturi type: X Standard Venturi disperser
Tray type: X General purpose tray
Hopper gap: 4 mm Mesh
basket used: No
Ball bearing used: No
Data processing: Model: X General purpose
Fine powder: No
Advanced settings: Keep a single result mode: No
Result Range: Limit the result size range: Yes X No
Result Type: X Volume Distribution (recommended)
Sample preparation:
The test sample is homogenized by shaking and rotating the sample bottle by hand for approx. 1 minute.
The parameters marked with * can be changed depending on the adhesion and flow properties of the sample to achieve adequate coverage.
Expression of results: Results d10, d50 and d90 are given as the average of validated measurement results obtained from three independent sample preparations.

7.b. PSD Method Description for Micronized Pregabalin
Instrument: Malvern Mastersizer 3000
Accessory: Aero S
Particle Type: X Non-Spherical
Material: Name: Default
Refractive index: 1.520
Absorption index: 0.1
Density: g/cm$^3$ (default: 1 g/cm$^3$)
Measurement duration: Background: 5 sec Sample: 5 sec
Sequence: Number of measurements: 1
Obscuration: Limit: 1-8%
X Auto-start: Stabilisation time: 0 sec
X Filtering: Time-out: 10 sec
Accessory control: Air pressure: 3.0 barg
Feed rate: 40%
Configuration: Venturi type: High energy Venturi disperser
Tray type: X General purpose tray
Hopper gap: 4 mm
Mesh basket used: No
Ball bearing used: No
Data processing: Model: General purpose
Fine powder: No
Advanced settings: Keep a single result mode: No
Result Range: Limit the result size range: No
Result Type: Volume Distribution (recommended)
Sample preparation:
The test sample is homogenized by shaking and rotating the sample bottle by hand for approx. 1 minute.
The parameters marked with * can be changed depending on the adhesion and flow properties of the sample to achieve adequate coverage.
Expression of results: Results d10, d50 and d90 are given as the average of validated measurement results obtained from three independent sample preparations.

Example 5

Particle Size Analysis with SAX

X-ray scattering of structural elements in the nanoscale range is in the range of small angles (between 0° and approximately 10°). (The Bragg equation establishes a relationship between a large period spacing and a small scattering angle). The SAXS measurements were performed on a SAXS instrument called CREDO of the Research Group for Biological Nanochemistry in the Institute of Materials and Environmental chemistry of the Research Centre for Natural Sciences, Hungarian Academy of Sciences (Wacha, Varga, and Bóta 2014; Wacha 2015). The samples provided weak scatter due to the low electron density contrast of their components and the matrix, therefore it was necessary to measure for several hours compared to the usual measurement time of the order of minutes until the sufficient signal-to-noise ratio was reached. The measurement of the samples took the exposure times more than 23 hours.

For the measurement, the samples were filled into borosilicate capillaries with a nominal outer diameter of 1.0 mm and a wall thickness of 0.01 mm and a circular cross-section, which were afterwards sealed with a glass stopper and two-component epoxy resin to ensure they are vacuum-proof. The sealed capillaries were then placed in the sample holder block of the equipment, the temperature of which was maintained at 25° C. during the measurement. Measurements were performed at a sample-detector distance of 529.66 mm. In SAXS measurements, the angular dependence of the scattered intensity is expressed using the scattering variable q (also known as the momentum transfer, defined as $q=4\pi \sin \theta/\lambda$, where $2\theta$ is the scattering angle, $\lambda \approx 0.154$ nm is the X-ray wavelength of the applied Cu Kα radiation) For the calibration of the q-scale, thus the sample-to-detector distance, a silver behenate sample was used. The intensity scale was calibrated into absolute, instrument-independent units of differential scattering cross section using a Glassy Carbon specimen pre-calibrated against the scattering intensity of water (Orthaber, Bergmann, and Glatter 2000). Measurements were performed with the "cct" program written for the device. Samples were measured at repeated exposures of 300 s each. After each exposure, the scattering image was processed and corrected by the on-line data evaluation routine implemented in the measurement program (taking into account instrumental and external background signals, sample self-absorption and thickness, and geometrical distortions such as the solid angle difference for each pixel of the detector). Defective exposures were filtered out by statistical analysis, and corrected images were averaged over each sample. The final scattering patterns were azimuthally averaged to yield the scattering curves.

The thus obtained SAXS curves were evaluated according to the mathematical method described above and the micelle scattering contribution scaling factor $(I_0)*100$; $(cm^{-1}sr^{-1})$ was calculated.

Orthaber, D., A. Bergmann, and O. Glatter. 2000. "SAXS Experiments on Absolute Scale with Kratky Systems Using Water as a Secondary Standard." *Journal of Applied Crystallography* 33 (2): 218-225.

Porod, G. 1951. "Die Röntgenkleinwinkelstreuung von Dichtgepackten Kolloiden Systemen. I. Teil." *Colloid & Polymer Science* 124 (2): 83-114.

Schmidt, P. W. 1991. "Small-Angle Scattering Studies of Disordered, Porous and Fractal Systems." *Journal of Applied Crystallography* 24 (5): 414-435.

Wacha, András. 2015. "Optimized Pinhole Geometry for Small-Angle Scattering." *Journal of Applied Crystallography* 48 (6): 1843-48. https://doi.org/10.1107/S1600576715018932.

Wacha, András, Zoltán Varga, and Attila Bóta. 2014. "CREDO: A New General-Purpose Laboratory Instrument for Small-Angle X-Ray Scattering." *Journal of Applied Crystallography* 47 (5): 1749-54. https://doi.org/10.1107/S1600576714019918.

PREPARATION EXAMPLES

Placebo Formula P-1 (PGA 0440717—Simple Mixed Placebo)
(Topical Preparation without Pregabalin)
Batch 2000 g
Composition (100 g):

| Batch No. | PGA0440717 |
| --- | --- |
| Process | P-1 |
| Components | [g] |
| Soya lechitin (Deoiled Soya Lecithin) | 1.0000 |
| Decylis oleas/Kollicream DO/ | 2.5000 |
| Oktyldecanol | 5.0000 |
| Izopropanol | 10.0000 |
| DL-alpha-tokopherol | 0.5000 |
| EDTA | 0.0050 |
| Carbomer (980) | 0.7500 |
| Ammonia solution (25 tömeg % aqueous) | 0.5880 |
| Purified water | 79.6570 |
| Sum | 100.00 |
| HPH treatment of lipid phase | 0 |

A Process for Preparing a Placebo Topical Formulation
1: Preparation of gel phase: In twentyfold amount of purified water Carbopol 980 is swelled, then the pH is adjusted to pH 7.0 by adding aqueous ammonia solution.
2. Preparation of the lipid phase: Soya lecithin is swelled in ten-fold amounts of purified water at 25-40° C., then isopropyl alcohol is added and the resulting mixture mixed with the gel phase.
3. Octyl decanol, DL-alpha-tocopherol, decylis oleas and EDTA are added to the thus obtain gel phase. The resulting mixture was homogenized at room temperature and homogenized.

Placebo Formula P-2 (Batch No. PGA 0460717—HPH Homogenized Placebo)

The composition of PGA 0460717 is the same as PGA 0440717.

The preparation method differs only in that in step 2, in which the mixture of twenty times the amount of soy lecithin swelled in purified water mixed with isopropanol and the mixture was homogenized 5 times with an HPH homogenizer, and then the mixture thus homogenized was added to the gel phase.

Reference Example R-1 (PGA2180719)

(Topical formula containing 2.5% of pregabalin in dissolved form.).
Batch size 2000 g
Composition of the formula (100 g):

| Batch No | PGA2180719 |
| --- | --- |
| Process | R-1 |
| Compound | [g] |
| Pregabalin (micronized) | 2.5000 |
| LECITHIN (LIPOID P 75) | 0.5000 |
| Decylis oleas/Kollicream DO/ | 1.2500 |
| Coconut oil refined | 5.0000 |
| Isopropyl alcohol | 10.0000 |
| DL-alpha-Tocopherol | 0.2500 |
| Benzyl alcohol | 1.0000 |
| EDTA | 0.0025 |
| Carbomers (980) | 0.4000 |
| Ammonium solution (25 weight % aqueous sol.) | 0.3136 |
| Purified water | 78.7839 |
| Sum | 100.00 |
| Number of HPH of lipid phase | 0 |

Process for the Preparation of Topical Composition Comprising Pregabalin
1: Preparation of gel phase: In twentyfold amount of purified water Carbopol 980 is swelled, then the pH is adjusted to pH 7.0 by adding aqueous ammonia solution.
2. Preparation of lipid phase: In twentyfold amount of purified water LIPOID P 75 is swelled at 25-40° C., then isopropyl alcohol and DL-alpha-Tocopherol are added to the mixture and homogenized.
3. The lipid phase is added to the gel phase while stirring, then homogenized.
5. To the homogenized mixture of lipid phase and gel phase coconut oil, Decylis oleas, an aqueous solution of EDTA and benzyl alcohol are added in this order.
6. Pregabalin is suspended in the rest of the water and mixed into the cream of point 4 at 30° C., then the obtained cream is homogenized with a colloid mill for 120 min, then the evaporated water is replaced with purified water while stirring. During the homogenization pregabalin dissolves.
7. The thus obtained cream is cooled to 25° C. and filled into containers. (Preferably in polyfoil or aluminum tubes.)

Results of mouse model of neuropathic pain:
Data for FIG. 1: Plantar withdrawal threshold data in MPNL model: effect of 50 µl PGA 2180719 treatment (2.5% pregabalin cream, 50 µl/right foot, mean values±S.E.M. n=6), PWT values for both feet

| PGA2180719 T | Intact paw Mean | Intact paw SEM | MPNL paw Mean | MPNL paw SEM | mice n | difference between the two paws p |
|---|---|---|---|---|---|---|
| base | 0.789 | 0.080 | 0.090 | 0.017 | 6 | * |
| +30 min | 0.700 | 0.037 | 0.813 | 0.125 | 6 | n.s. |
| +1 h | 0.833 | 0.061 | 0.797 | 0.132 | 6 | n.s. |
| +3 h | 0.763 | 0.083 | 0.643 | 0.120 | 6 | n.s. |
| +5 h | 0.667 | 0.042 | 0.128 | 0.056 | 6 | * | n.s.: not significant;
* $p < 0.05$

Reference Example R-2 (PGA2190719)

(Topical formula containing 5% of pregabalin in dispersed form.).
Batch size 2000 g
Composition of the formula (100 g):

| Batch No: | PGA2190719 |
|---|---|
| Process | R-2 |
| Component | g |
| Pregabalin (ground) | 5.0000 |
| LECITHIN (LIPOID P 75) | 0.5000 |
| Decylis oleas/Kollicream DO/ | 1.2500 |
| Coconut oil refined | 5.0000 |
| Isopropyl alcohol | 10.0000 |
| DL-alpha-Tocopherol | 0.2500 |
| Benzylalcohol | 1.0000 |
| EDTA | 0.0025 |
| Carbomers (980) | 0.4000 |
| Ammonium solution (25 weight % aqueous sol.) | 0.3136 |
| Purified water | 76.2839 |
| Sum | 100.00 |
| Number of HPH of lipid phase | 0 |

Process for the Preparation of Topical Composition Comprising Pregabalin
1: Preparation of gel phase: In twentyfold amount of purified water Carbopol 980 is swelled, then the PH is adjusted to pH 7.0 by adding aqueous ammonia solution.
2. Preparation of lipid phase: In twentyfold amount of purified water LIPOID P 75 is swelled at 25-40° C., then isopropyl alcohol and DL-alpha-Tocopherol are added to the mixture and homogenized.
3. The lipid phase is added to the gel phase while stirring, then homogenized.
4. To the homogenized mixture of lipid phase and gel phase coconut oil, Decylis oleas, an aqueous solution of EDTA and benzyl alcohol are added in this order.
5. Pregabalin is suspended in the rest of the water and mixed into the cream of point 4 at 30° C., then the obtained cream is homogenized with a colloid mill for 120 min, then the evaporated water is replaced with purified water while stirring.
6. The thus obtained cream is cooled to 25° C. and filled into containers. (Preferably in aluminum or polyfoil tubes.)

Results of the Mouse Model of Neuropathic Pain:
Data for FIG. 1: Plantar withdrawal threshold data in MPNL model: effect of 20 µl PGA 2190719 treatment (5% pregabalin cream, 20 µl/right foot, mean values±S.E.M. n=7), PWT values for both feet

| PGA2190719 T | Intact paw Mean | Intact paw SEM | MPNL paw Mean | MPNL paw SEM | mice N | difference between the two paws p |
|---|---|---|---|---|---|---|
| base | 0.743 | 0.037 | 0.042 | 0.009 | 7 | * |
| +30 min | 0.771 | 0.052 | 0.576 | 0.138 | 7 | n.s. |
| +1 h | 0.743 | 0.075 | 0.517 | 0.134 | 7 | * |
| +3 h | 0.700 | 0.049 | 0.516 | 0.097 | 7 | n.s. |
| +5 h | 0.671 | 0.047 | 0.164 | 0.070 | 7 | * | n.s.: not significant;
* $p < 0.05$

Reference Example R-3 (PGA0450717)

(Topical formula containing 15% of pregabalin in dispersed form)
Batch size 2000 g
Composition of the formula (100 g):

| Batch No. | PGA0450717 |
|---|---|
| Process | R-3 |
| Component | g |
| Pregabalin (ground) | 15.0000 |
| SOYA LECITHIN (Deoiled Soya Lecithin) | 0.5000 |
| Decylis oleas/Kollicream DO/ | 1.2500 |
| Octyldodecanol | 2.5000 |
| Isopropyl alcohol | 5.0000 |
| DL-alpha-Tocopherol | 0.2500 |
| EDTA | 0.0025 |
| Carbomers (980) | 0.3750 |
| Ammonium solution (25 weight % aqueous sol.) | 0.2940 |
| Purified water | 74.8285 |
| SUM: | 100.00 |
| number of HPH of lipid phase | 0 |

Process for the Preparation of Topical Composition Comprising Pregabalin

1. Preparation of gel phase: In twentyfold amount of purified water Carbopol 980 is swelled, then the pH is adjusted to pH 7.0 by adding aqueous ammonia solution.
2. Preparation of lipid phase: In tenfold amount of purified water LIPOID P 75 is swelled at 25-40° C., then isopropyl alcohol, DL-alpha-Tocopherol and octyldodecanol are added to the mixture and homogenized.
3. The lipid phase is added to the gel phase while stirring, then homogenized.
4. To the homogenized mixture of lipid phase and gel phase, Decylis oleas, an aqueous solution of EDTA are added in this order.
5. Pregabalin is suspended in the rest of the water and mixed into the cream of point 5 at 30° C., then the obtained cream is homogenized with a colloid mill for 120 min, then the evaporated water is replaced with purified water while stirring.
6. The thus obtained cream is cooled to 25° C. and filled into containers. (Preferably in aluminum or polyfoil tubes.)

Homogenization was performed in a Stephan mixer. Device information: Stephan UMC 5 electronic (Manufacturing number: 722.780.01) Equipment manufacturer: A. Stephan und Söhne GmbH & Co., Year of manufacture: 1998.

Homogenization was performed at a stirring speed of 300 rpm and a scraper stirring speed of 20 rpm we are done.

Figure 1:
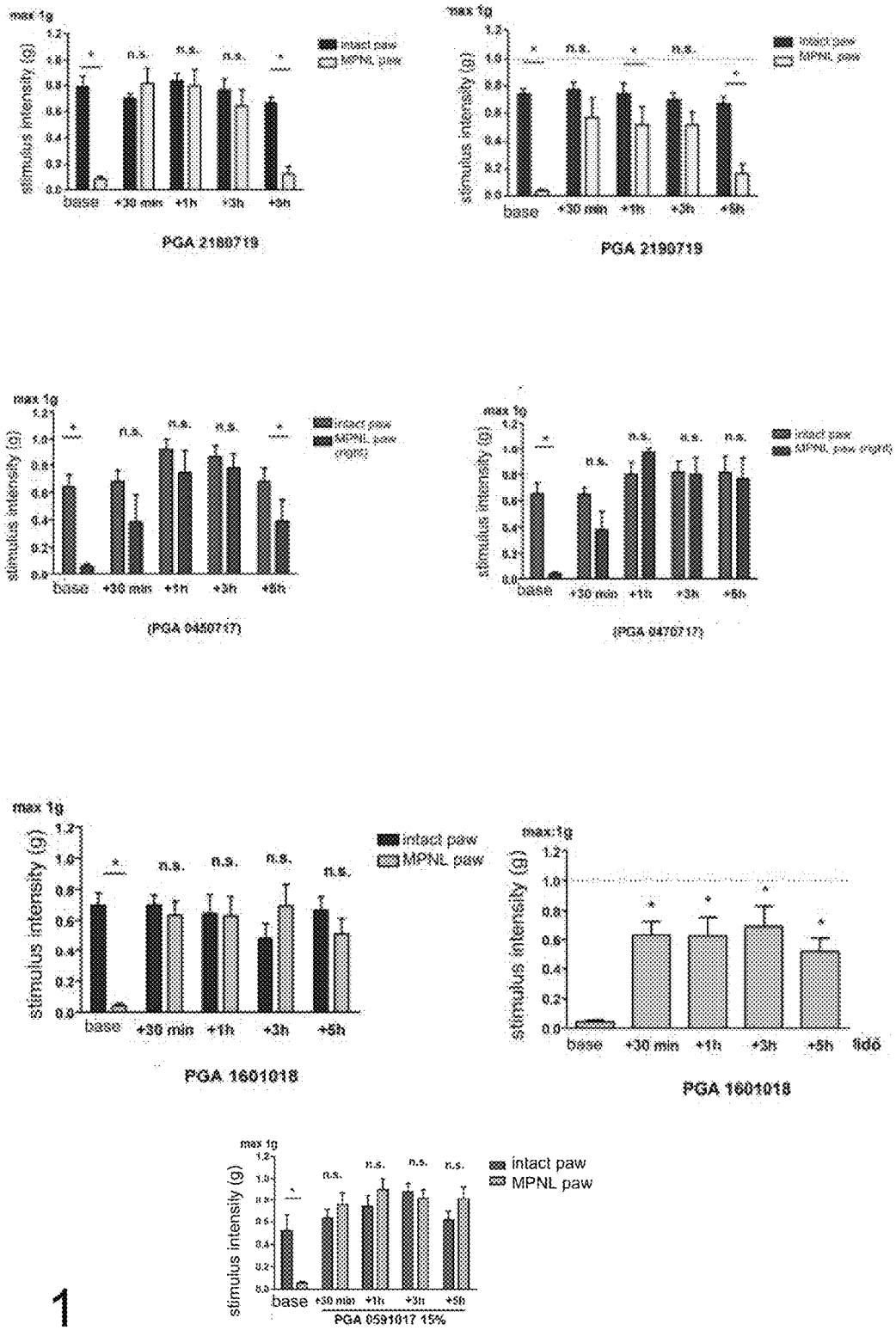
FIG. 1: Plantar withdrawal threshold diagrams 7 days after MPNL surgery in NMRI mice.

Results of the Mouse Model of Neuropathic Pain:

Data for FIG. 1: Plantar withdrawal threshold data in MPNL model: effect of 50 μl PGA 0450717 treatment (15% pregabalin cream, 50 μl/right foot, mean values±S.E.M. n=5), PWT values for both feet

| PGA0450717 T | Intact paw Mean | Intact paw SEM | MPNL paw Mean | MPNL paw SEM | Number of mice N | difference between the two paws p |
|---|---|---|---|---|---|---|
| base | 0.640 | 0.091 | 0.0620 | 0.0150 | 5 | * |
| +30 min | 0.680 | 0.080 | 0.3840 | 0.1970 | 5 | n.s. |
| +1 h | 0.916 | 0.084 | 0.7430 | 0.1630 | 5 | n.s. |
| +3 h | 0.860 | 0.087 | 0.7800 | 0.1020 | 5 | n.s. |
| +5 h | 0.680 | 0.097 | 0.3900 | 0.1560 | 5 | * | n.s.: not significant;
* $p < 0.05$

WORKING EXAMPLES

WE-1 General Procedure:

1. Preparation of gel phase:
   In ten or twentyfold amount of purified water Carbopol 980 is swelled, then the pH is adjusted to pH 7.0 by adding aqueous ammonia solution.
2. Preparation of lipid phase:
   In twentyfold amount of purified water soya lecithin (Deoiled Soya Lecithin) is swelled at 25-40° C., then isopropyl alcohol, Octyldodecanol and DL-alpha-Tocopherol are added to the mixture and homogenized.
3. HPH homogenization of the lipid phase:
   The thus obtained solution is homogenized n times by High pressure homogenizer. The used pressure is preferably between 500-1500 bar. During the HPH homogenization the solution warms up to 25-50° C. The thus obtained lipid phase is cooled to between 20-30° C. and if it is necessary the evaporated water is replaced by adding purified water while stirring.
4. The lipid phase is added to the gel phase at 30-35° C. while stirring, then homogenized.
5. To the homogenized mixture of lipid phase and gel phase Decylis oleas and an aqueous solution of EDTA are added in this order.
6. Pregabalin is suspended in the rest of the water and then mixed into the cream of point 5 at 30° C., then the obtained cream is homogenized for 120 min, then the evaporated water is replaced with purified water.
7. The thus obtained cream is cooled to 25° C. and filled into containers. (Preferably in aluminum or polyfoil tubes.)

Compositions Prepared According to WE-1 Process:

| Batch No. | PGA0980418* | PGA1000418* | PGA1040418* | PGA0470717 (PGA0591017) (PGA0651117) (PGA0661117) 9x (PGA1010418) (PGA1060418##) | PGA0641117 (PGA0990418*) |
|---|---|---|---|---|---|
| Process | WE-1 | WE-1 | WE-1 | WE-1 | WE-1 |
| Pregabaline | 15.0000 | 15.0000 | 15.0000 | 15.0000 | 15.0000 |
| Phospholipid | 0.5000 | 0.5000 | 0.5000 | 0.5000 | 0.5000 |
| Decylis oleas Kollicream/DO/ | 1.2500 | 1.2500 | 1.2500 | 1.2500 | 1.2500 |
| Octyldodecanol | 2.5000 | 2.5000 | 2.5000 | 2.5000 | 2.5000 |
| Isopropyl alcohol | 5.0000 | 5.0000 | 5.0000 | 5.0000 | 5.0000 |
| DL-alpha-Tocopherol | 0.2500 | 0.2500 | 0.2500 | 0.2500 | 0.2500 |
| EDTA | 0.0025 | 0.0025 | 0.0025 | 0.0025 | 0.0025 |
| Carbomers (980) | 0.3750 | 0.3750 | 0.3750 | 0.3750 | 0.3750 |

-continued

| Batch No. | PGA0980418* | PGA1000418* | PGA1040418* | PGA0470717 (PGA0591017) (PGA0651117) (PGA0661117) 9x (PGA1010418) (PGA1060418##) | PGA0641117 (PGA0990418*) |
|---|---|---|---|---|---|
| Ammonium solution (25 weight % aqueous sol.) | 0.2940 | 0.2940 | 0.2940 | 0.2940 | 0.2940 |
| Purified water | 74.8285 | 74.8285 | 74.8285 | 74.8285 | 74.8285 |
| Sum | 100.00 | 100.00 | 100.00 | 100.00 | 100.00 |
| Micelle scattering contribution scaling factor $(I_0)*100$; $(cm^{-1}sr^{-1})$ | | | | $0.018 \pm 0.001$ $(0.015 \pm 0.001)$ | $0.021 \pm 0.002$ (n.a.) |
| n number of HPH of lipid phase | 1 | 4 | 9 | 5 or 9 | 3 |

Phospholipid: SOYA LECITHIN (Deoiled Soya Lecithin), # LECITHIN (LIPOID P 75, LIPOID S 75), (Parallel batches are in the same column. Usually, the promising batches were reproduced more times to produce further samples for analytical purposes and for in vivo experiments. Usually, parallel batches have identical properties.)

Results of Mouse Model of Neuropathic Pain:

Data for FIG. 1: Plantar withdrawal threshold data in MPNL model:
Effect of 50 μl PGA 0470717 treatment (15% pregabalin cream, 50 μl/right foot, mean±S.E.M. n=6), PWT values for both feet

| PGA0470717 T | Intact paw Mean | Intact paw SEM | MPNL paw Mean | MPNL paw SEM | Number of mice N | difference between the two paws p |
|---|---|---|---|---|---|---|
| base | 0.645 | 0.083 | 0.045 | 0.012 | 6 | * |
| +30 min | 0.650 | 0.050 | 0.381 | 0.140 | 6 | n.s. |
| +1 h | 0.800 | 0.089 | 0.967 | 0.033 | 6 | n.s. |
| +3 h | 0.817 | 0.083 | 0.800 | 0.126 | 6 | n.s. |
| +5 h | 0.813 | 0.125 | 0.769 | 0.154 | 6 | n.s. | n.s.: not significant;
* $p < 0.05$

| PGA0591017 T | Intact paw Mean | Intact paw SEM | Number of mice N | MPNL paw Mean | MPNL paw SEM | Number of mice N | difference between the two paws p |
|---|---|---|---|---|---|---|---|
| base | 0.523 | 0.143 | 5 | 0.0570 | 0.0140 | 5 | * |
| +30 min | 0.636 | 0.078 | 5 | 0.7600 | 0.1120 | 5 | n.s. |
| +1 h | 0.740 | 0.108 | 5 | 0.9000 | 0.1000 | 5 | n.s. |
| +3 h | 0.880 | 0.080 | 5 | 0.8200 | 0.0800 | 5 | n.s. |
| +5 h | 0.620 | 0.080 | 5 | 0.8160 | 0.1130 | 5 | n.s. |

Figure 2:
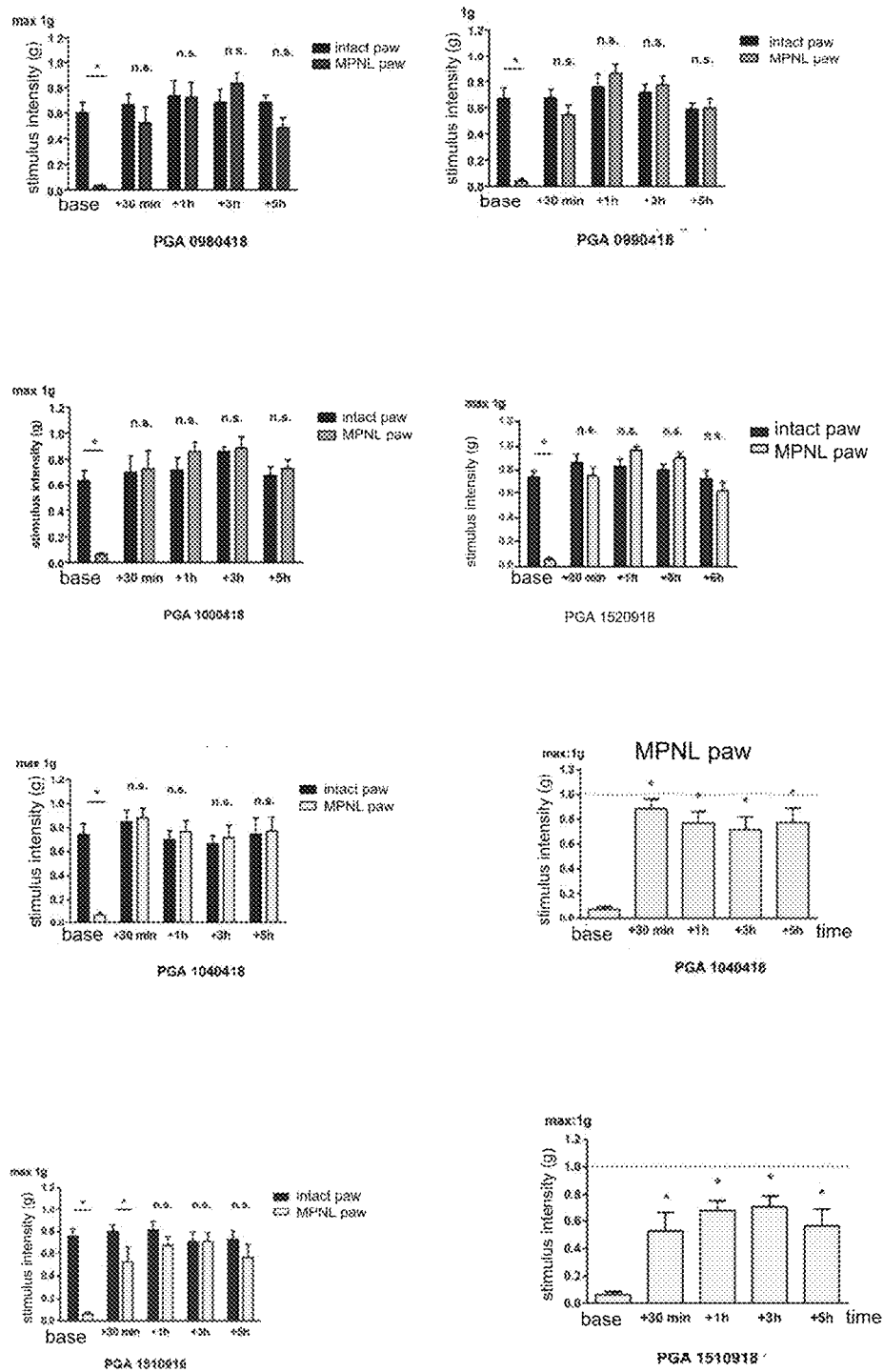
FIG. 2: Plantar withdrawal threshold diagrams 7 days after MPNL surgery in NMRI mice.

Data for FIG. 2: Plantar Withdrawal Threshold Data in MPNL Model:

Effect of the treatment of 20 μl PGA 0980418 (15% pregabalin cream, 20 μl/right foot, mean±S.E.M.), PWT values for both feet

| PGA0980418 T | Intact paw Mean | Intact paw SEM | MPNL paw Mean | MPNL paw SEM | Number of mice N | difference between the two paws p |
|---|---|---|---|---|---|---|
| base | 0.604 | 0.081 | 0.033 | 0.004 | 6 | * |
| +30 min | 0.667 | 0.080 | 0.525 | 0.122 | 6 | n.s. |
| +1 h | 0.733 | 0.120 | 0.723 | 0.117 | 6 | n.s. |
| +3 h | 0.683 | 0.101 | 0.833 | 0.080 | 6 | n.s. |
| +5 h | 0.683 | 0.054 | 0.486 | 0.077 | 6 | n.s. | n.s.: not significant;
* $p < 0.05$

FIG. 2: Effect of 20 µl PGA 0990418 treatment (15% pregabalin cream, 20 µl/right foot, mean±S.E.M.), PWT values for both feet

| PGA0990418 T | Intact paw Mean | Intact paw SEM | MPNL paw Mean | MPNL paw SEM | Number of mice n | difference between the two paws p |
|---|---|---|---|---|---|---|
| base | 0.665 | 0.083 | 0.0420 | 0.0140 | 7 | * |
| +30 min | 0.671 | 0.064 | 0.5450 | 0.0740 | 7 | n.s. |
| +1 h | 0.754 | 0.099 | 0.8570 | 0.0720 | 7 | n.s. |
| +3 h | 0.714 | 0.059 | 0.7710 | 0.0680 | 7 | n.s. |
| +5 h | 0.586 | 0.046 | 0.5940 | 0.0740 | 7 | n.s. | n.s.: not significant;
* $p < 0.05$

FIG. 2: Effect of 20 µl PGA 1000418 treatment (15% pregabalin cream, 20 µl/right foot, mean±S.E.M.), PWT values for both feet

| PGA1000418 T | Intact paw Mean | Intact paw SEM | MPNL paw Mean | MPNL paw SEM | Number of mice n | difference between the two paws p |
|---|---|---|---|---|---|---|
| base | 0.634 | 0.076 | 0.065 | 0.007 | 7 | * |
| +30 min | 0.696 | 0.129 | 0.725 | 0.138 | 7 | n.s. |
| +1 h | 0.714 | 0.094 | 0.857 | 0.072 | 7 | n.s. |
| +3 h | 0.857 | 0.037 | 0.886 | 0.086 | 7 | n.s. |
| +5 h | 0.671 | 0.068 | 0.729 | 0.064 | 7 | n.s. | n.s.: not significant;
* $p < 0.05$

FIG. 2: Effect of 20 µl PGA 1040418 treatment (15% pregabalin cream, 20 b/right foot mean n S.E.M.), PWT values for both feet

| PGA1040418 T | Intact paw Mean | Intact paw SEM | MPNL paw Mean | MPNL paw SEM | Number of mice n | difference between the two paws p |
|---|---|---|---|---|---|---|
| base | 0.742 | 0.090 | 0.075 | 0.015 | 6 | * |
| +30 min | 0.850 | 0.096 | 0.883 | 0.161 | 6 | n.s. |
| +1 h | 0.700 | 0.073 | 0.767 | 0.073 | 6 | n.s. |
| +3 h | 0.667 | 0.067 | 0.717 | 0.109 | 6 | n.s. |
| +5 h | 0.747 | 0.133 | 0.772 | 0.086 | 6 | n.s. | n.s.: not significant;
* $p < 0.05$

WE-2 General Procedure:
1. Preparation of gel phase:
   In twentyfold amount of purified water Carbopol 980 is swelled, then the pH is adjusted to pH 7.0 by adding aqueous ammonia solution.
2. Preparation of lipoid phase:
   In twentyfold amount of purified water LIPOID P 75 (lecithin) is swelled at 25-40° C., then isopropyl alcohol and DL-alpha-Tocopherol are added to the mixture and homogenized.
3. HPH homogenization of the lipid phase:
   The thus given solution is homogenized n=5 times by High pressure homogenizer. The used pressure was between 500-1500 bar. During HPH homogenization the solution warms up to 25-50° C. The thus obtained lipid phase is cooled to between 20-30° C. and if it is necessary the evaporated water is replaced by adding purified water while stirring.
4. The lipid phase is added to the gel phase while stirring, then homogenized.
5. To the homogenized mixture of lipid phase and gel phase coconut oil, Decylis oleas, an aqueous solution of EDTA and benzyl alcohol are added in this order.
6. Pregabalin is suspended in the rest of the water and mixed into the cream of point 5 at 30° C., then the obtained cream is homogenized for 120 min, then the evaporated water is replaced with purified water.
7. The thus obtained cream is cooled to 25° C. and filled into containers. (Preferably in aluminum or polyfoil tubes.)

Compositions Prepared According to WE-2 Process:

| Batch No | PGA1591018 | PGA1601018 | PGA 1671118 |
|---|---|---|---|
| Compound | g | g | g |
| Process type | WE-2 | WE-2 | WE-2 |
| Pregabalin (micronized) | 10.0000 | 5.0000 | 5.0000 |
| Phospholipid (LECITHIN (LIPOID P 75) | 1.0000 | 1.0000 | 1.0000 |
| Decylis oleas/ Kollicream DO/ Octyldodecanol | 1.2500 | 1.2500 | 1.2500 |
| | 0.0000 | 0.0000 | 0.0000 |
| Coconut oil | 10.0000 | 10.0000 | 10.0000 |
| Isopropyl alcohol | 10.0000 | 10.0000 | 10.0000 |
| DL-alpha-Tocopherol | 0.2500 | 0.2500 | 0.2500 |
| EDTA | 0.0025 | 0.0025 | 0.0025 |
| Benzyl alcohol | 2.0000 | 2.0000 | 1.000 |
| Carbomers (Carbopol 980) | 0.3750 | 0.3750 | 0.3750 |

| Batch No | PGA1591018 | PGA1601018 | PGA 1671118 |
|---|---|---|---|
| Ammonium solution (25 weight % aqueous sol.) | 0.2940 | 0.2940 | 0.2940 |
| Purified water | 64.8285 | 69.8285 | 71.7285 |
| Sum | 100.00 | 100.00 | 100.00 |
| n (Number of HPH of lipid phase) | 5 | 5 | 5 |

Results of a Mouse Model of Neuropathic Pain:

FIG. 3. Effect of 20 μl PGA 1591018 treatment (10% pregabalin cream, 20 μl/right foot, mean±S.E.M.), PWT values for both feet

| PGA1591018 T | Intact paw Mean | Intact paw SEM | MPNL paw Mean | MPNL paw SEM | Number of mice n | difference between the two paws p |
|---|---|---|---|---|---|---|
| base | 0.742 | 0.900 | 0.034 | 0.006 | 6 | * |
| +30 min | 0.717 | 0.075 | 0.649 | 0.160 | 6 | n.s. |
| +1 h | 0.683 | 0.083 | 0.933 | 0.042 | 6 | n.s. |
| +3 h | 0.700 | 0.082 | 0.933 | 0.042 | 6 | n.s. |
| +5 h | 0.633 | 0.092 | 0.817 | 0.091 | 6 | n.s. | n.s.: not significant;
* $p < 0.05$

WE-3 General Procedure:

| PGA1601018 T | Intact paw Mean | Intact paw SEM | MPNL paw Mean | MPNL paw SEM | Number of mice n | difference between the two paws p |
|---|---|---|---|---|---|---|
| base | 0.698 | 0.078 | 0.043 | 0.006 | 6 | * |
| +30 min | 0.700 | 0.063 | 0.633 | 0.160 | 6 | n.s. |
| +1 h | 0.643 | 0.120 | 0.630 | 0.042 | 6 | n.s. |
| +3 h | 0.483 | 0.097 | 0.693 | 0.042 | 6 | n.s. |
| +5 h | 0.667 | 0.088 | 0.516 | 0.091 | 6 | n.s. | n.s.: not significant;
* $p < 0.05$

1. Preparation of gel phase:

In twentyfold amount of purified water Carbopol 980 is swelled, then the pH is adjusted to pH 7.0 by adding aqueous ammonia solution.

2. Preparation of lipoid phase:

In twentyfold amount of purified water LIPOID P 75 is swelled at 25-40° C., then isopropyl alcohol and DL-alpha-Tocopherol are added to the mixture and homogenized.

3. HPH homogenization of the lipid phase:

The thus obtained solution is homogenized n=5 times by a High pressure homogenizer. During HPH homogenization the solution warms up to 25-50° C. The thus obtained lipid phase is cooled to between 20-30° C. and if it is necessary the evaporated water is replaced by adding purified water while stirring.

4. The lipid phase is added to the gel phase while stirring, then homogenized.

5. To the homogenized mixture of lipid phase and gel phase Decylis oleas and an aqueous solution of EDTA are added in this order.

6. Pregabalin is suspended in the rest of the water and mixed into the cream of point 5 at 30° C., then the obtained cream is homogenized for 120 min, then the evaporated water is replaced with purified water.

7. The thus obtained cream is cooled to 25° C. and filled into containers. (Preferably in aluminium or polyfoil tubes.)

Compositions Prepared According to WE-3 Process:

| Batch No. | PGA1370718 | PGA1450718 | PGA1460718 | PGA1510918 | PGA1520918 |
|---|---|---|---|---|---|
| Compound | g | g | g | g | g |
| Process type: | WE-3 | WE-3 | WE-3 | WE-3 | WE-3 |
| Pregabaline (micronized) | 15.0000 | 10.0000 | 5.0000 | 10.0000 | 37.5000 |
| Phospholipid (LECITHIN (LIPOID P 75)) | 0.2500 | 0.2500 | 0.2500 | 0.2500 | 0.2500 |
| Decylis oleas/ Kollicream DO/ | 1.2500 | 1.2500 | 1.2500 | 1.2500 | 1.2500 |
| Octyldodecanol | 0.0000 | 0.0000 | 0.0000 | 0.0000 | 0.0000 |
| Coconut oil | 0.0000 | 0.0000 | 0.0000 | 0.0000 | 0.0000 |
| Isopropyl alcohol | 2.5000 | 2.5000 | 2.5000 | 2.5000 | 2.5000 |
| DL-alpha-Tocopherol | 0.1250 | 0.1250 | 0.1250 | 0.1250 | 0.1250 |
| EDTA | 0.0025 | 0.0025 | 0.0025 | 0.0025 | 0.0025 |
| Benzyl alcohol | 0.0000 | 0.0000 | 0.0000 | 0.0000 | 0.0000 |
| Carbomers (Carbopol 980) | 0.3750 | 0.3750 | 0.3750 | 0.3750 | 0.3750 |

-continued

| Batch No. | PGA1370718 | PGA1450718 | PGA1460718 | PGA1510918 | PGA1520918 |
|---|---|---|---|---|---|
| Ammonium solution (25 weight % aqueous sol.) | 0.2940 | 0.2940 | 0.2940 | 0.2940 | 0.2940 |
| All ingredients | 19.7965 | 14.7965 | 9.7965 | 14.7965 | 42.2965 |
| Purified water | 80.2035 | 85.2035 | 90.2035 | 85.2035 | 57.7035 |
| Sum | 100.00 | 100.00 | 100.00 | 100.00 | 100.00 |
| Micelle scattering contribution scaling factor ($I_0$) *100; ($cm^{-1}sr^{-1}$) | | | | 0.010 ± 0.001 | 0.010 ± 0.001 |
| n (Number of HPH of lipid phase) | 5 | 5 | 5 | 125 | 5 |

Results of a Mouse Model of Neuropathic Pain:

FIG. 3. Comparative plantar withdrawal threshold diagrams 7 days after MPNL surgery in NMRI mice:

Comparison of the effects of PGA1460718 (5%), PGA1450718 (10%), PGA1370718 (15%) (20 μl/right foot, mean±S.E.M.), PWT values for both feet FIG. 3 shows data for the treated foot only.

| PGA1370718 T | Intact paw Mean | Intact paw SEM | MPNL paw Mean | MPNL paw SEM | Number of mice n | difference between the two paws p |
|---|---|---|---|---|---|---|
| base | 0.714 | 0.048 | 0.054 | 0.015 | 7 | * |
| +30 min | 0.729 | 0.064 | 0.806 | 0.140 | 7 | n.s. |
| +1 h | 0.757 | 0.061 | 0.814 | 0.077 | 7 | n.s. |
| +3 h | 0.743 | 0.102 | 0.829 | 0.092 | 7 | n.s. |
| +5 h | 0.657 | 0.057 | 0.609 | 0.105 | 7 | n.s. | n.s.: not significant;
* $p < 0.05$

| PGA1450718 T | Intact paw Mean | Intact paw SEM | MPNL paw Mean | MPNL paw SEM | Number of mice n | difference between the two paws p |
|---|---|---|---|---|---|---|
| base | 0.705 | 0.054 | 0.037 | 0.007 | 7 | * |
| +30 min | 0.700 | 0.065 | 0.646 | 0.118 | 7 | n.s. |
| +1 h | 0.614 | 0.070 | 0.857 | 0.072 | 7 | * |
| +3 h | 0.714 | 0.103 | 0.886 | 0.059 | 7 | n.s. |
| +5 h | 0.634 | 0.116 | 0.654 | 0.106 | 7 | n.s. | n.s.: not significant;
* $p < 0.05$

| PGA1460718 T | Intact paw Mean | Intact paw SEM | MPNL paw Mean | MPNL paw SEM | Number of mice n | difference between the two paws p |
|---|---|---|---|---|---|---|
| base | 0.692 | 0.060 | 0.063 | 0.023 | 8 | * |
| +30 min | 0.713 | 0.058 | 0.204 | 0.079 | 8 | * |
| +1 h | 0.613 | 0.061 | 0.644 | 0.136 | 8 | n.s. |
| +3 h | 0.675 | 0.073 | 0.577 | 0.121 | 8 | n.s. |
| +5 h | 0.638 | 0.038 | 0.507 | 0.137 | 8 | n.s. | n.s.: not significant;
* $p < 0.05$

FIG. 2: Effect of 20 μl PGA 1510918 cream (10% pregabalin, 20 μl/right foot, mean values±S.E.M.), both feet

| PGA1510918 T | Intact paw Mean | Intact paw SEM | MPNL paw Mean | MPNL paw SEM | Number of mice n | difference between the two paws p |
|---|---|---|---|---|---|---|
| base | 0.762 | 0.062 | 0.063 | 0.020 | 7 | * |
| +30 min | 0.800 | 0.062 | 0.526 | 0.135 | 7 | * |
| +1 h | 0.814 | 0.077 | 0.676 | 0.080 | 7 | n.s. |
| +3 h | 0.711 | 0.087 | 0.711 | 0.078 | 7 | n.s. |
| +5 h | 0.729 | 0.078 | 0.566 | 0.120 | 7 | n.s. | n.s.: not significant;
* $p < 0.05$

FIG. 3: Effect of 20 μl PGA 1520918 cream (37.5% pregabalin, 20 μl/right foot, mean±S.E.M.), both-feet

| PGA1520918 T | Intact paw Mean | Intact paw SEM | MPNL paw Mean | MPNL paw SEM | Number of mice n | difference between the two paws p |
|---|---|---|---|---|---|---|
| base | 0.744 | 0.050 | 0.047 | 0.019 | 6 | * |
| +30 min | 0.867 | 0.067 | 0.750 | 0.072 | 6 | n.s. |
| +1 h | 0.833 | 0.061 | 0.967 | 0.033 | 6 | n.s. |
| +3 h | 0.800 | 0.052 | 0.900 | 0.045 | 6 | n.s. |
| +5 h | 0.733 | 0.067 | 0.617 | 0.091 | 6 | n.s. | n.s.: not significant;
* $p < 0.05$

WE-4 General Procedure:
1. Preparation of gel phase:
  a.) Using Carbopol 980 (batches marked PGA):
  In ten or twentyfold amount of purified water Carbopol 980 is swelled, then the pH is adjusted to pH 7.0 by adding aqueous ammonia solution.
  b.) Using xanthan gum (batch AL2890321):
  The xanthan gum was gelled in 10 times the amount of purified water at 60° C. and homogenized by cooling to 25° C.
  c.) Using hydroxyethyl cellulose (batch AL2900321):
  HEC (Hydroxyethylcellulose) was gelled in 10-fold purified water at 37° C. (35-40° C.) and homogenized by cooling to 25° C.
  d.) Using Polaxamer (batch AL2910321):
  Poloxamer 407 was gelled in 10-fold purified then stored a refrigerator for 24 hours, then allowed allow to warm to room temperature.

2. Preparation of lipoid phase:

In twentyfold amount of purified water LIPOID P 75 (lecithin) is swelled at 25-40° C., then isopropyl alcohol and DL-alpha-Tocopherol are added to the mixture and homogenized.

3. HPH homogenization of the lipid phase:

The thus obtained solution is homogenized n=5 times by a High pressure homogenizer. The used pressure is preferably between 500-1500 bar. During HPH homogenization the solution warms up to 25-50° C. The thus obtained lipid phase is cooled to between 20-30° C. and if it is necessary the evaporated water is replaced by adding purified water while stirring.

4. To the homogenized mixture of lipid phase further additives preferably coconut oil, Decylis oleas, an aqueous solution of EDTA and benzyl alcohol are added in this order.

5. Pregabalin is suspended in the rest of the water and mixed into the mixture of point 4 at 30° C. and homogenized for 30 minutes. Then the obtained mixture is homogenized for m=3 times with a high pressure homogenizer. The used pressure is preferably between 500-1500 bar.

During the HPH homogenization the solution warms up to 30-50° C. Then the evaporated water is replaced with purified water if it is necessary.

6. The lipid suspension phase is added to the gel phase while stirring, then the mixture of lipid suspension phase and gel are homogenized for 60 minutes at 25° C.

7. The thus obtained cream is cooled to 25° C. and filled into containers. (Preferably in aluminum polyfoil tubes.)

Compositions Prepared According to WE-4 Process:

| Batch No | PGA2150619# | PGA2211119* | PGA2300320* | PGA2310320* | PGA2320320* |
|---|---|---|---|---|---|
| Process Type | WE-4 | WE-4 | WE-4 | WE-4 | WE-4 |
| Compound | g | g | g | g | g |
| Pregabalin | 5.0000 | 5.0000 | 3.0000 | 5.0000 | 7.5000 |
| Phospholipid | 0.5000 | 0.5000 | 0.5000 | 0.5000 | 0.5000 |
| Decylis oleas/Kollicream DO/ | 1.2500 | 1.2500 | 1.2500 | 1.2500 | 1.2500 |
| Coconut oil | 5.0000 | 5.0000 | 5.0000 | 5.0000 | 5.0000 |
| Isopropyl alcohol | 10.0000 | 10.0000 | 10.0000 | 10.0000 | 10.0000 |
| DL-alpha-Tocopherol | 0.2500 | 0.2500 | 0.2500 | 0.2500 | 0.2500 |
| EDTA | 0.0025 | 0.0025 | 0.0025 | 0.0025 | 0.0025 |
| Benzyl alcohol | 1.0000 | 1.0000 | 1.0000 | 1.0000 | 1.0000 |
| Gelling agent | 0.4000* | 0.4000* | 0.4000* | 0.4000* | 0.4000* |
| Ammonium solution (25 weight % aqueous sol.) | 0.3136 | 0.3136 | 0.3136 | 0.3136 | 0.3136 |
| Purified water | 76.2839 | 76.2839 | 78.2839 | 76.2839 | 73.7839 |
| Sum | 100.00 | 100.00 | 100.00 | 100.00 | 100.00 |
| Number of HPH of lipid phase (n) | 5 | 5 | 5 | 5 | 5 |
| Number of HPH of lipid suspension phase (m) | 3 | 3 | 3 | 3 | 3 |

Gelling agent:
*Carbomer (980),
** Xanthan gum,
Hydroxyethyl cellulose (Natrosol 250 HHX Pharm Bag),
: poloxamer 407
*micronized or ground PGA 2150619 pregabalin used. Phospholipid: LECITHIN,
LECITHIN (LIPOID P 75, LIPOID S 75),

| Batch No | PGA2330320* | AL2890321* | AL2900321* | AL2910321* |
|---|---|---|---|---|
| Process Type | WE-4 | WE-4 | WE-4 | WE-4 |
| Compound | g | g | g | g |
| Pregabalin | 10.0000 | 5.0000 | 5.0000 | 5.0000 |
| Phospholipid | 0.5000 | 0.5000 | 0.5000 | 0.5000 |
| Decylis oleas/Kollicream DO/ | 1.2500 | 1.2500 | 1.2500 | 1.2500 |
| Coconut oil | 5.0000 | 5.0000 | 5.0000 | 5.0000 |
| Isopropyl alcohol | 10.0000 | 10.0000 | 10.0000 | 10.0000 |
| DL-alpha-Tocopherol | 0.2500 | 0.2500 | 0.2500 | 0.2500 |
| EDTA | 0.0025 | 0.0025 | 0.0025 | 0.0025 |
| Benzyl alcohol | 1.0000 | 1.0000 | 1.0000 | 1.0000 |
| Gelling agent | 0.4000 | 1.5000** | 1.5000# | 15.0000## |
| Ammonium solution (25 weight % aqueous sol.) | 0.3136 | — | — | |
| Purified water | 71.2839 | 75.4975 | 75.4975 | 61.9975 |
| Sum | 100.00 | 100.00 | 100.00 | 100.00 |
| Number of HPH of lipid phase (n) | 5 | 5 | 5 | 5 |

-continued

| Batch No | PGA2330320* | AL2890321* | AL2900321* | AL2910321* |
|---|---|---|---|---|
| Number of HPH of lipid suspension phase (m) | 3 | 3 | 3 | 3 |

Gelling agent:
*Carbomer (980),
** Xanthan gum,
Hydroxyethyl cellulose (Natrosol 250 HHX Pharm Bag),
poloxamer 407
*micronized or ground PGA 2150619 pregabalin used. Phospholipid: LECITHIN,
LECITHIN (LIPOID P 75, LIPOID S 75), Results of a Mouse Model of Neuropathic Pain:

FIG. 5: Plantar withdrawal threshold diagrams 7 days after MPNL surgery in NMRI mice, effect of 20 μl PGA 2211119 cream (5% pregabalin, 20 μl/right foot, mean values±S.E.M. n=8), both feet.

| PGA2211119 T | Intact paw Átlag | Intact paw SEM | MPNL paw Átlag | MPNL paw SEM | Number of mice n | difference between the two paws p |
|---|---|---|---|---|---|---|
| kezdeti | 0.672 | 0.075 | 0.054 | 0.011 | 8 | * |
| +30 min | 0.688 | 0.044 | 0.783 | 0.108 | 8 | n.s. |
| +1 h | 0.900 | 0.038 | 0.863 | 0.056 | 8 | n.s. |
| +3 h | 0.688 | 0.044 | 0.700 | 0.057 | 8 | n.s. |
| +5 h | 0.697 | 0.088 | 0.623 | 0.078 | 8 | n.s. |
| +6 h | 0.785 | 0.073 | 0.597 | 0.113 | 8 | n.s. |
| +7 h | 0.623 | 0.069 | 0.348 | 0.109 | 8 | * |
| +8 h | 0.560 | 0.029 | 0.454 | 0.078 | 8 | n.s. | n.s.: not significant;
* $p < 0.05$

FIG. 4: Effect of 20 μl PGA 2150619 cream (5% pregabalin, 20 μl/right foot, mean values±S.E.M. n=6), both feet

| PGA2150619 T | Kezeletlen láb Átlag | Kezeletlen láb SEM | MPNL láb Átlag | MPNL láb SEM | egerek száma n | eltérés a két láb között p |
|---|---|---|---|---|---|---|
| kezdeti | 0.789 | 0.082 | 0.104 | 0.022 | 6 | * |
| +30 min | 0.733 | 0.071 | 0.933 | 0.042 | 6 | * |
| +1 h | 0.767 | 0.061 | 0.933 | 0.042 | 6 | n.s. |
| +3 h | 0.817 | 0.065 | 0.800 | 0.073 | 6 | n.s. |
| +5 h | 0.700 | 0.073 | 0.647 | 0.098 | 6 | n.s. | n.s.: not significant;
* $p < 0.05$

WE-5 General Procedure:

1. Preparation of gel phase:

In ten or twentyfold amount of purified water Carbopol 980 is swelled, then the pH is adjusted to pH 7.0 by adding aqueous ammonia solution.

2. Preparation of lipid phase:

In ten or twentyfold amount of purified water LIPOID P 75 (lecithin) is swelled at 25-40° C., then isopropyl alcohol and DL-alpha-Tocopherol are added to the mixture and homogenized.

3. HPH homogenization of the lipid phase:

The thus obtained solution is homogenized n=5 times by a High pressure homogenizer. The used pressure is preferably between 500-1500 bar. During HPH homogenization the solution warms up to 25-50° C. The thus obtained lipid phase is cooled to between 20-30° C. and if it is necessary the evaporated water is replaced by adding purified water while stirring.

4. The lipid phase is added to the gel phase while stirring, then the mixture of lipid phase and gel are homogenized for 30 minutes at 25° C.

5. To the homogenized mixture of lipid phase and gel phase further additives preferably coconut oil, Kollicream DO (Decylis oleas), an aqueous solution of EDTA and benzyl alcohol are added in this order.

6. Pregabalin is suspended in the rest of the water and homogenized for m=5 times with a high pressure homogenizer. The used pressure is preferably between 500-1500 bar. During the HPH homogenization the solution warms up to 30-50° C. Then the evaporated water is replaced with purified water if it is necessary.

7. The dispersion of pregabalin homogenized by HPH is mixed into the cream of point 5 at 30° C., then the obtained cream is homogenized for 120 min, then the evaporated water is replaced with purified water.

8. The thus obtained cream is cooled to 25° C. and filled into containers. (Preferably in aluminum or polyfoil tubes.)

Compositions Prepared According to WE-5 Process:

| BatchNo. | PGA2050519 |
|---|---|
| Process type | WE-5 |
| Compound | g |
| Pregabalin (ground) | 5.0000 |
| LECITHIN (LIPOID P 75) | 0.5000 |
| Decylis oleas/Kollicream DO/ | 1.2500 |
| Coconut oil refined | 5.0000 |
| Isopropyl alcohol | 10.0000 |
| DL-alpha-Tocopherol | 0.2500 |
| Benzylalcohol | 1.0000 |
| EDTA | 0.0025 |
| Carbomers (980) | 0.4000 |
| Ammonium solution (25 weight % aqueous sol.) | 0.3136 |

| | |
|---|---|
| All ingredients | 23.7161 |
| Purified water | 76.2839 |
| | 100.00 |
| Number of HPH of lipid phase (n) | 5 |
| Number of pregabalin dispersion (m) | 5 |

The invention claimed is:

1. A topical pharmaceutical composition comprising 2.5-40 weight % of pregabalin, and 0.1-3 weight %, of a phospholipid, wherein the pregabalin and the phospholipid are in dispersed form and wherein a micelle contribution scaling factor ($I_0$) derived from a diagram of a Small-angle X-ray scattering measurement is less than or equal to 0.00025 $cm^{-1}sr^{-1}$; wherein the phospholipid has been homogenized with a high pressure homogenizer, and wherein a pain alleviation effect is extended compared to a composition with the same components where the phospholipid has not been homogenized with a high pressure homogenizer.

2. The topical pharmaceutical composition according to claim 1, which is semisolid.

3. The topical pharmaceutical composition according to claim 1, further comprising
   40-90 weight % of one or more solvents,
   0-20 weight % of one or more emollients,
   0-20 weight % of one or more penetration enhancers,
   0-5 weight % of one or more rheology modifiers, and
   optionally one or more pH modifiers.

4. The topical pharmaceutical composition according to claim 1, wherein the phospholipid is a natural or synthetic phospholipid, and the composition further comprises one or more of the following
   a solvent selected from the group consisting of water, pharmaceutically acceptable $C_2$-$C_4$ alcohols, alcohols having more than one hydroxyl group, isopropanol and mixtures thereof,
   an emollient selected from the group consisting of vitamin A, vitamin D, vitamin E, lanolin, lanolin alcohol, propylene glycol di-benzoate, vegetable oils, plant extracts, fatty alcohol esters, fatty acid esters, fatty alcohols, synthetic polymers, silicon compounds, fatty acids, mineral oil derivatives, waxes and mixtures thereof,
   a penetration enhancer, that is not the phospholipid, selected from the group consisting of $C_2$-$C_4$ alcohols, DL-alpha-tocopherol, and mixtures thereof,
   a preservative selected from the group consisting of EDTA, EDTA derivatives, and aromatic preservatives and mixtures thereof,
   a rheology modifier selected from the group consisting of poloxamer, polyethylene glycol, synthetic polymers and mixtures thereof, and/or
   a pH modifier that is base pH modifier.

5. The topical pharmaceutical composition according to claim 1, wherein the pregabalin is ground pregabalin and has a $D_{90}$ of particle size of 20-200 micrometer.

6. The topical pharmaceutical composition according to claim 1, which comprises 3-20 weight % of the pregabalin and 0.5-1.5 weight % of the phospholipid, wherein the pregabalin and the phospholipid are in dispersed form and wherein the micelle contribution scaling factor ($I_0$) derived from the diagram of the Small-angle X-ray scattering measurement is less than or equal to 0.00023 $cm^{-1}sr^{-1}$.

7. The topical pharmaceutical composition according to claim 1, which is semisolid in a form of a gel, cream, or gel-cream.

8. The topical pharmaceutical composition according to claim 1, further comprising
   70-90 weight % of one or more solvents,
   3-10 weight % of one or more emollients,
   2-15 weight % of one or more penetration enhancers,
   0.1-2 weight % of one or more rheology modifiers, and
   optionally one or more pH modifiers.

9. The topical pharmaceutical composition according to claim 1, wherein the phospholipid is selected from the group consisting of soya lecithin, deoiled soya lecithin, hydrogenated soya lecitin comprising about 70 weight % of phospholipids and about 30 weight % of a mixture of fatty acids, soya lecitin comprising about 70 weight % of phospholipids and about 30 weight % of a mixture of fatty acids, and mixtures thereof
   and the composition further comprises one or more of the following
   a solvent selected from the group consisting of water, ethanol, propanol, isopropanol, n-butanol, iso-butanol, glycerol, propylene glycol, and mixtures thereof,
   an emollient selected from the group consisting of fatty acid ester cetyl palmitate,
   octyldodecanol, decylis oleas, coconut oil, and mixtures thereof,
   a penetration enhancer besides the phospholipid selected from the group consisting of $C_2$-$C_4$ alcohols, DL-alpha-tocopherol, and mixtures thereof,
   a preservative selected from the group consisting of EDTA, para-hydroxy benzoates, thimerosal, chlorohexidine benzyl alcohol, benzalkonium chloride benzyl alcohol, and mixtures thereof,
   a rheology modifier selected from the group consisting of carbomers, carbomer 980, hydroxyalkyl celluloses, hydroxyethyl cellulose, vegetable gums, xanthan gum, guar gum, and mixtures thereof, and/or
   a pH modifier selected from the group consisting of ammonia, ammonium solution, alkali earth metal hydroxides, alkali earth metal hydroxides, carbonates, hydro-carbonates, organic bases, primary amines, secondary amines, tertiary amines and mixtures thereof.

10. The topical pharmaceutical composition according to claim 1, comprising 3-15 weight %, of pregabalin, 0.5-1.5 weight % of a phospholipid, wherein the pregabalin and the phospholipid are in dispersed form and wherein the micelle contribution scaling factor ($I_0$) derived from the diagram of the Small-angle X-ray scattering measurement is less than equal to 0.00023 $cm^{-1}sr^{-1}$, and further comprising 70-90 weight % of one or more solvents 3-10 weight % of emollients one or more, 0-20 weight % of one or more penetration enhancers, 0.1-2 weight % of one or more rheology modifiers and optionally one or more pH modifiers, wherein the phospholipid is selected from the group consisting of soya lecithin, deoiled soya lecithin, soya lecitin comprising about 70 weight % of phospholipids and about 30 weight % of a mixture of fatty acids, soya lecitin comprising about 70 weight % of phospholipids and about 30 weight % of a mixture of fatty acids, wherein the solvent is selected from the group consisting of water, ethanol, propanol, isopropanol, and mixtures thereof, the emollient is selected from the group consisting of cetyl palmitate, octyldodecanol, decylis oleas, coconut oil, and mixtures thereof, the penetration enhancer besides the phospholipid is selected from the group consisting of $C_2$-$C_4$ alcohols, DL-alpha-tocopherol and mixtures thereof, the preservative is selected from the group consisting of benzyl alcohol and a mixture of benzyl alcohol and EDTA, and the pH modifier is ammonia or an aqueous ammonium solution.

11. The topical pharmaceutical composition according to claim 1, wherein the pregabalin is micronized and has a $D_{90}$ of particle size below 20 micrometers.

* * * * *